(12) United States Patent
Stephenson et al.

(10) Patent No.: US 9,907,923 B2
(45) Date of Patent: Mar. 6, 2018

(54) VALSALVA MASK

(71) Applicant: Fisher & Paykel Healthcare Limited, Auckland (NZ)

(72) Inventors: Matthew Roger Stephenson, London (GB); Melissa Catherine Bornholdt, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 15/630,800

(22) Filed: Jun. 22, 2017

(65) Prior Publication Data

US 2017/0326319 A1 Nov. 16, 2017

Related U.S. Application Data

(63) Continuation of application No. 14/425,599, filed as application No. PCT/NZ2013/000155 on Sep. 3, 2013.

(60) Provisional application No. 61/696,756, filed on Sep. 4, 2012.

(51) Int. Cl.
*A61M 16/06* (2006.01)
*A61M 16/20* (2006.01)
*A61M 16/08* (2006.01)

(52) U.S. Cl.
CPC ........ *A61M 16/0605* (2014.02); *A61M 16/06* (2013.01); *A61M 16/065* (2014.02); *A61M 16/0633* (2014.02); *A61M 16/0683* (2013.01); *A61M 16/0825* (2014.02); *A61M 16/208* (2013.01); *A61M 16/0616* (2014.02); *A61M 2205/15* (2013.01); *A61M 2210/0618* (2013.01)

(58) Field of Classification Search
CPC .............. A61M 16/06; A61M 16/0605; A61M 16/0611; A61M 16/0616; A61M 16/0622; A61M 16/0683; A61M 2016/0661
See application file for complete search history.

(56) References Cited

U.S. PATENT DOCUMENTS

| | | |
|---|---|---|
| 1,710,160 A | 4/1929 | Gibbs |
| 2,228,218 A | 1/1941 | Schwartz |
| 2,376,871 A | 5/1945 | Fink |
| 2,415,846 A | 2/1947 | Randall |
| 2,706,983 A | 4/1955 | Matheson et al. |
| 2,858,828 A | 11/1958 | Matheson |
| 2,874,693 A | 2/1959 | Matheson |

(Continued)

FOREIGN PATENT DOCUMENTS

| | | |
|---|---|---|
| AU | 2004201337 | 10/2005 |
| CA | 2440431 A1 | 3/2004 |

(Continued)

OTHER PUBLICATIONS

International Search Report and Written Opinion dated Dec. 6, 2013, in International Application No. PCT/NZ2013/000155.

*Primary Examiner* — Lynne Anderson
(74) *Attorney, Agent, or Firm* — Knobbe Martens Olson & Bear LLP

(57) ABSTRACT

An interface for positive pressure therapy includes a mask assembly and a headgear assembly. The mask assembly comprises a mask seal that is adapted to underlie the nose. The mask seal extends up the lateral sides of the nose. The mask seal has a primary seal below the nose and a secondary seal alongside the nose.

18 Claims, 63 Drawing Sheets

(56) References Cited

U.S. PATENT DOCUMENTS

| | | | |
|---|---|---|---|
| 2,881,444 A | 4/1959 | Fresh et al. | |
| 2,893,387 A | 7/1959 | Gongoll et al. | |
| 2,931,356 A | 4/1960 | Schwarz | |
| 2,939,458 A | 6/1960 | Lundquist | |
| 2,999,498 A | 9/1961 | Matheson | |
| 3,037,501 A | 6/1962 | Miller | |
| 3,330,273 A * | 7/1967 | Ray | A61M 16/06 128/206.26 |
| 3,545,436 A | 12/1970 | Holloway | |
| 3,969,991 A | 7/1976 | Comstock et al. | |
| 4,069,516 A | 1/1978 | Watkins, Jr. | |
| 4,167,185 A | 9/1979 | Lewis | |
| 4,641,379 A | 2/1987 | Martin | |
| 4,739,755 A | 4/1988 | White et al. | |
| 4,770,169 A | 9/1988 | Schmoegner et al. | |
| 4,907,584 A | 3/1990 | McGinnis | |
| 5,074,297 A | 12/1991 | Venegas | |
| 5,121,745 A | 6/1992 | Israel | |
| 5,349,949 A * | 9/1994 | Schegerin | A62B 18/08 128/201.24 |
| 5,353,789 A | 10/1994 | Schlobohm | |
| 5,355,878 A | 10/1994 | Griffiths et al. | |
| 5,842,470 A | 12/1998 | Ruben | |
| 5,921,239 A | 7/1999 | McCall et al. | |
| 6,016,804 A | 1/2000 | Gleason et al. | |
| 6,418,928 B1 | 7/2002 | Bordewick et al. | |
| 6,467,483 B1 | 10/2002 | Kopacko et al. | |
| 6,851,428 B2 | 2/2005 | Dennis | |
| D582,546 S | 12/2008 | Fujiura et al. | |
| 7,827,990 B1 | 11/2010 | Melidis et al. | |
| 8,146,595 B2 | 4/2012 | Sherman | |
| 8,276,588 B1 | 10/2012 | Connor et al. | |
| 8,596,276 B2 | 12/2013 | Omura et al. | |
| 8,887,728 B2 * | 11/2014 | Boussignac | A61M 16/06 128/201.24 |
| 9,149,593 B2 | 10/2015 | Dravitzki et al. | |
| 2003/0019495 A1 | 1/2003 | Palkon et al. | |
| 2003/0019496 A1 | 1/2003 | Kopacko et al. | |
| 2003/0075180 A1 | 4/2003 | Raje et al. | |
| 2004/0107968 A1 | 6/2004 | Griffiths | |
| 2005/0199239 A1 | 9/2005 | Lang et al. | |
| 2006/0130844 A1 | 6/2006 | Ho et al. | |
| 2006/0207599 A1 | 9/2006 | Busch et al. | |
| 2007/0044804 A1 | 3/2007 | Matula, Jr. et al. | |
| 2007/0125385 A1 | 6/2007 | Ho et al. | |
| 2007/0221226 A1 | 9/2007 | Hansen et al. | |
| 2008/0032036 A1 | 2/2008 | Ito et al. | |
| 2008/0223373 A1 | 9/2008 | Chang | |
| 2008/0230068 A1 | 9/2008 | Rudolph | |
| 2009/0014008 A1 | 1/2009 | Takishita et al. | |
| 2009/0110141 A1 | 4/2009 | Ging et al. | |
| 2009/0126739 A1 | 5/2009 | Ng et al. | |
| 2009/0139526 A1 | 6/2009 | Melidis et al. | |
| 2009/0139527 A1 | 6/2009 | Ng et al. | |
| 2009/0178679 A1 | 7/2009 | Lithgow et al. | |
| 2009/0183739 A1 | 7/2009 | Wondka | |
| 2010/0043798 A1 | 2/2010 | Sullivan et al. | |
| 2010/0294281 A1 | 11/2010 | Ho | |
| 2010/0319700 A1 | 12/2010 | Ng et al. | |
| 2011/0146684 A1 | 6/2011 | Wells et al. | |
| 2011/0197341 A1 | 8/2011 | Formica et al. | |
| 2011/0220112 A1 | 9/2011 | Connor | |
| 2011/0247625 A1 * | 10/2011 | Boussignac | A61M 16/06 128/205.25 |
| 2012/0080035 A1 | 4/2012 | Guney et al. | |
| 2012/0234326 A1 | 9/2012 | Mazzone et al. | |
| 2012/0285469 A1 | 11/2012 | Ho et al. | |
| 2014/0041664 A1 | 2/2014 | Lynch et al. | |
| 2014/0338671 A1 | 11/2014 | Chodkowski et al. | |
| 2014/0366886 A1 | 12/2014 | Chodkowski et al. | |
| 2015/0013682 A1 | 1/2015 | Hendriks et al. | |
| 2015/0246199 A1 | 9/2015 | Matula, Jr. et al. | |
| 2016/0067437 A1 | 3/2016 | Zollinger et al. | |
| 2016/0129210 A1 | 5/2016 | Matula, Jr. et al. | |

FOREIGN PATENT DOCUMENTS

| | | |
|---|---|---|
| DE | 1226422 B | 10/1966 |
| DE | 19603949 A1 | 8/1997 |
| EP | 0303090 | 2/1989 |
| EP | 1582231 | 10/2005 |
| EP | 1 632 262 | 3/2006 |
| FR | 1299470 | 7/1962 |
| GB | 309770 | 4/1929 |
| GB | 761263 A | 11/1956 |
| GB | 823887 | 11/1959 |
| GB | 2393126 | 3/2004 |
| JP | S472239 Y1 | 1/1972 |
| JP | S488995 U | 1/1973 |
| JP | S4947495 U | 4/1974 |
| JP | S4985895 U | 7/1974 |
| JP | S5287095 U | 6/1977 |
| JP | S57182456 U | 11/1982 |
| JP | S61156943 U | 9/1986 |
| JP | S61185446 U | 11/1986 |
| JP | S63184062 U | 11/1988 |
| JP | 11397 | 1/1999 |
| JP | 3160631 U | 7/2010 |
| NZ | 608551 | 10/2014 |
| WO | WO 0162326 | 8/2001 |
| WO | WO 2004022146 | 3/2004 |
| WO | WO2004/041342 | 5/2004 |
| WO | WO 2004/041342 | 5/2004 |
| WO | WO 2004071565 | 8/2004 |
| WO | WO 2005123166 | 12/2005 |
| WO | WO2006/074513 | 7/2006 |
| WO | WO 2006/074513 | 7/2006 |
| WO | WO 2006074515 | 7/2006 |
| WO | WO 2006138416 | 12/2006 |
| WO | WO 2007/021777 | 2/2007 |
| WO | WO2007/059504 | 5/2007 |
| WO | WO 2007/059504 | 5/2007 |
| WO | WO 2007147088 | 12/2007 |
| WO | WO 2009108995 | 9/2009 |
| WO | WO2010/009877 | 1/2010 |
| WO | WO 2010/148453 | 12/2010 |
| WO | WO 2011/022751 | 3/2011 |
| WO | WO2013/084110 | 6/2013 |
| WO | WO2014/038959 | 3/2014 |
| WO | WO2014/077708 | 5/2014 |
| WO | WO2014/141029 | 9/2014 |
| WO | WO2014/181214 | 11/2014 |
| WO | WO2016149769 | 9/2016 |

* cited by examiner

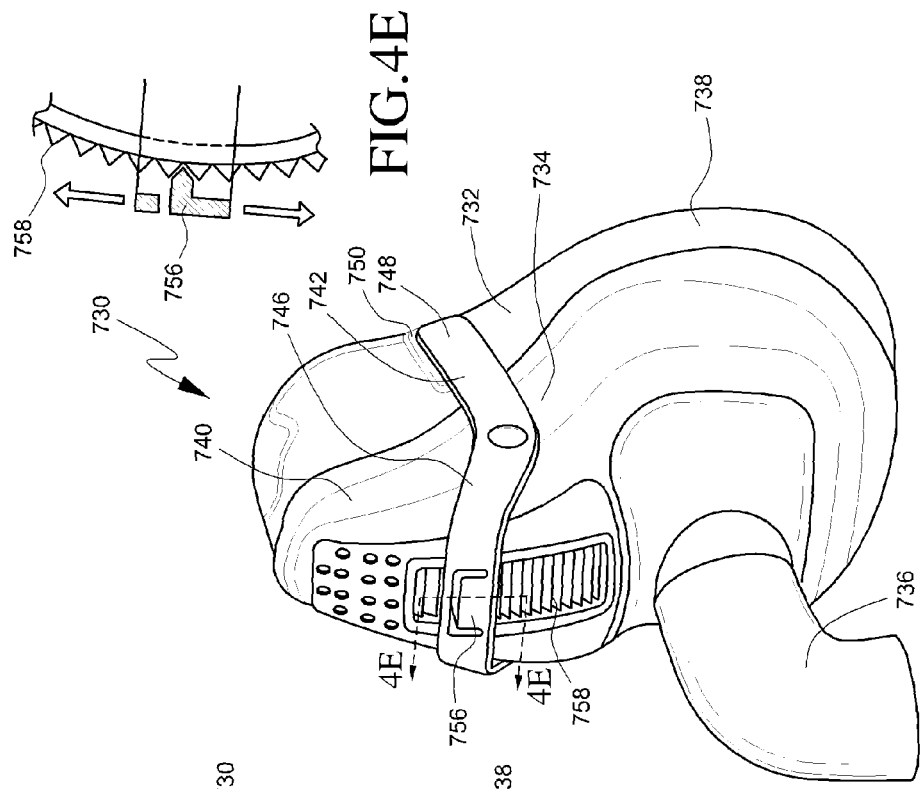
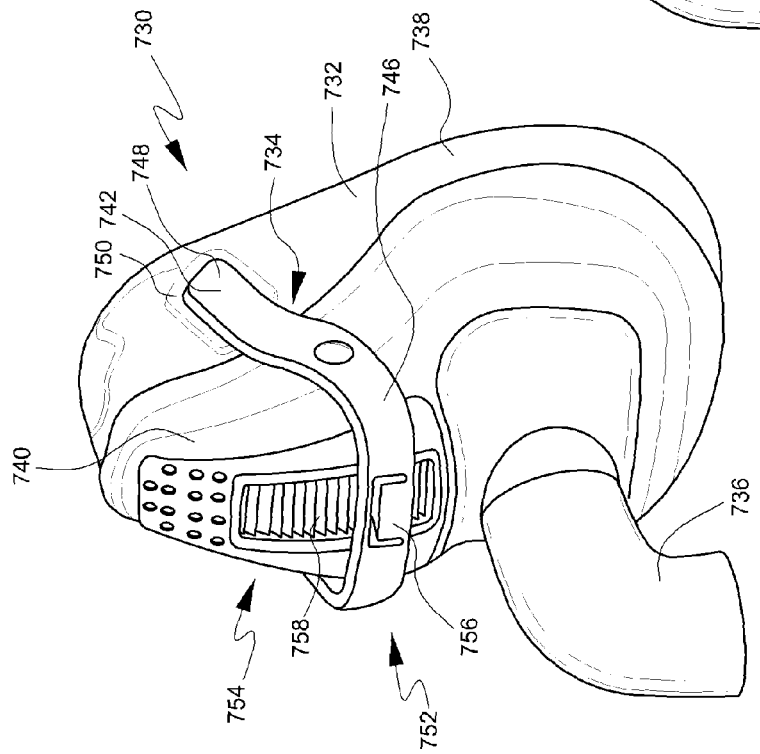

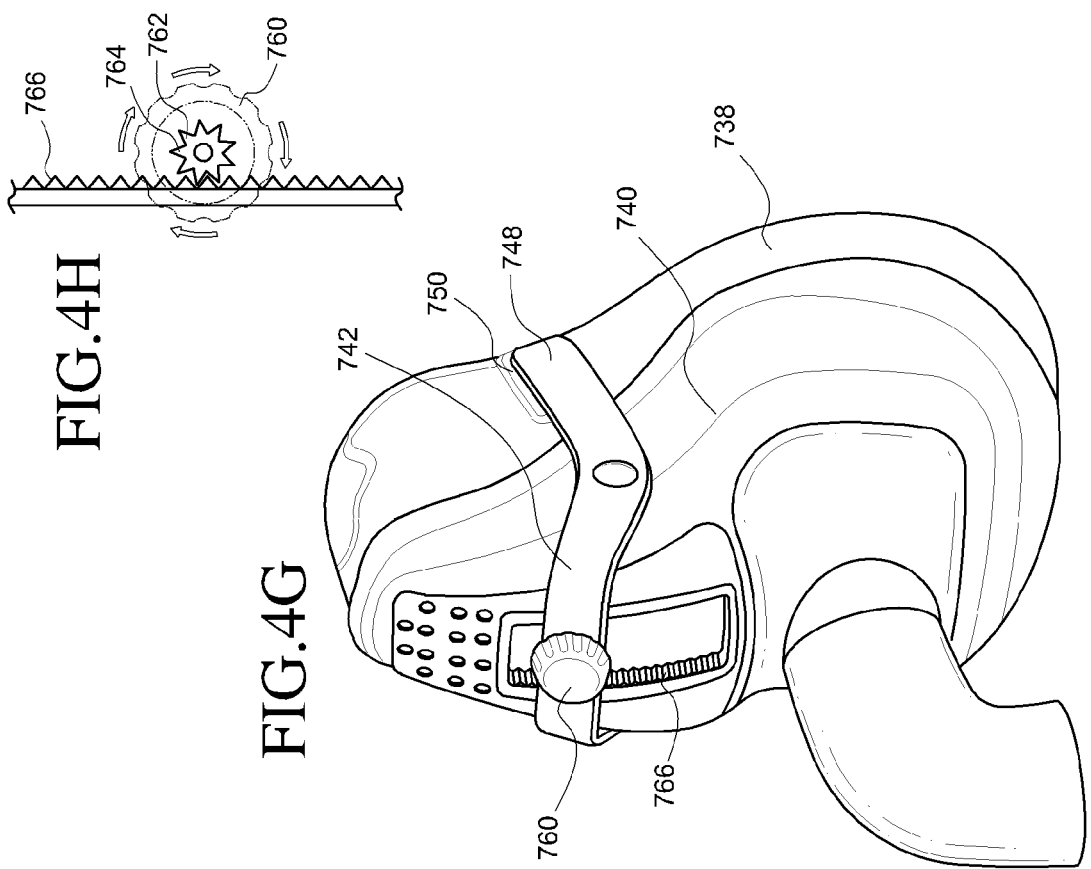
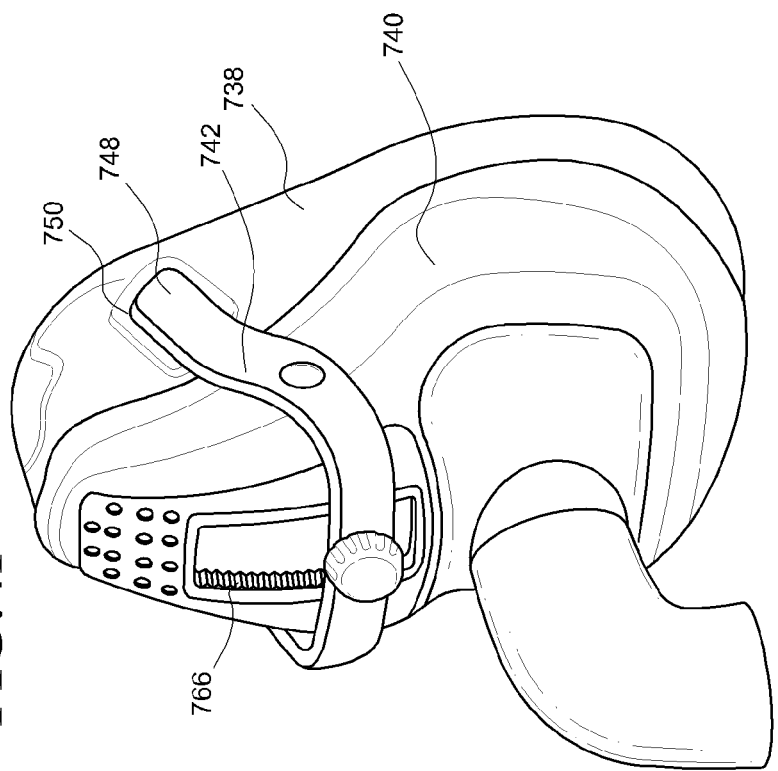

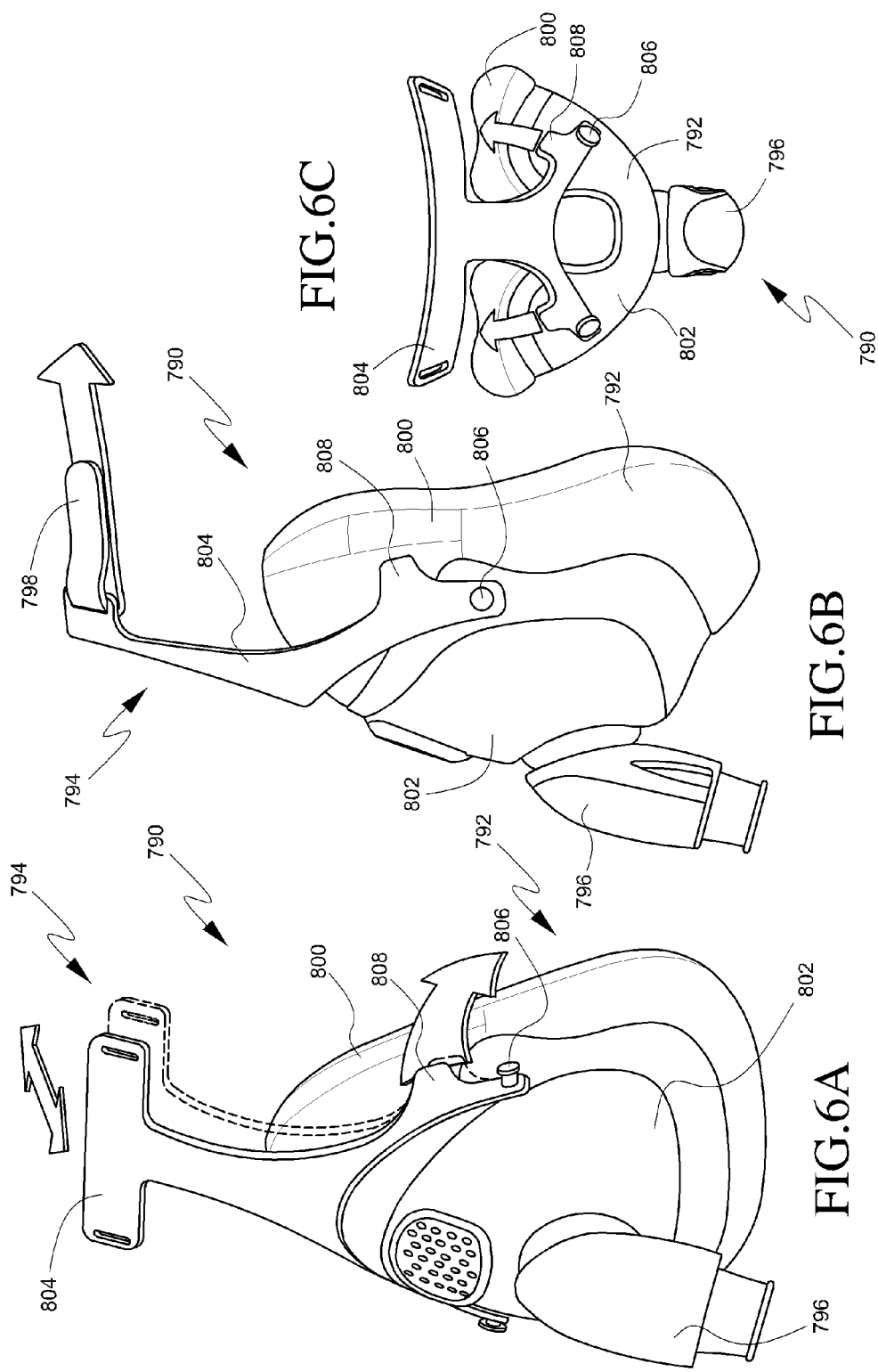

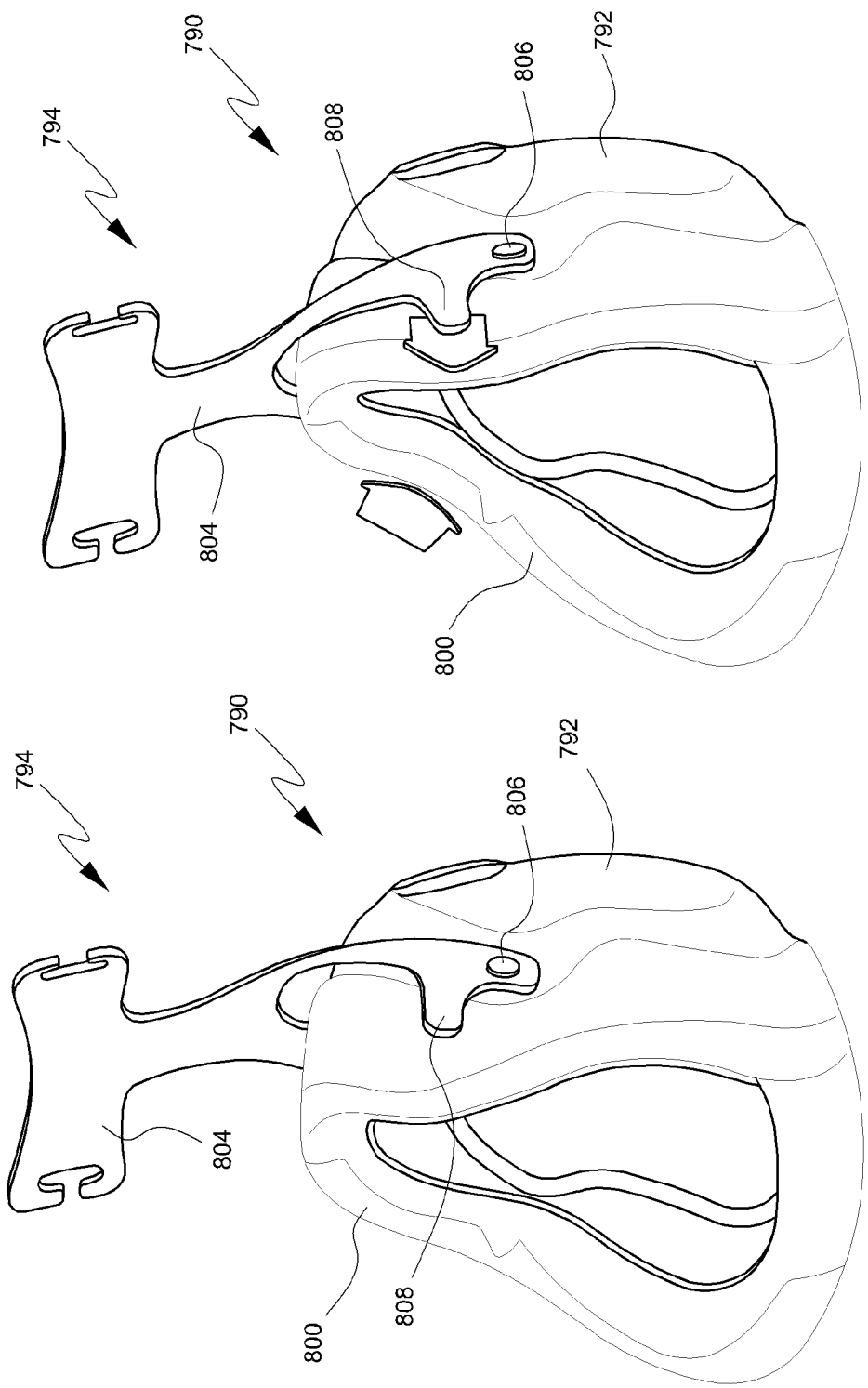

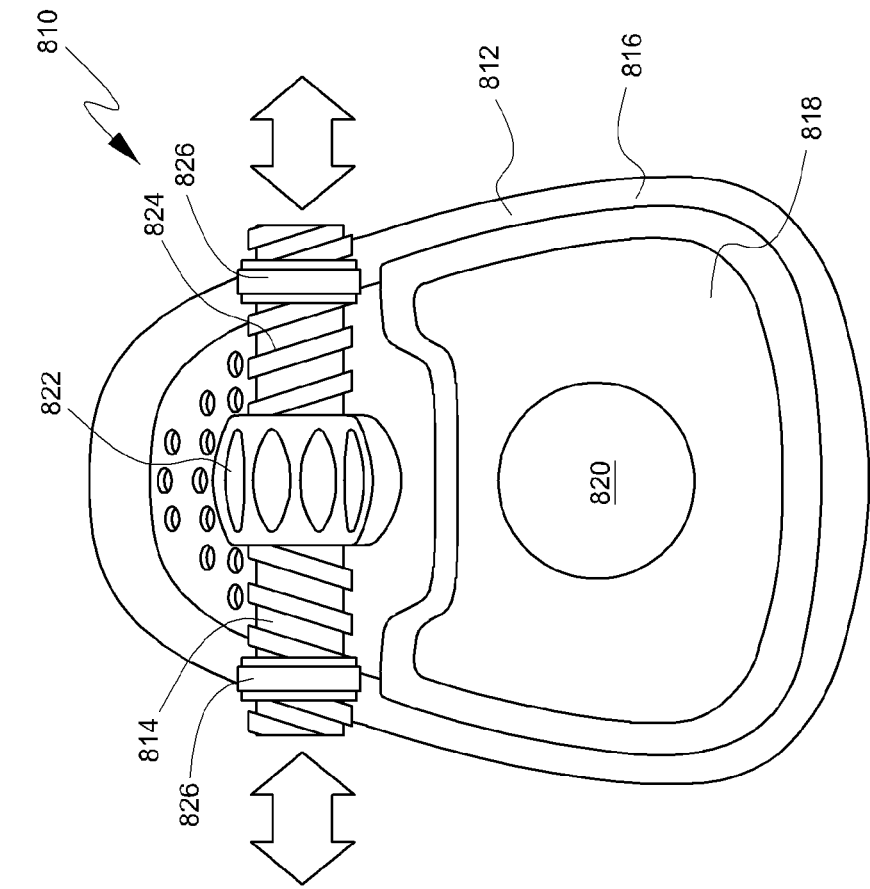
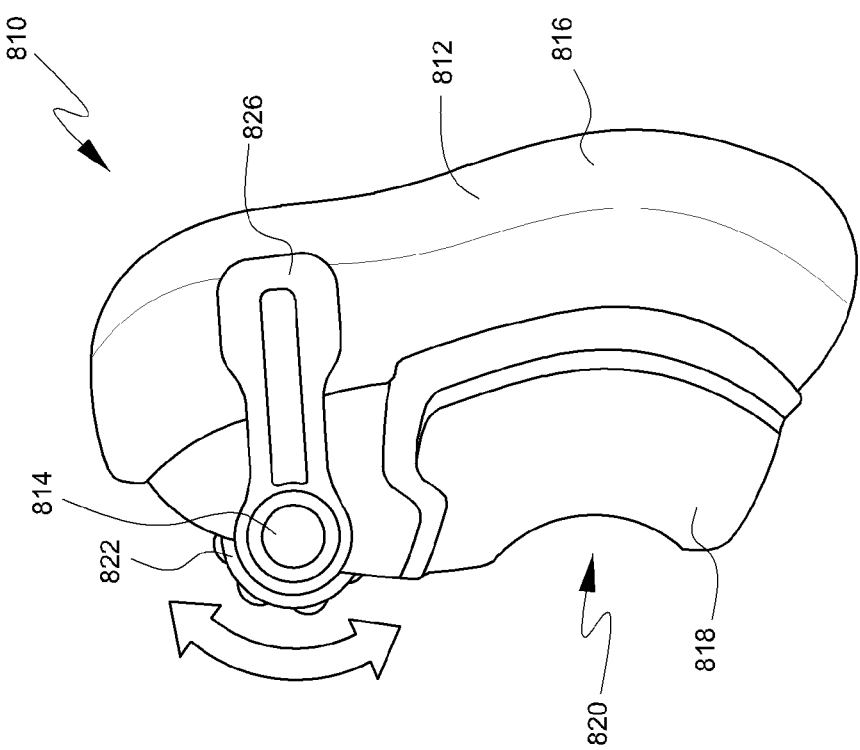
FIG.7B
FIG.7A

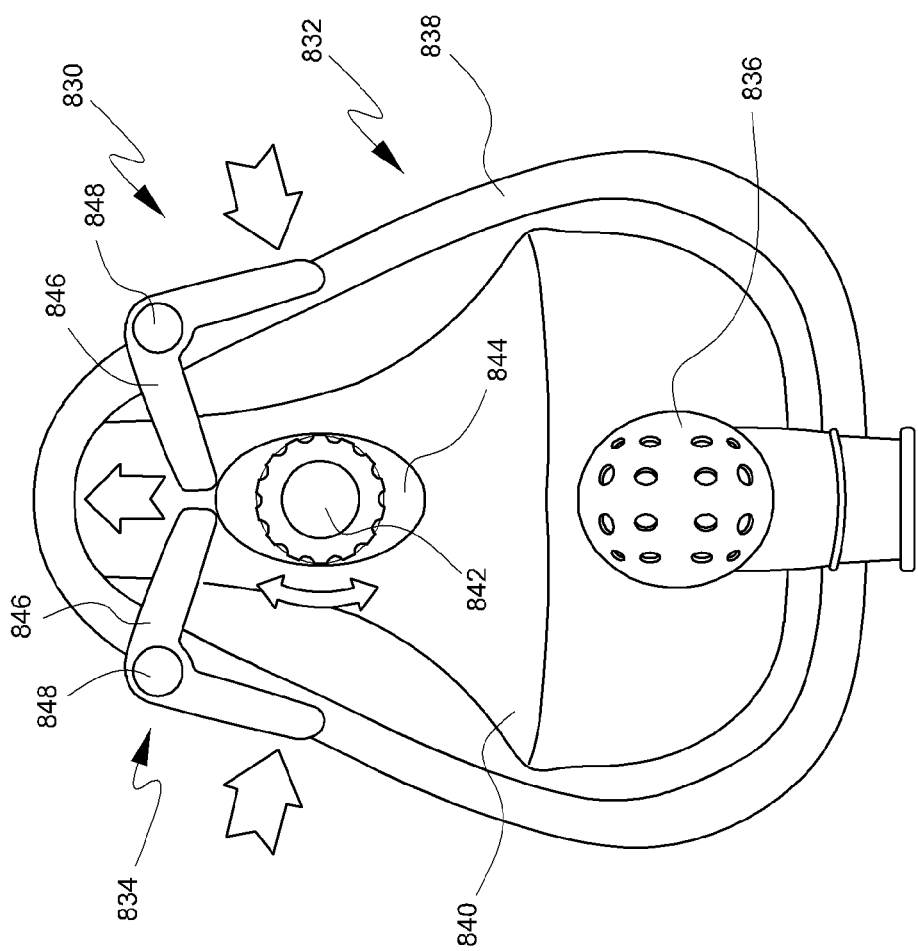
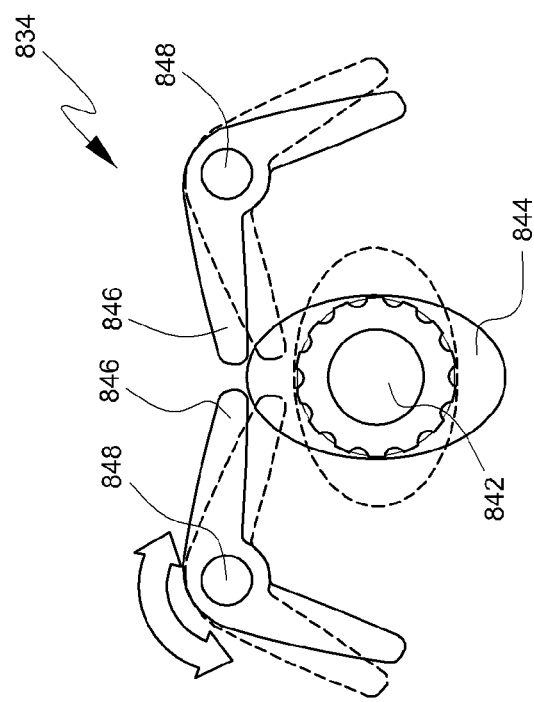
FIG.8A
FIG.8B

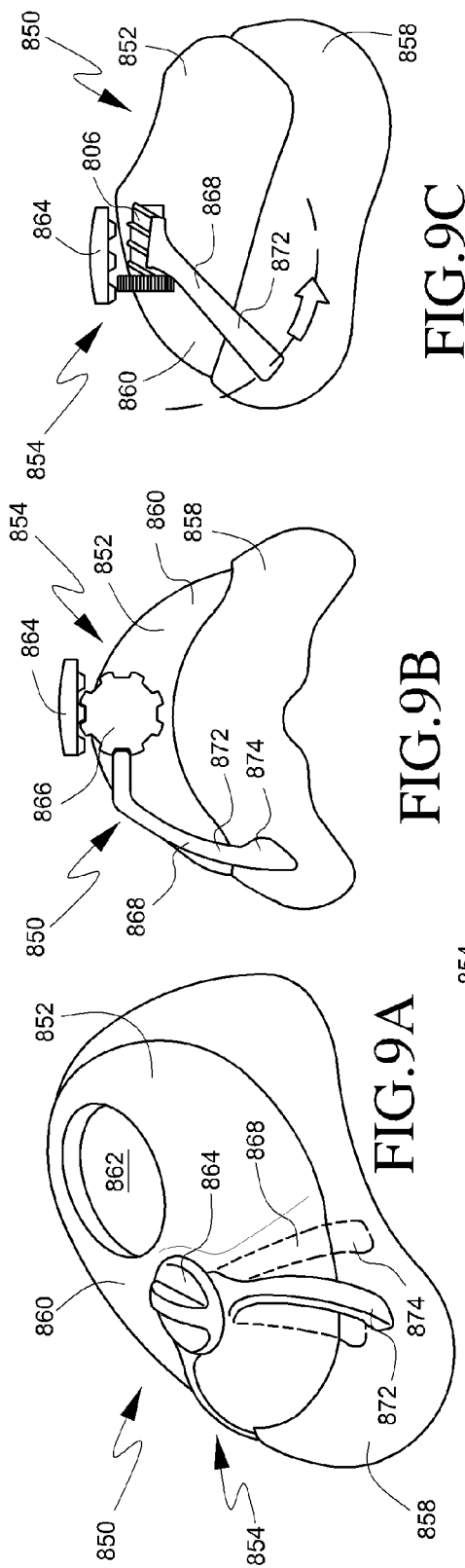
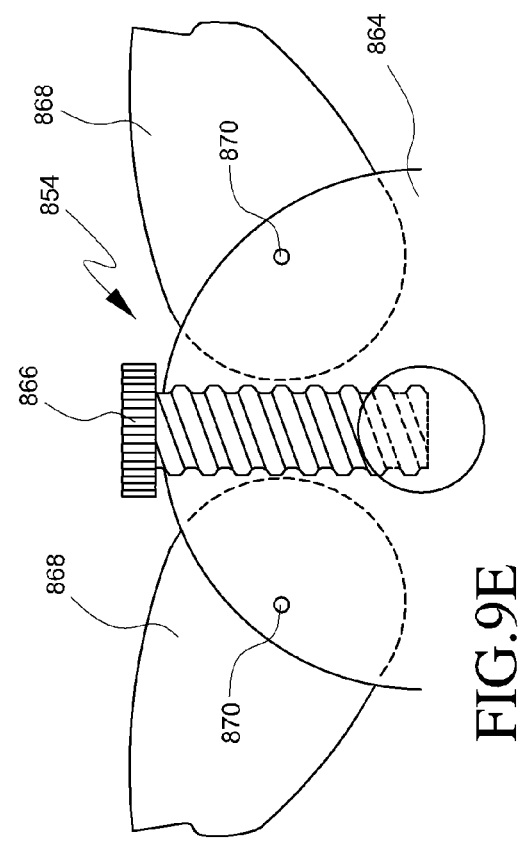
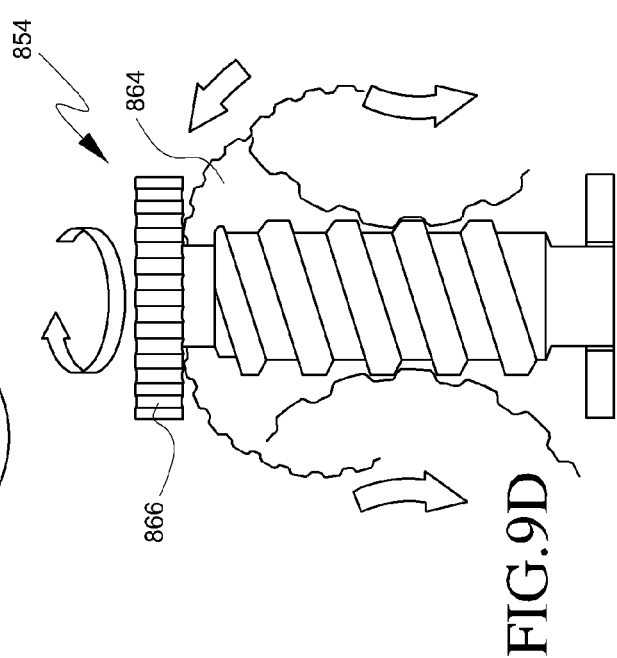
FIG.9A FIG.9B FIG.9C FIG.9D FIG.9E

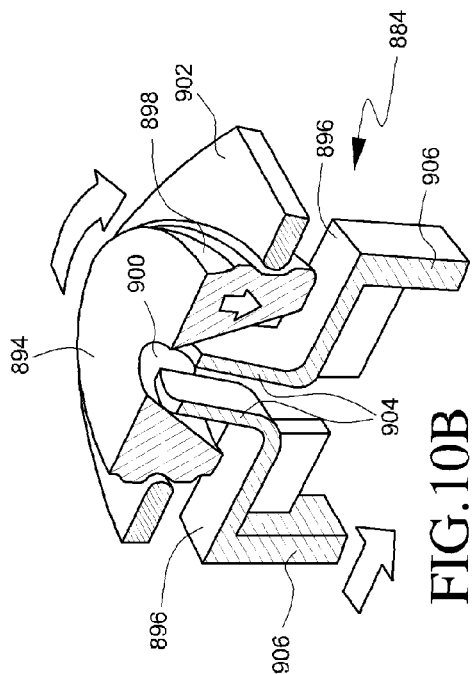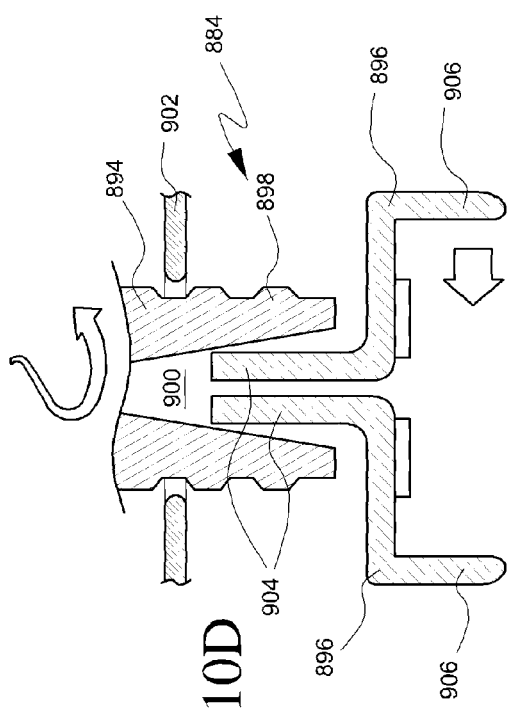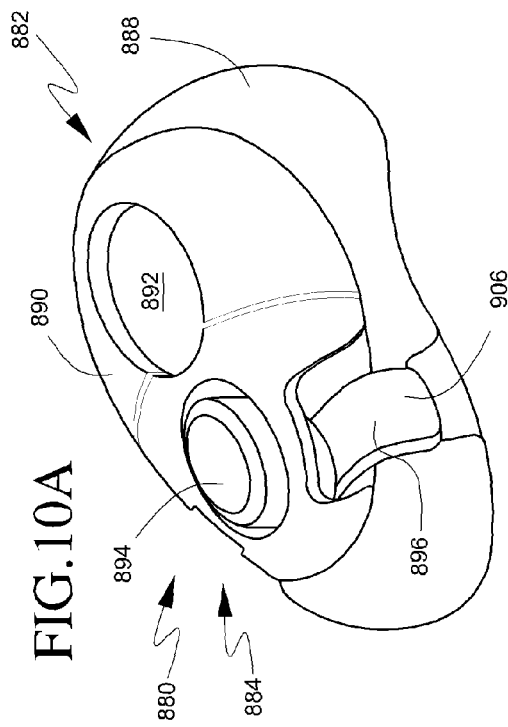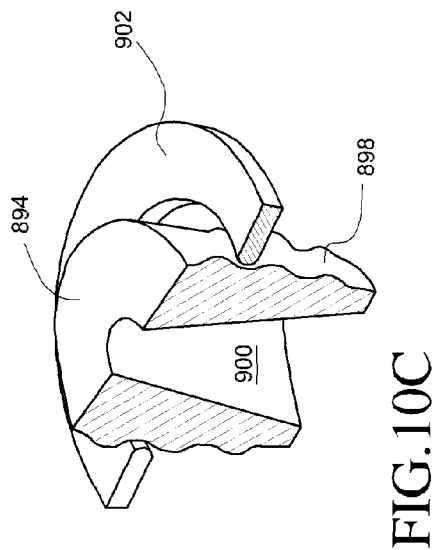

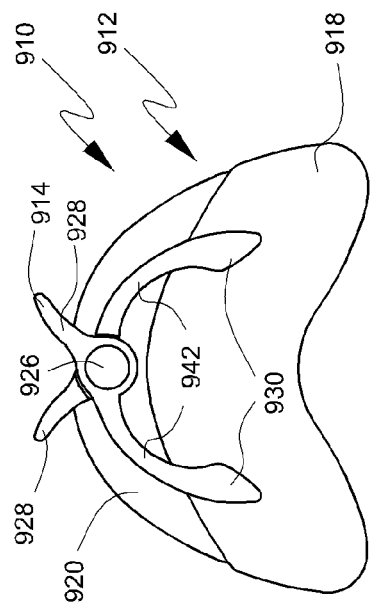
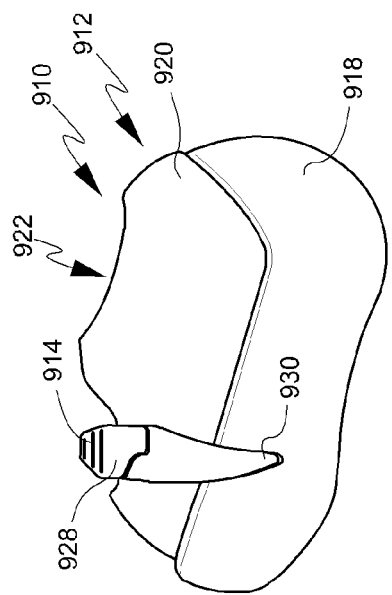
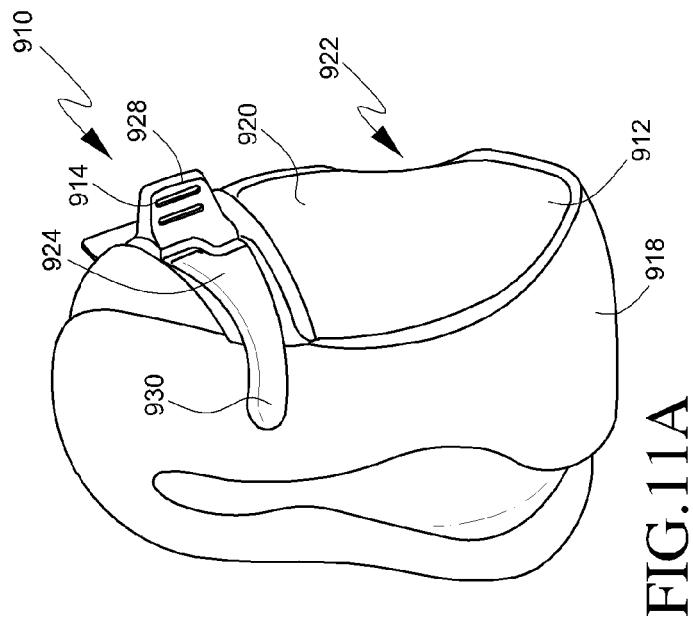

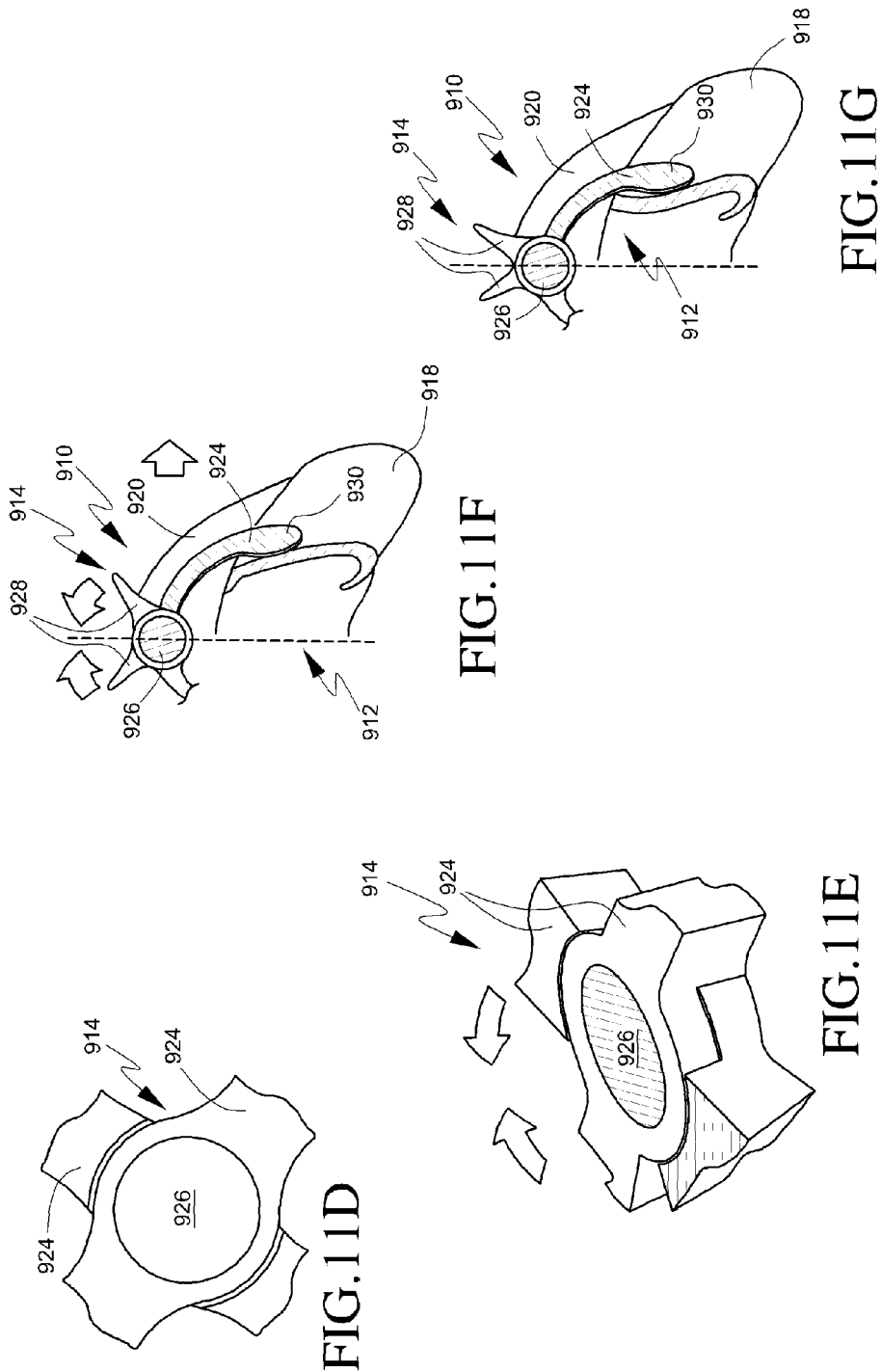

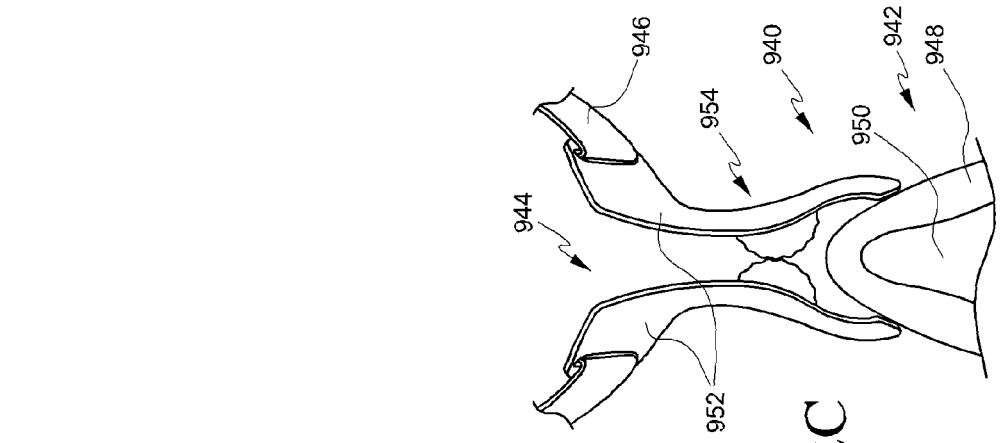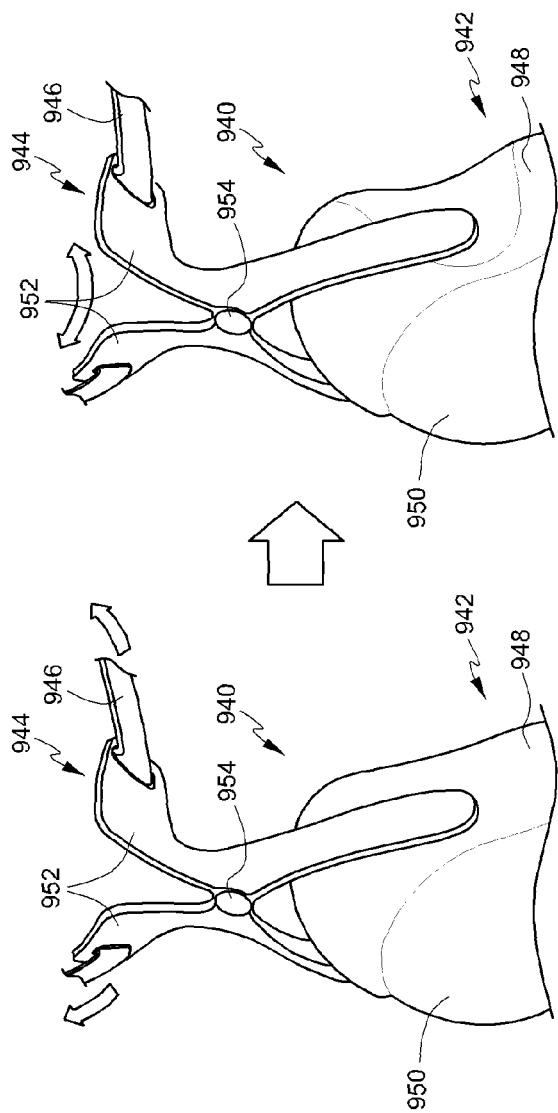

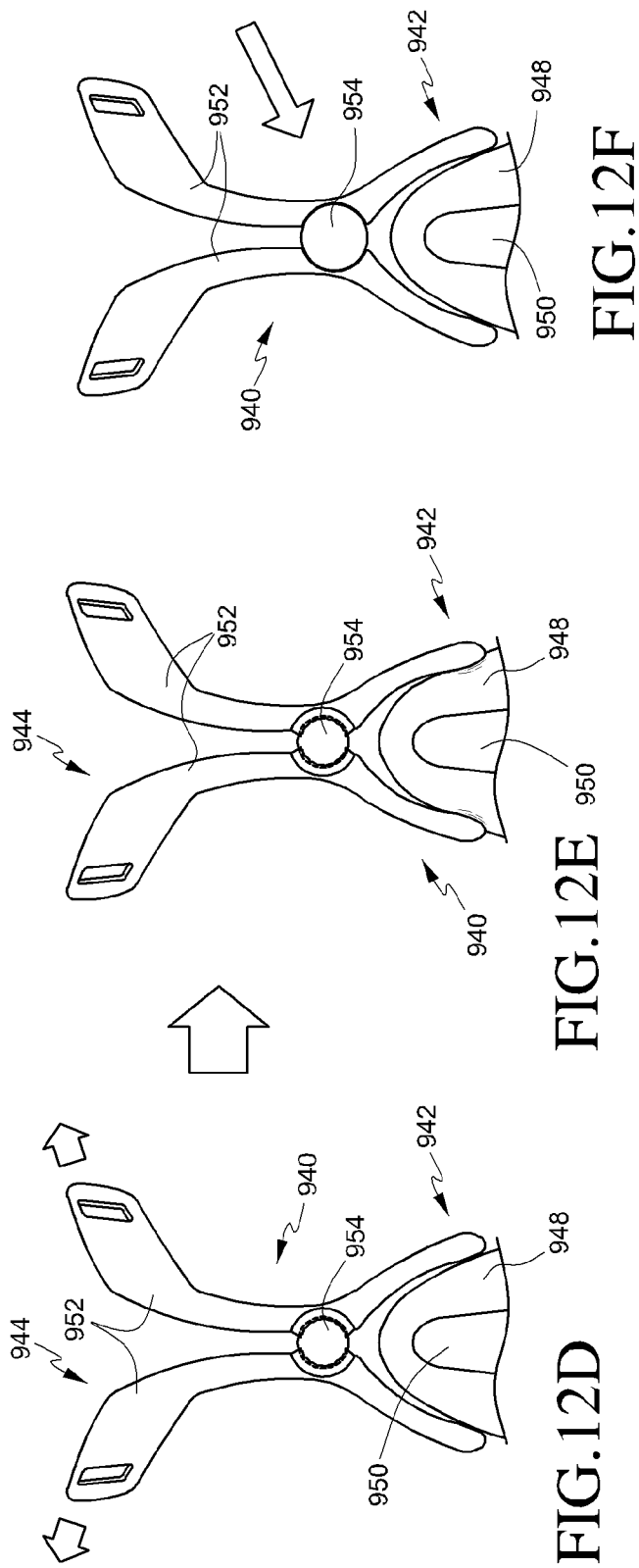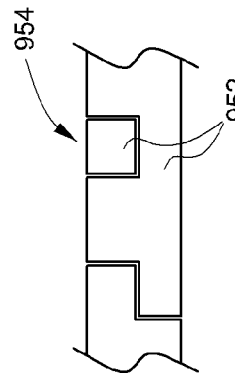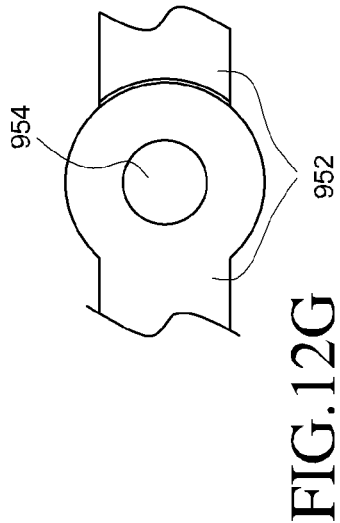

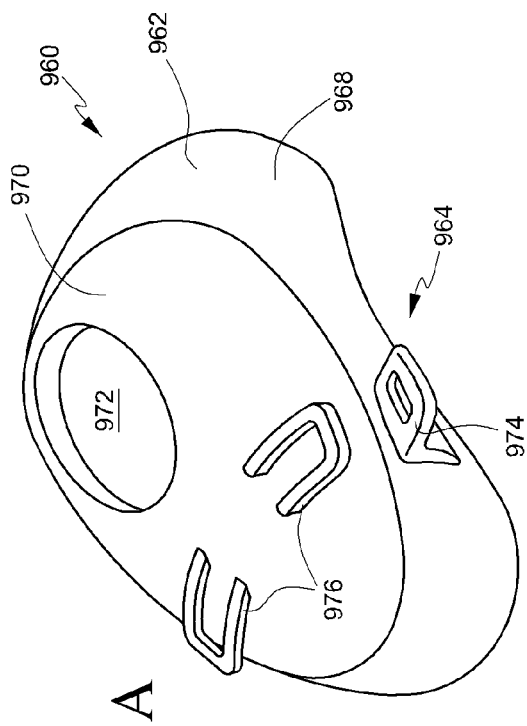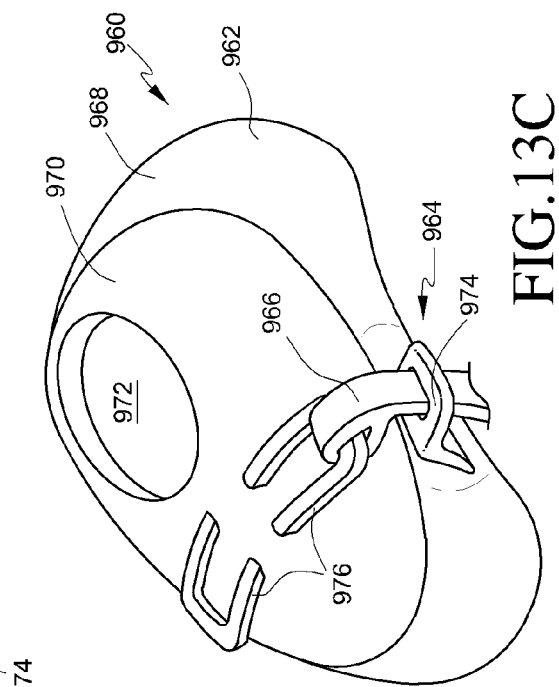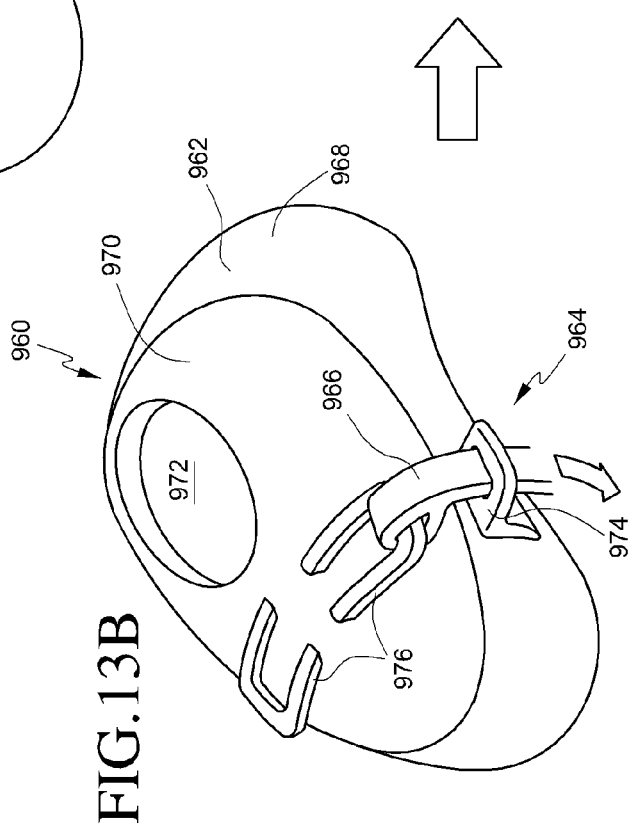

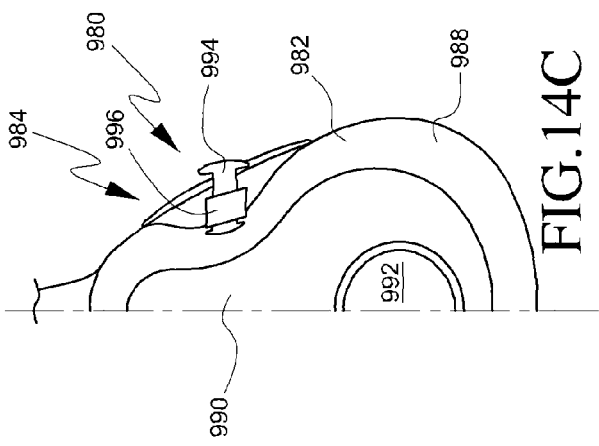
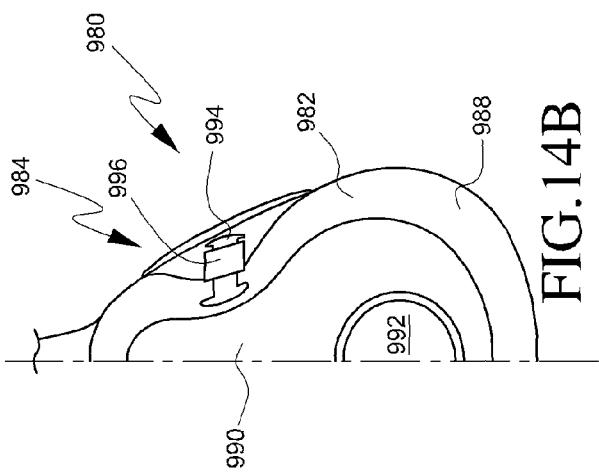
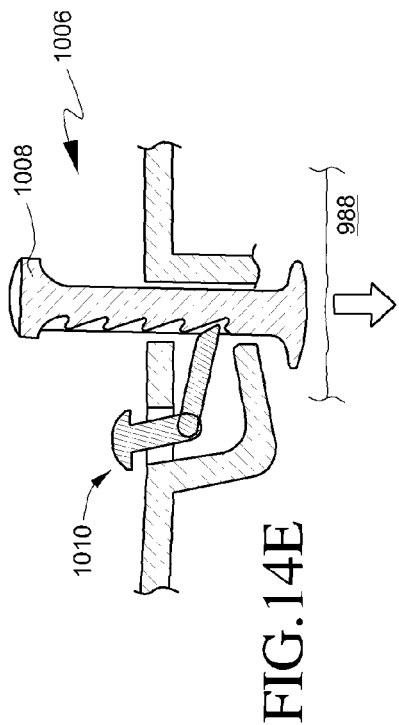
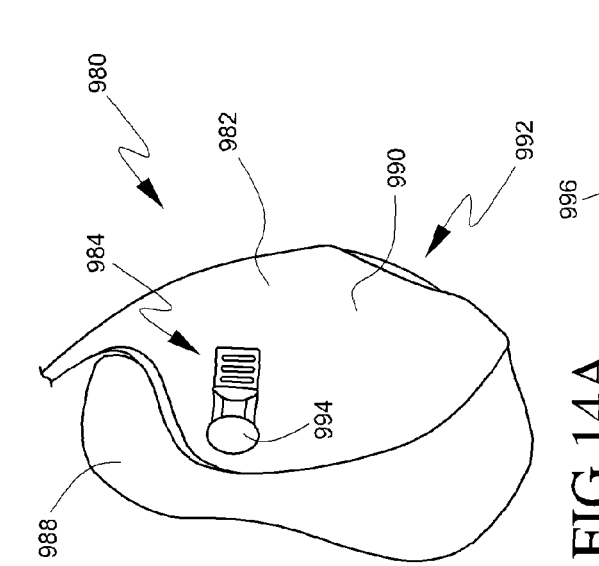
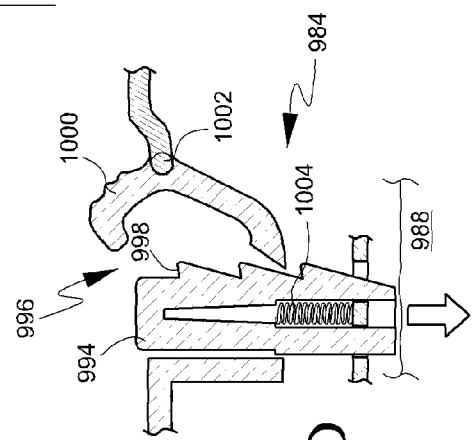

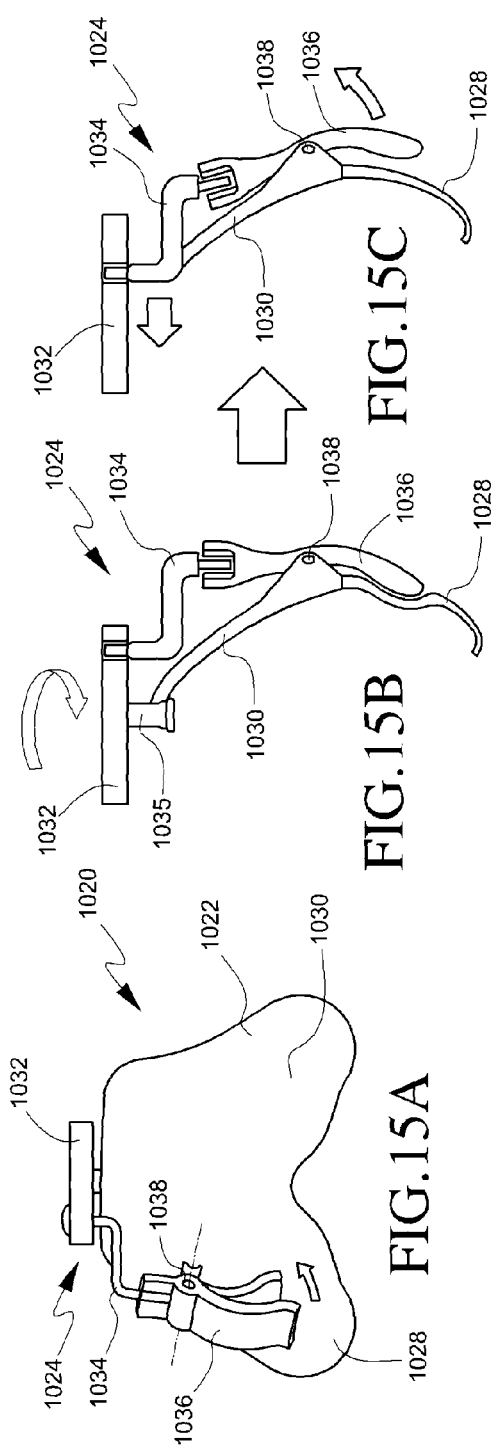
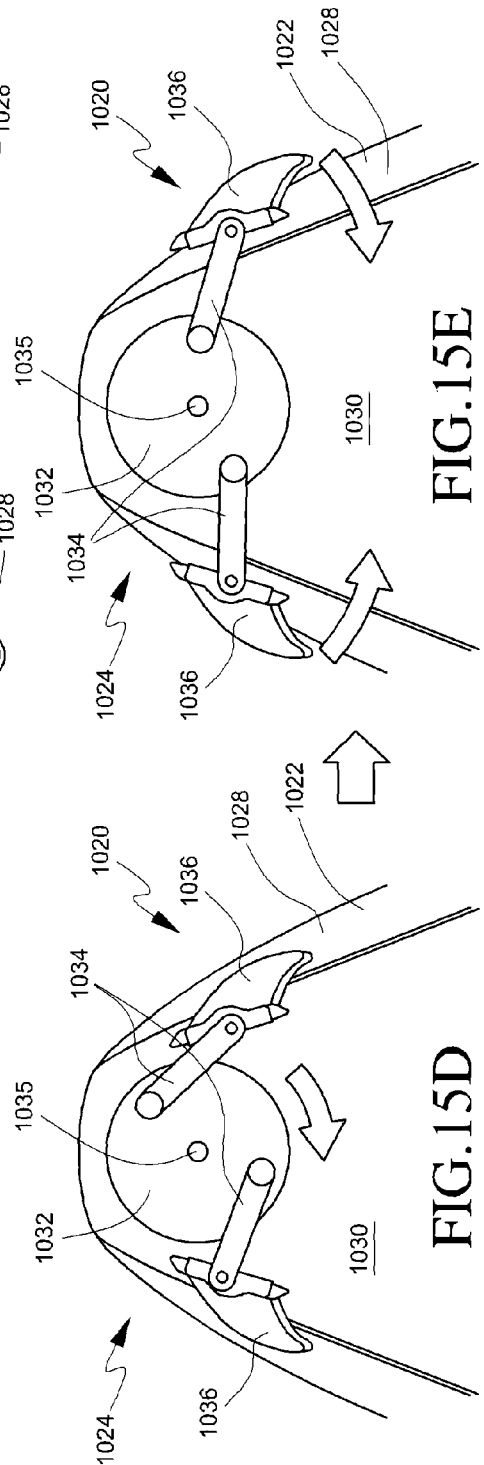

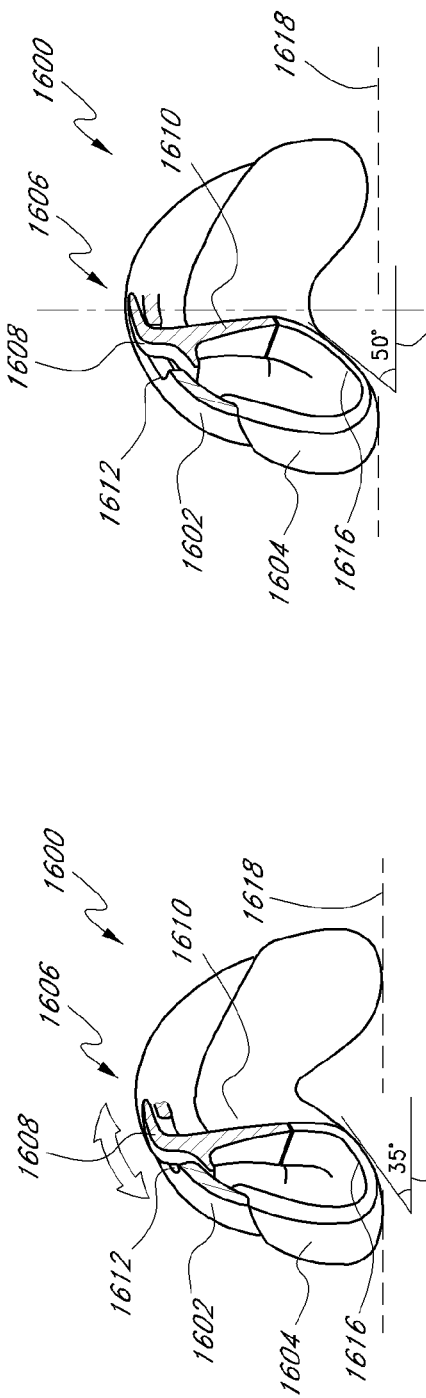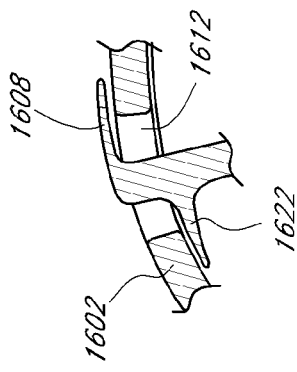
FIG.16B
FIG.16C
FIG.16A

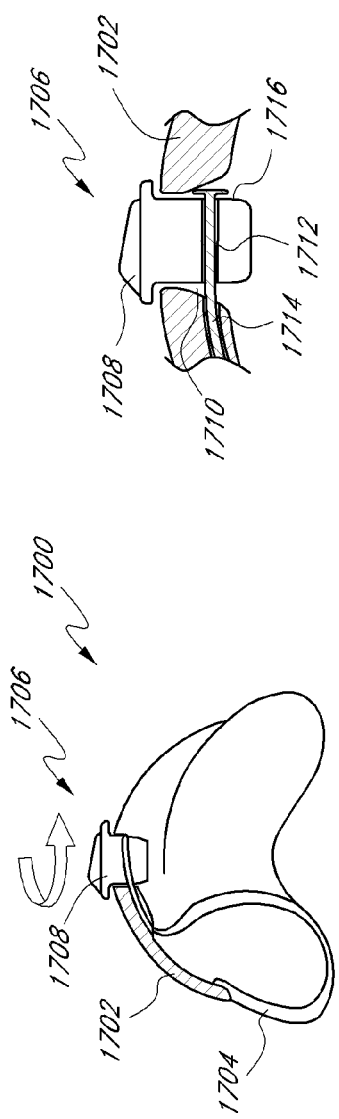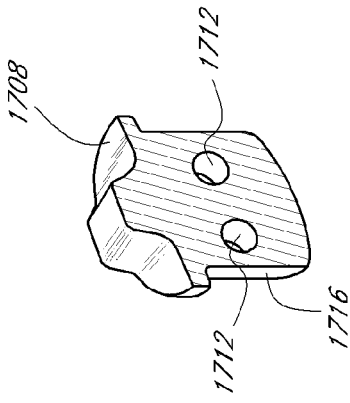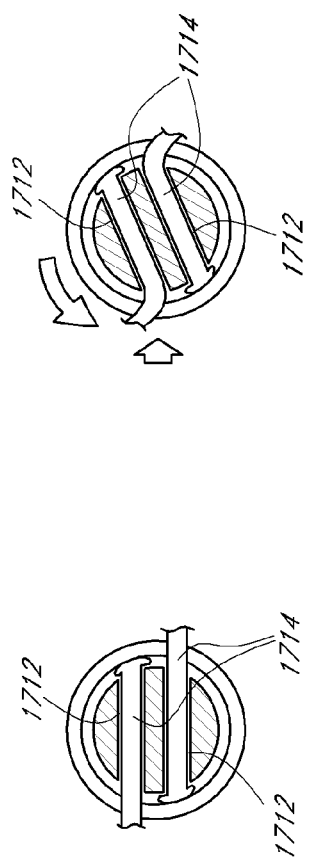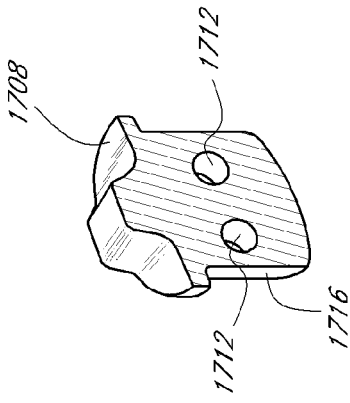
FIG.17E
FIG.17B
FIG.17D
FIG.17A
FIG.17C

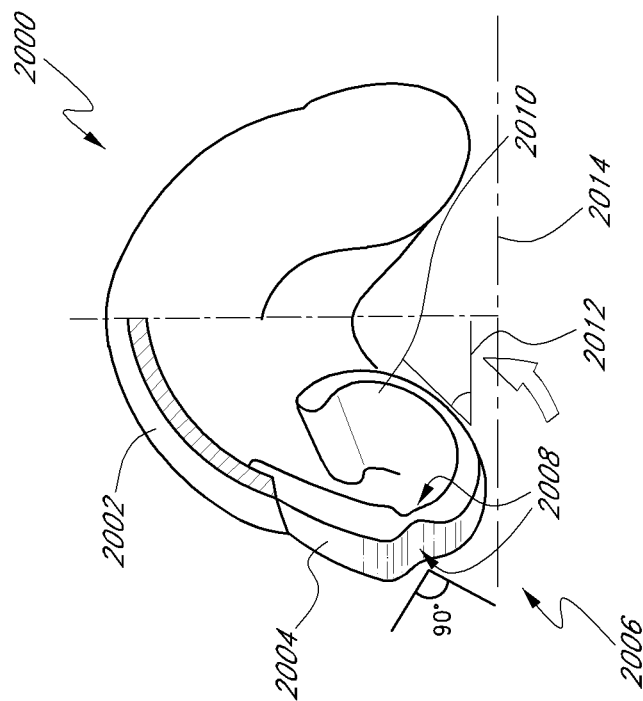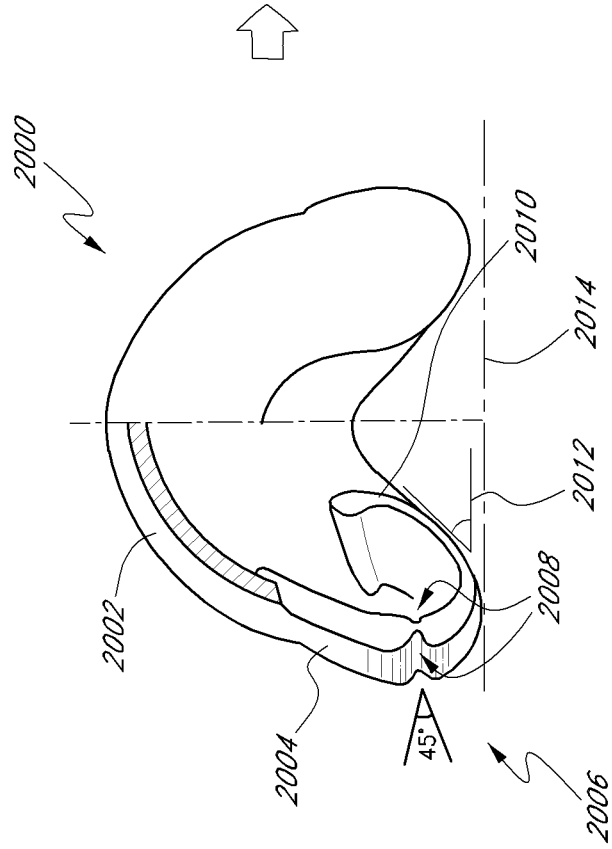
FIG.20B
FIG.20A

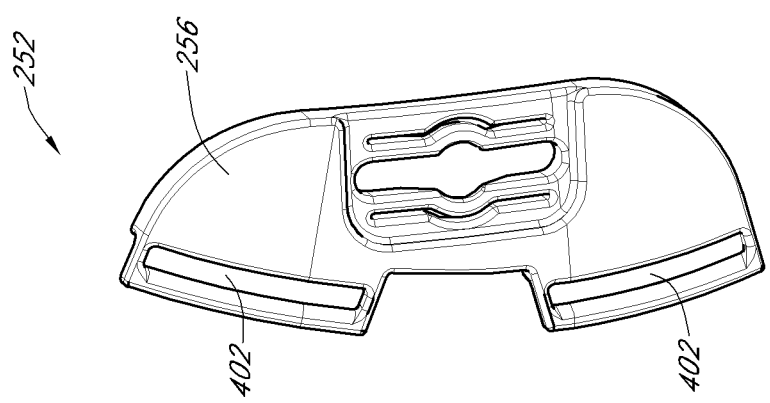
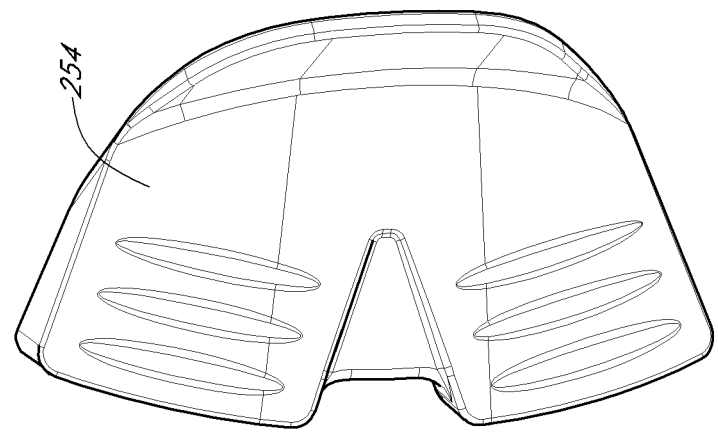
FIG. 32

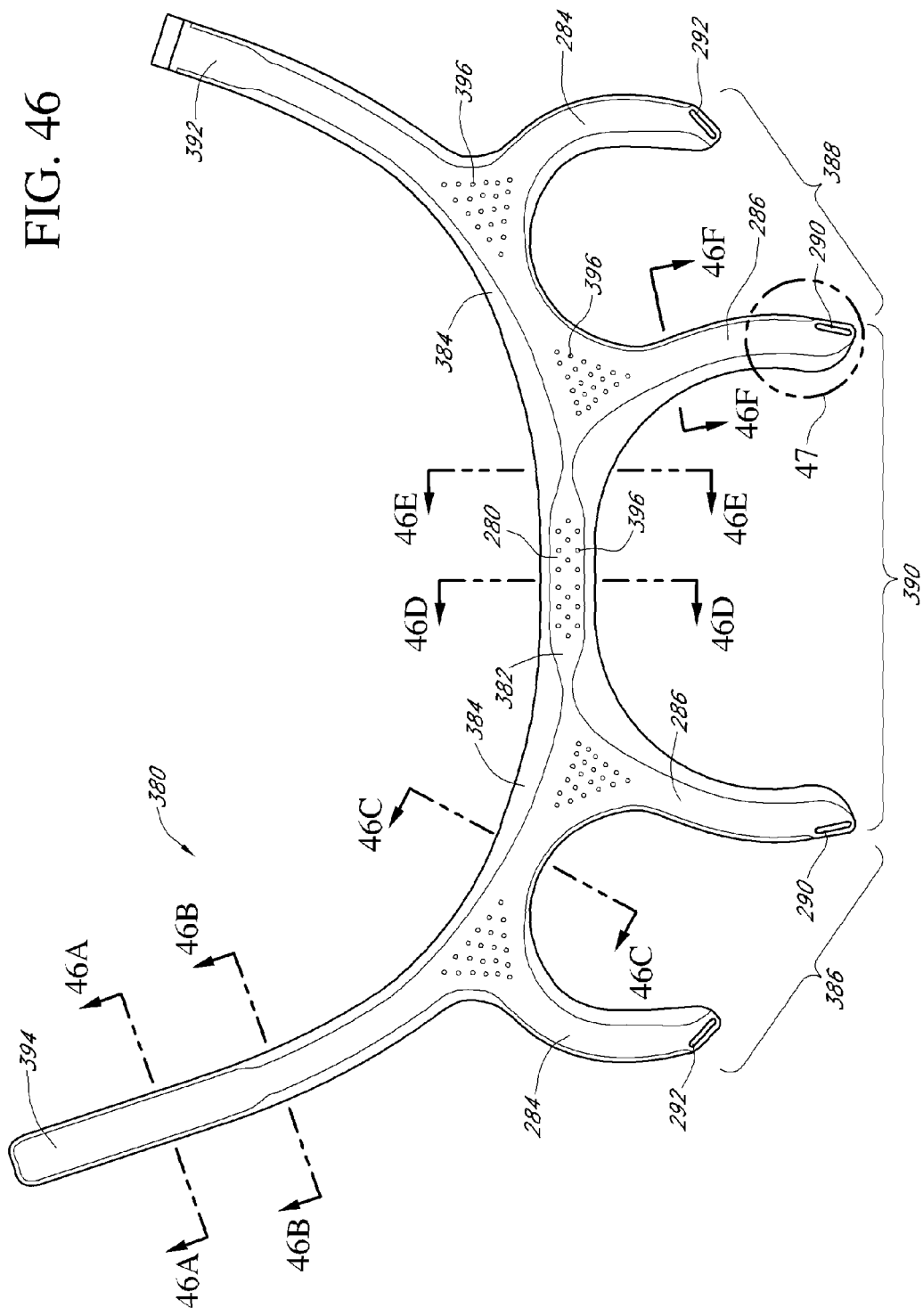

VALSALVA MASK

BACKGROUND OF THE INVENTION

Field of the Inventions

The present inventions generally relate to face masks that cover at least one of a nose and a mouth of a user to supply respiratory gas under positive pressure. More particularly, certain aspects of the present inventions relate to such masks that have an improved nasal seal portion.

Description of the Related Art

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user.

Such full face masks commonly are secured to a head of the user with headgear. In order to sufficiently reduce leakage, the headgear typically is tightened, which results in an elevated pressure being exerted on a bridge of a user's nose. As the headgear is tightened, the seal typically applies a progressively increasing load on the bridge of the nose. The pressure can be a source of discomfort and, in some circumstances, can lead to pressure sores over time. Looser fitting headgear may provide greater patient comfort, but air leakage can occur. In particular, loose fitting and in some cases even tight fitting masks can leak air around the portion of the mask near the user's tear ducts and nasal bridge.

SUMMARY OF THE INVENTIONS

It is an object of the present disclosure to provide one or more constructions and/or methods that will at least go some way towards improving on the above or that will at least provide the public or the medical profession with a useful choice.

Accordingly, an interface is provided for use in providing positive pressure respiratory therapy. The interface comprises a mask assembly. The mask assembly comprises a mask seal, a mask base that can be removably or permanently connected to the mask seal, and a seal adjustment mechanism. The seal adjustment mechanism can provide and control a lateral force to compress the seal against the user's nasal bone without applying additional pressure to the user's nasal bridge. In some configurations, the mask assembly may further comprise a headgear assembly. A connection port assembly may also be provided independently, attached to, or integrated with the mask base.

In one configuration an interface for use in providing positive pressure respiratory therapy comprises: a mask assembly comprising a mask seal and a mask base that is removably connected to the mask seal; a seal adjustment mechanism coupled to the mask base and configured to compress the mask seal primarily in a lateral direction across a width of the mask assembly; a headgear assembly comprising a pair of upper straps and a pair of lower straps, one of the pair of upper straps and one of the pair of lower straps being connected to a first clip, another of the pair of upper straps and another of the pair of lower straps being connected to a second clip, the first clip and the second clip being detachably securable to the mask base such that the clips are brought into engagement with the mask base by moving in a direction substantially normal to a strap tensile force direction; and a connection port assembly comprising an elbow terminating in a ball shaped member, the ball shaped member being sized and configured to be held within a wall of the mask base.

In one configuration, a mask assembly comprising a mask seal, the mask seal, a mask base, and a mask seal adjustment mechanism, the mask seal adjustment mechanism configured to adjust the distance between opposite walls of the mask seal. In one configuration, the mask seal adjustment mechanism comprises a dial coupled to a screw and a cage, the screw positioned within a thread of a cage, the cage having two arms that contact the mask seal, wherein rotating the dial causes the cage to move towards the mask base and squeeze the seal inwardly to decrease the distance between the opposite walls of the mask seal engaged by the cage. In one configuration, the cage defines a cavity and the mask seal is positioned at least partially within the cavity.

In one configuration, the mask seal adjustment mechanism comprises a swing arm pivotably coupled to the mask base, the swing arm comprising a lift bar and first and second ends, wherein lifting the lift bar lowers the first and second ends to compress opposite walls of the mask seal and to decrease a distance between the opposite walls of the mask seal.

In one configuration, the swing arm further comprises first and second pads attached to the first and second ends, respectively, the first and second pads configured to contact and squeeze opposite walls of the mask seal when the lift bar is raised.

In one configuration, the mask seal adjustment mechanism further comprises a ratchet configured to retain the lift bar in a desired position with respect to the mask base. In one configuration, the mask seal adjustment mechanism further comprises a dial and cog configured to retain the lift bar in a desired position with respect to the mask base. In one configuration, the mask seal adjustment mechanism comprises a malleable strip that is fixed to the mask seal. In one configuration, the malleable strip is fixed to the mask seal at the malleable strips end regions.

In one configuration, the mask seal adjustment mechanism comprises a T-piece swing arm coupled to the mask base at first and second pivots, the T-piece swing arm comprising a laterally-extending section configured to attach to a headgear assembly and a two compression arm positioned closer to the pivots than the laterally-extending section, the compression arms extending posteriorly towards the mask seal, wherein tension applied to the laterally-extending section rotates the T-piece swing arm about the pivots and causes the compression arms to squeeze and decrease the distance between opposite sides of the mask seal.

In one configuration, the mask seal adjustment mechanism comprises a drum vice, the drum vice comprising a finger wheel, a screw coupled to the finger wheel, and compression arms attached to opposite ends of the screw, wherein rotating the finger wheel rotates the screw which turns within a thread of the compression arms and moves the compression arms towards each other, wherein the moving compression arms compress and decrease the distance between opposite sides of the mask seal. In one configuration, the screw comprises a double threaded screw.

In one configuration, the mask seal adjustment mechanism comprises a dial, a cam coupled to the dial, and two rocker arms pivotably attached to the mask base, wherein turning the dial rotates the cam and causes the cam to lift first ends of the rocker arms, the rocker arms being substantially L-shaped such that as the cam lifts the first ends of the rocker arms, second ends of the rocker arms drum compress and decrease the distance between opposite sides of the mask seal.

In one configuration, the mask seal adjustment mechanism comprises a dial having a geared surface, a screw having a screw head configured to engage the geared surface and a threaded shaft, two paddles, the paddles comprising gear teeth at one end and configured to engage the threaded shaft, the paddles further comprising arms that extend to compression ends, wherein rotating the dial about a first axis turns the screw about a second axis, the second axis being perpendicular to the first axis, and wherein the screw rotates the paddles about third and fourth axes, the third and fourth axes being parallel to each other and the first axis, wherein rotating the paddles moves the arms and compression ends towards each other and decreases the distance between opposite sides of the mask seal between the compression ends.

In one configuration, the mask seal adjustment mechanism comprises: a dial positioned within a threaded opening in the mask base and having an external thread and an internal, tapered channel; and two compression arms having posteriorly-projection portions that extend into the tapered channel and anteriorly-projecting portions that extend along opposite sides of the mask seal, wherein rotating the dial within geared surface moves the two compressions arms towards each other and decreases the distance between opposite sides of the mask seal between the posteriorly-projecting portions.

In one configuration, the mask seal adjustment mechanism comprises two scissor arms that pinch opposite sides of the mask seal when the arms are rotated with respect to each other, wherein rotating the arms with respect to each other decreases the distance between opposite sides of the mask seal between the compression ends. In one configuration, the scissor arms extend horizontally, across a front surface of the mask base. In one configuration, the scissor arms extend vertically, across a top surface of the mask base.

In one configuration, the mask seal adjustment mechanism comprises two lugs attached to the mask seal and configured to receive straps from a headgear assembly, the lugs extending beyond the outer surface of the mask seal and configured to compress the mask seal and decrease the distance between opposite sides of the mask seal between the lugs when tension is applied to the straps. In one configuration, the lugs are molded as part of the mask seal.

In one configuration, the mask seal adjustment mechanism comprises two buttons positioned within a channel defined by the mask base, and a ratcheting lever arm, the buttons having first ends, second ends, and ratcheting teeth configured to engage the ratcheting lever arm and retain the buttons in desired position, the second ends positioned at opposite sides of the mask seal, wherein pressing the first end of the buttons moves the second ends of the buttons towards each other, and decreases the distance between opposite sides of the mask seal between the buttons.

In one configuration, the mask seal adjustment mechanism comprises a dial; a first and second links coupled to the dial; and first and second paddles coupled to the first and second links; wherein the paddles are rotatably coupled to the mask base by first and second pins, and wherein turning the dial causes the links to push on proximal ends of the first and second paddles, wherein pushing the proximal ends rotates the paddles about the first and second pins and moves the paddles' distal ends towards each other and squeezes the mask seal such that the distance between opposite sides of the mask seal between the paddles' distal ends decreases as the dial is rotated.

A headgear assembly comprises a pair of upper straps and a pair of lower straps. One of the pair of upper straps and one of the pair of lower straps is connected to a first clip. Another of the pair of upper straps and another of the pair of lower straps is connected to a second clip. The first clip and the second clip are securable within the pockets of the mask base such that the clips are brought into engagement within the pockets by moving in a direction substantially normal to a strap tensile force direction.

In some configurations, the mask seal is a full face mask. In some configurations, the mask seal clip is integrated into the mask seal such that the mask seal clip is non-separable from the mask seal. In some configurations, the mask base is removably connected to the mask seal. In some configurations, the upper portion of the mask seal comprises an apex defined by a first wall and a second wall and the reinforcing component extends along at least a portion of the first wall and along at least a portion of the second wall. Preferably, the reinforcing component extends over the apex of the upper portion of the mask seal.

A mask assembly can comprise a mask seal. The mask seal comprises a nasal region and an oral region. The nasal region and the oral region are integrally formed. The nasal region is movable relative to the oral region such that forces exerted by the nasal region in multiple positions remain substantially constant while forces exerted by the oral region increase.

A mask assembly comprises a mask seal connected to a headgear assembly. The mask seal is configured to encircle a nasal bridge region and an oral region of a user. The mask seal comprises nonpleated means for applying a substantially constant force to the nasal bridge region while applying increasing forces to an oral region when the headgear assembly is tightened.

A mask assembly comprises a seal. The seal comprises a flange that engages a face of a user. The seal is removably connected to a mask base. The mask base comprises a first opening and a second opening. The first opening and the second opening receive a first clip and a second clip from an associated headgear assembly. The mask base further comprises a passageway positioned generally between the first opening and the second opening. The passageway is adapted to receive a breathing tube connector.

In some configurations, the mask assembly further comprises a mask seal clip that is connected to the mask seal and that is removably connected to the mask base. Preferably, the mask base overlies a substantial portion of the mask seal clip. More preferably, the mask base comprises a peripheral edge and at least one recess is defined along the peripheral edge of the mask base at a location that overlies the mask seal clip.

A mask assembly comprises a mask seal. The mask seal comprises a proximal flange adapted to contact a face of a user. The mask seal comprises a distal facing surface. A mask base comprises a peripheral edge and a cover surface extends from the peripheral edge. The mask base cover surface overlies at least a portion of the distal facing surface of the mask seal such that the mask base cover surface is spaced apart in a distal direction from the mask seal distal facing surface whereby the mask base cover surface and the mask seal distal facing surface provide an insulating effect to the mask assembly that reduces humidity rainout.

An interface for providing positive pressure air flow to a user can comprise a mask base and a mask seal removably connected to the mask base. The mask seal comprises a first sealing surface that is adapted to underlie a nose of a user and a second sealing surface that is adapted to extend over at least a fibro-fatty tissue of one or more alar of the nose of the user without wrapping over a tip of the nose of the user.

In some configurations, the first sealing surface is defined by an upper surface. A chamber can be defined within the seal member and an opening through the upper surface can be generally flush with the upper surface.

BRIEF DESCRIPTION OF THE DRAWINGS

These and other features, aspects and advantages of embodiments of the present invention will be described with reference to the following drawings.

FIGS. 4A-4H are views of an interface comprising a swing arm seal adjustment mechanism.

FIGS. 6A-6E are views of an interface comprising a T-piece swing arm seal adjustment mechanism.

FIGS. 7A-7B are views of an interface comprising a drum vice seal adjustment mechanism.

FIGS. 8A-8B are views of an interface comprising a cam and rocker seal adjustment mechanism.

FIGS. 9A-9E are views of an interface comprising a gear dial seal adjustment mechanism.

FIGS. 10A-10D are views of an interface comprising a taper dial seal adjustment mechanism.

FIGS. 11A-11G are views of an interface comprising a horizontal scissor seal adjustment mechanism.

FIGS. 12A-12H are views of an interface comprising a vertical scissor seal adjustment mechanism.

FIGS. 13A-13E are views of an interface comprising a lug assembly seal adjustment mechanism.

FIGS. 14A-14E are views of an interface comprising a ratcheting seal adjustment mechanism.

FIGS. 15A-15E are views of an interface comprising a dial and linkage seal adjustment mechanism.

FIGS. 16A-16C are views of an interface comprising a sliding seal adjustment mechanism.

FIGS. 17A-17E are views of an interface comprising a rotating seal adjustment mechanism.

FIGS. 20A-20B are views of an interface comprising a variable wall thickness adjustment mechanism.

FIG. 32 is an exploded view of the clip of FIG. 31.

FIGS. 46 and 46A-F are a perspective and various cross-sectional views of a backbone compatible with the headgear assembly of FIGS. 1 and 2.

DETAILED DESCRIPTION OF THE PREFERRED EMBODIMENT

Figure 1:
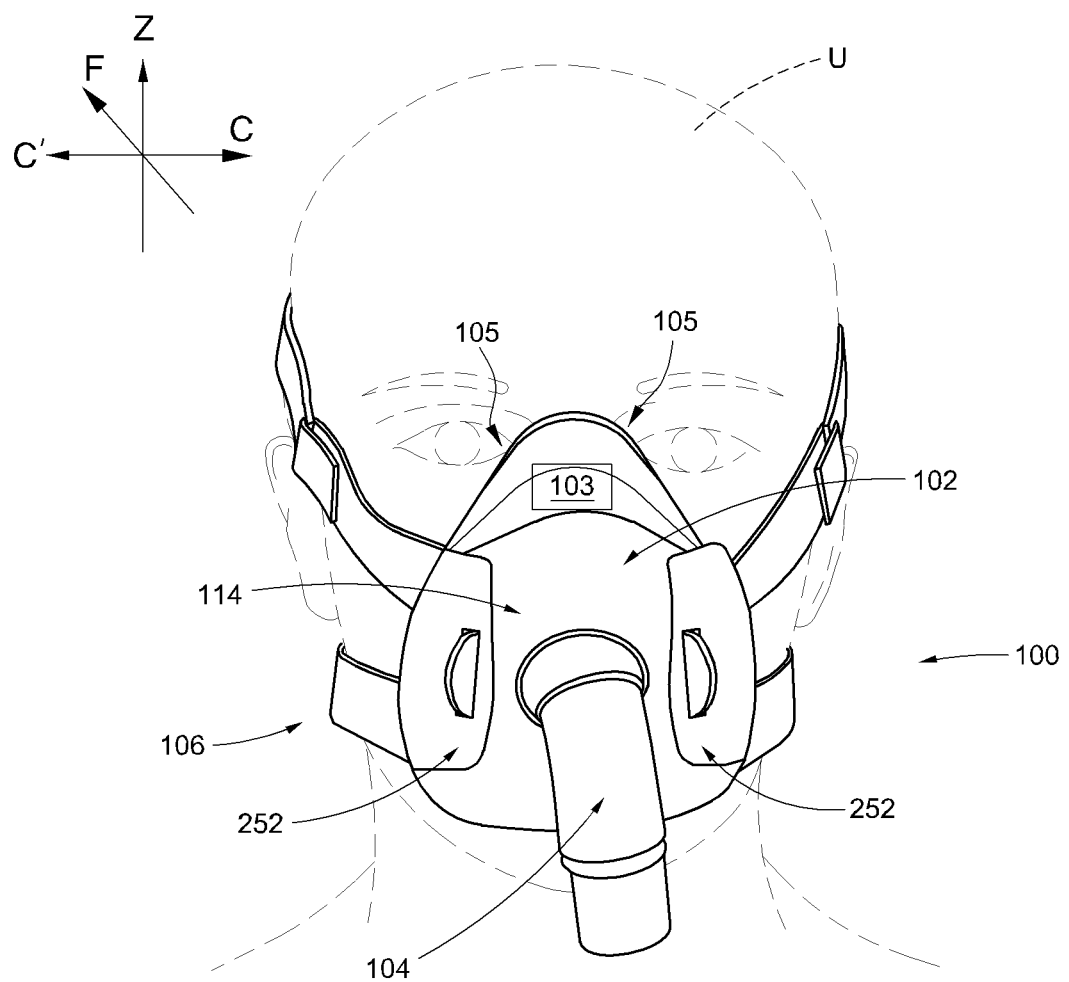
FIG. 1 is front view of a user wearing an interface that is arranged and configured in accordance with certain features, aspects and advantages of the present invention.
Figure 2:
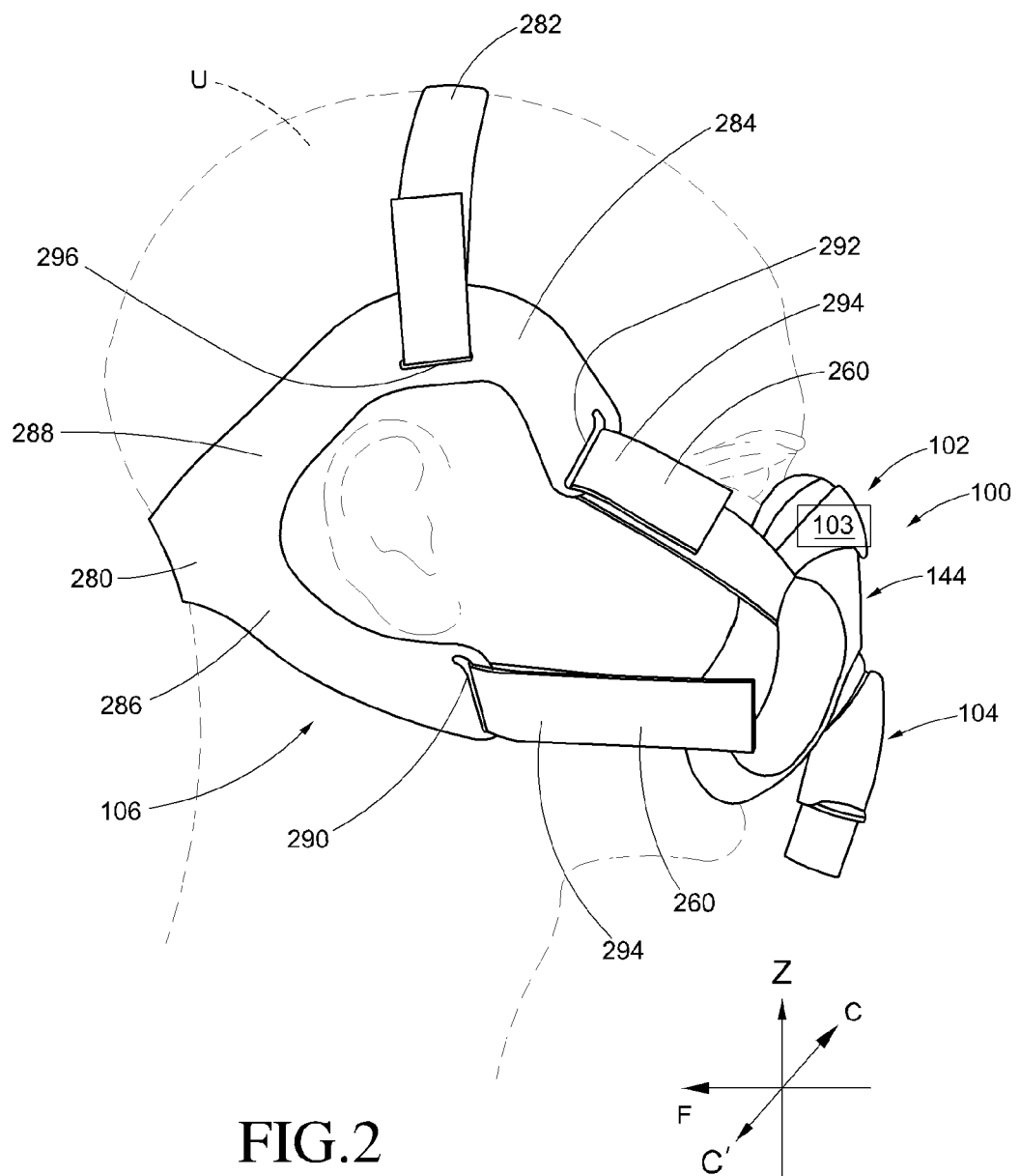
FIG. 2 is a side view of a user wearing the interface of FIG. 1.
Figure 3A:
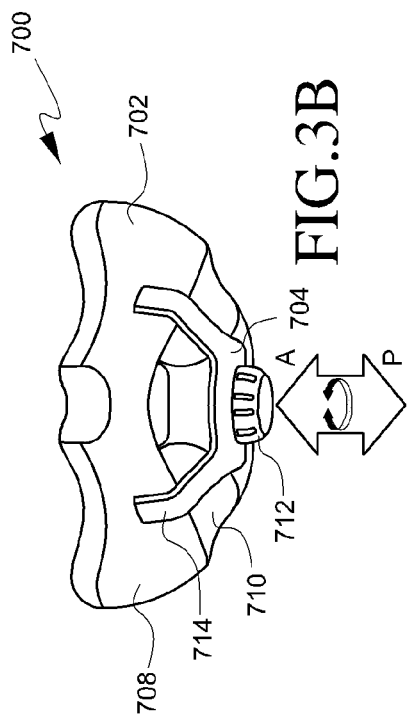
FIGS. 3A-3D are views of an interface comprising a dial and cage seal adjustment mechanism.
Figure 3B:
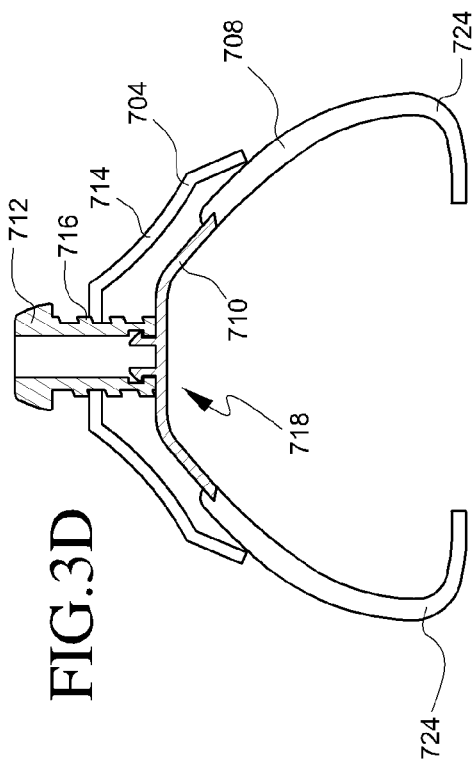
Figure 3C:
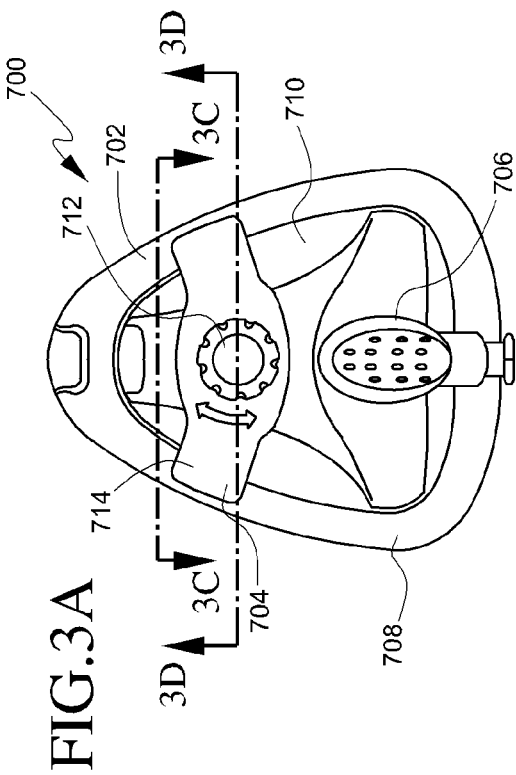
Figure 3D:
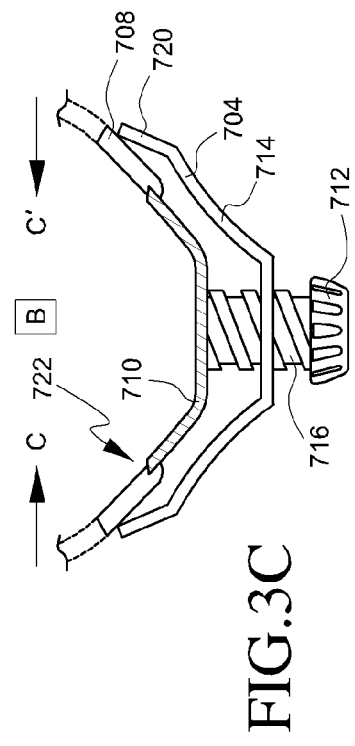

With reference initially to FIGS. 1 and 2, an interface 100 is shown in position on a user U. The interface 100 comprises an interface that can be used in the field of respiratory therapy. The interface 100 has particular utility with forms of positive pressure respiratory therapy. For example, the interface 100 can be used for administering continuous positive airway pressure ("CPAP") treatments. In addition, the interface 100 can be used with variable positive airway pressure ("VPAP") treatments and bi-level positive airway pressure ("BiPAP") treatments. The interface can be used with any suitable CPAP system.

The interface 100 can comprise any suitable mask configuration. For example, certain features, aspects and advantages of the present invention can find utility with nasal masks, full face masks, oronasal masks or any other positive pressure mask. The illustrated mask is a full face mask. The interface 100 generally comprises a mask assembly 102, a seal adjustment mechanism 103, a connection port assembly 104 and a headgear assembly 106. A mask seal 110 is attached to an edge of the mask assembly 102, and generally traverses the mask assembly's 102 perimeter. The headgear assembly 106 is used to secure the interface 100 to the patient's face. As the headgear assembly 106 is tightened (e.g., as its straps are pulled into tension), the interface 100 is pulled in an anterior direction F to compress the mask seal 110 against the user's face. However, due to typical irregularity in the contours of a user's face, the mask seal 110 may not adequately prevent air from escaping, or leaking, at all locations. In particular, the regions 105 of the mask seal 110 near the user's tear ducts can leak air. Air that escapes from inside the mask assembly 102 at the tear duct regions 105 can dry out the user's eyes, and provide general discomfort during use. A seal adjustment mechanism 103 can provide additional control over mask seal 110 compression and help eliminate air leakage, particularly around the tear duct regions 105.

The seal adjustment mechanism 103, shown in generic, block form in FIGS. 1 and 2, provides a user-controllable, compressive force along an axis transverse to the mask assembly's 100 vertical plane of symmetry, which is defined by the mask assembly's F and Z axes. In other words, the seal adjustment mechanism 103, provides a compressive force directed towards the side of the user's nasal bone, as indicated as directions C and C' in FIGS. 1 and 3. Any of a variety of mask configurations may be configured to comprise such seal adjustment mechanism 103, including, but not limited to, the particular mask configurations described below. In addition, any of a variety of seal adjustment mechanism configurations can help eliminate air leakage around the tear duct region 105 without putting excessive forces on the user's nasal bridge region.

For example, FIGS. 3A-3D illustrates one such configuration of an interface 700. The interface 700 comprises a mask assembly 702, a seal adjustment mechanism 704, a connection port assembly 706, and headgear (not shown). The mask assembly 702 comprises a mask seal 708 and a mask base 710. The mask seal 708 is removably attached to the mask base 710. The seal adjustment mechanism 704 includes a dial 712, cage 714 and threaded shaft 716. An interlock 718 couples the seal adjustment mechanism 704 to the mask base 710.

As the control dial 712 is rotated, threads on the threaded shaft 716 spin while engaged with an opening in the cage 714. Dial 712 rotation causes the cage 714 to advance anteriorly A (towards the mask base 710) or posteriorly P (away from the mask base 710), depending upon whether the dial 712 is rotated in a clockwise or counterclockwise direction. As the cage 714 moves towards the mask base 710, arms 720 push against the outside surface of the seal 708. Because the seal 708 is generally more flexible than the mask base 710, this movement of the arms 720 causes the flexible seal 708 to bend about the area where it is attached the more rigid mask base 710. As the seal 708 bends, the seal's distal ends 724 are pushed inwardly, towards the user's nasal bone B. The compressive forces applied by the seal 708 help prevent air leakage around the user's tear ducts.

Similarly, as the control dial 712 is rotated in the opposite direction, the cage 714 moves posteriorly, away from the user's face. As the cage 714 moves posteriorly, the cage's arms 720 move away from the seal 708, which allows the seal 708 to flex back to its original shape. By turning the control dial 712 the user may control the amount of compressive force provided by the seal adjustment mechanism 704 in order to achieve maximum comfort and to eliminate air leakage.

Figure 4B:
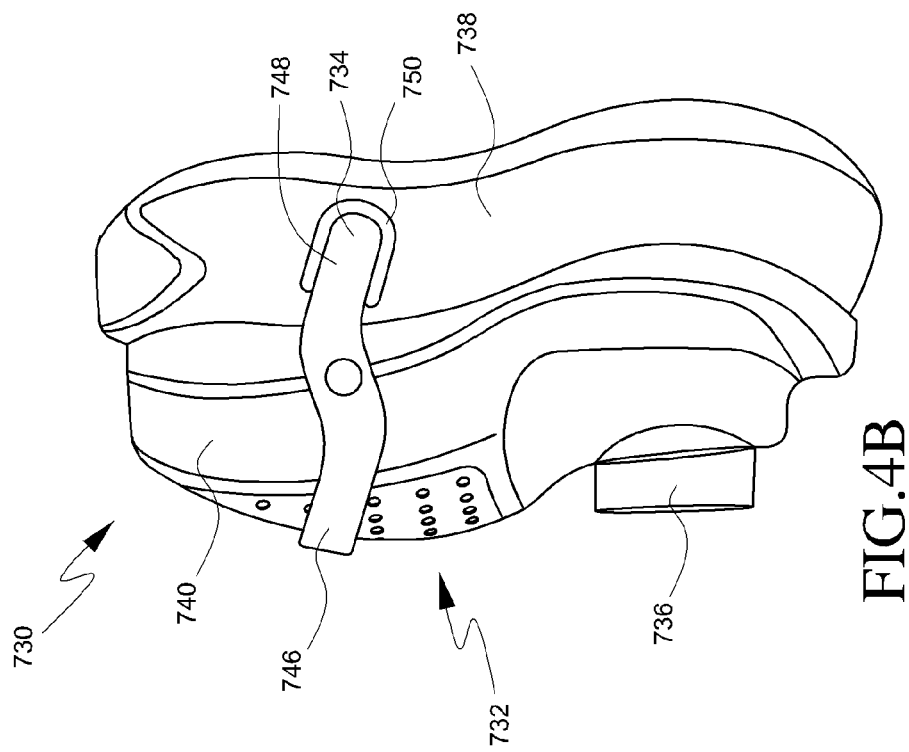
Figure 4A:
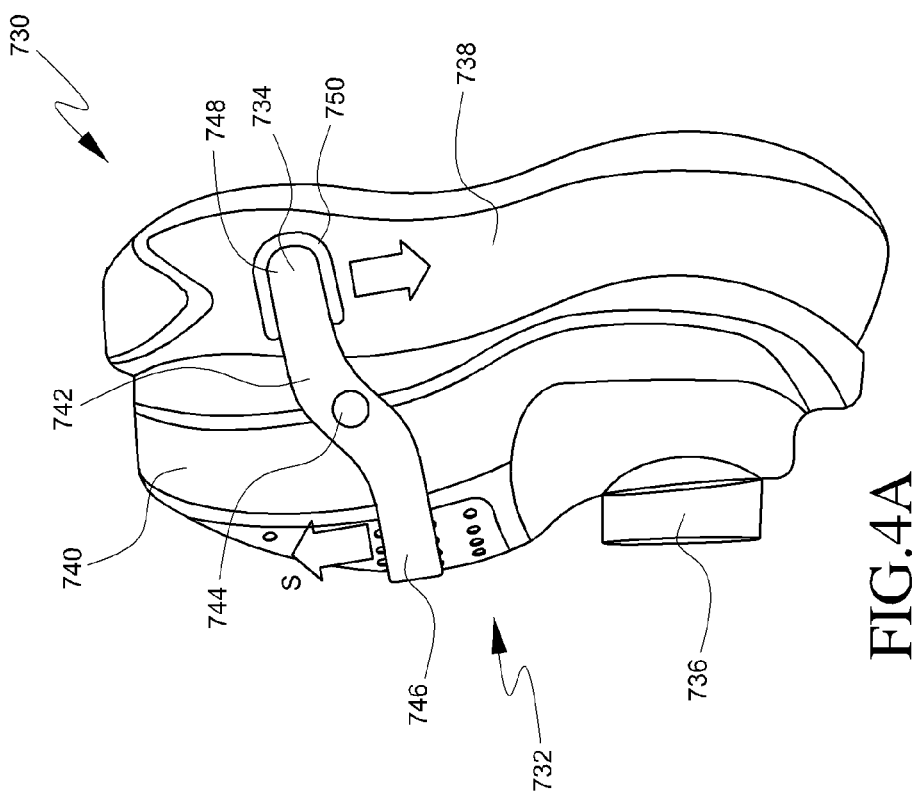

FIGS. 4A and 4B illustrate another configuration of an interface 730 configured to provide a lateral compressive force to reduce air leakage. The interface 730 includes a mask assembly 732, a seal adjustment mechanism 734, a connection port assembly 736, and headgear (not shown). The mask assembly 732 comprises a mask seal 738 and a mask base 740. The mask seal 738 is removably attached to the mask base 740. The seal adjustment mechanism 734 includes a lift bar 742 that is mounted to the mask base 740 at pivots 744 located at opposite sides of the mask assembly 732.

As a crossbar portion 746 of the lift bar 742 is raised (e.g., moved in the superior S direction towards the top of the interface 730), the ends 748 of the lift bar 742 move in the opposite direction. Pads 750 positioned at the lift bar 742 ends 748 compress or squeeze the seal 738 as the ends 748 are lowered. In some configurations, the lift bar 742 position is maintained as a result of frictional forces between the pads 750 and the seal 738. In other configurations, a control mechanism 752 is provided. For example, the configuration of FIGS. 4C-4E illustrate the interface 730 comprising a control mechanism 752 in the form of a ratchet 754. A tongue 756 formed on the crossbar portion 746 of the lift bar 742 mates with teeth 758 formed on the outside surface of the mask base 740. The ratchet 752 secures the crossbar portion 746 in the desired position. Similarly, the configuration of FIGS. 4F-4H illustrate the interface 730 comprising a control mechanism 752 in the form of a dial 760 and cog 762. The dial 760 is coupled to the cog 762 such that as the dial 760 is rotated the cog 762 spins in the same direction. Teeth 764 in the cog 762 engage with teeth 766 located along a wall of a cavity formed within the mask base 740. Turning the dial 760 thereby allows the user to control distance that the ends 748 of the lift bar 742 are moved, which in turn control the amount of compressive force is applied by the pads 750 against the mask seal 738. In this manner the user may control the amount of compressive force provided by the seal adjustment mechanism 734 in order to achieve maximum comfort and to eliminate air leakage.

Figure 5:
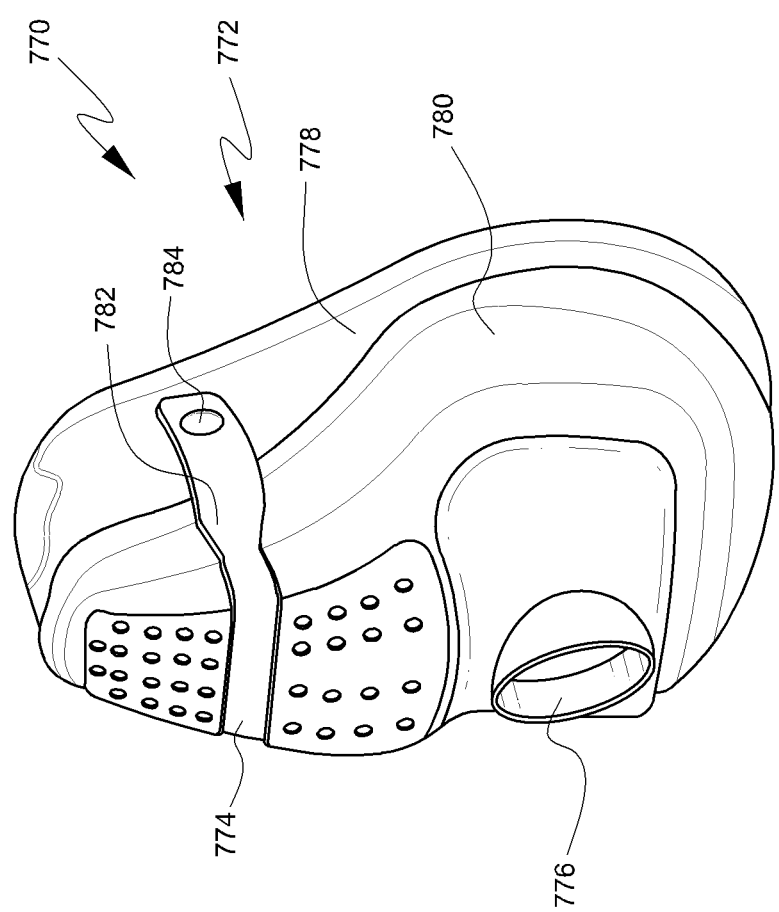
FIG. 5 is a front perspective view of an interface comprising a squeeze bar seal adjustment mechanism.

FIG. 5 illustrates another configuration of an interface 770 configured to provide a lateral compressive force to reduce air leakage. The interface 770 includes a mask assembly 772, a seal adjustment mechanism 774, a connection port assembly 776, and headgear (not shown). The mask assembly 772 comprises a mask seal 778 and a mask base 780. The mask seal 778 is removably attached to the mask base 780. The seal adjustment mechanism 774 includes a malleable strip 782 that is attached to the mask base 780 at attachment points 784.

The malleable strip 782 is formed from a malleable strip of material that can be easily shaped by squeezing, pushing, or pulling on the material. The malleable strip 782 may be formed from any suitable material, such as metal, an alloy, or plastic, including but not limited to, aluminum, copper, magnesium, gold, silver, tin, etc. The malleable strip 782 extends from one side of the mask seal to the other. In other configurations, the malleable strip 782 is embedded within the mask seal 778. The malleable 782 extends within a channel formed in the mask base 780. Pinching the malleable strip 782 at locations near or at the attachment points 784 causes the malleable strip 782 to apply and sustain a compressive force against the mask seal 778. In this manner the user may control the amount of compressive force provided by the seal adjustment mechanism 774 in order to achieve maximum comfort and to eliminate air leakage.

FIGS. 6A-6E illustrate another configuration of an interface 790 configured to provide a lateral compressive force to reduce air leakage. The interface 790 includes a mask assembly 792, a seal adjustment mechanism 794, a connection port assembly 796, and headgear 798 (partially shown in FIG. 6B). The mask assembly 792 comprises a mask seal 800 and a mask base 802. The mask seal 800 is removably attached to the mask base 802. The seal adjustment mechanism 794 includes a T-piece 804 that is attached to the mask base 802 at pivots 806.

The T-piece 804 comprises tabs 808 that squeeze and compress the mask seal 800 as the T-piece 804 is rotated about the pivots 806 from an open position (as shown in FIG. 6D) to a closed position (as shown in FIG. 6E). Rotation of the T-piece 804 is achieved by tensioning the headgear 798, as shown in FIG. 6B. The tabs 808 of the T-piece 804 are angled sufficiently inward with respect to the mask seal's 800 outer surface such that tension in the headgear 798 is translated into mask seal 800 compression. By adjusting the tension in the headgear's 798 straps, the user may control the amount of compressive force provided by the seal adjustment mechanism 794 in order to achieve maximum comfort and to eliminate air leakage.

FIGS. 7A and 7B illustrate another configuration of an interface 810 configured to provide a lateral compressive force to reduce air leakage. The interface 810 includes a mask assembly 812, a seal adjustment mechanism 814, a connection port assembly (not shown), and headgear (not shown). The mask assembly 812 comprises a mask seal 816 and a mask base 818. The mask seal 816 is removably attached to the mask base 818. The connection port assembly (not shown) attaches to the mask assembly 812 at an opening 820 in the mask base 818.

The seal adjustment mechanism 814 comprises a finger wheel 822, a double threaded screw 824, and adjustment arms 826 positioned at opposite ends of the double threaded screw 824. As the finger wheel 822 is rotated, the screw 824 spins and causes adjustment arms 826 to move inwardly (towards each other) or outwardly (away from each other), depending upon the direction of finger wheel 822 rotation. The adjustment arms 826 are positioned outside of respective portions of the mask seal 816, such that the mask seal 816 is compressed as the adjustment arms 826 are moved towards each other. Similarly, the compressive force acting upon the mask seal 816 is reduced as the adjustment arms 826 are moved away from each other. By rotating the finger wheel 822, the user may control the amount of compressive force provided by the seal adjustment mechanism 814 in order to achieve maximum comfort and to eliminate air leakage.

FIGS. 8A and 8B illustrate another configuration of an interface 830 configured to provide a lateral compressive force to reduce air leakage. The interface 830 comprises a mask assembly 832, a seal adjustment mechanism 834, a connection port assembly 836, and headgear (not shown). The mask assembly 832 comprises a mask seal 838 and a mask base 840. The mask seal 838 is removably attached to the mask base 840.

The seal adjustment mechanism 834 comprises a dial 842 coupled to a cam 844. The seal adjustment mechanism 834 also comprises L-shaped rocker arms 846 that are rotatably coupled to the mask assembly 832 at pivots 848. First ends of the rocker arms 846 are aligned with the cam 844 and second ends of the rocker arms 846 are aligned with the mask seal 838. Rotating the dial 842 causes the cam 844 to rotate and engage or disengage the first ends of the rocker arms 846 and push them upward and away from the dial 842. As the first end of the rocker arms 846 move away from the dial 842, the second ends of the rocker arms 846 are rotated towards each other about respective pivots 848. The second ends of the rocker arms 846 engage and compress the outside surface of the mask seal 838, thereby providing compressive force to improve sealing. By rotating the dial 842, the user may control the amount of compressive force provided by the seal adjustment mechanism 834 in order to achieve maximum comfort and to eliminate air leakage.

FIGS. 9A-9E illustrate another configuration of an interface 850 configured to provide a lateral compressive force to reduce air leakage. The interface 850 comprises a mask assembly 852, a seal adjustment mechanism 854, a connection port assembly (not shown), and headgear (not shown). The mask assembly 852 comprises a mask seal 858 and a mask base 860. The mask seal 858 is removably attached to the mask base 860. The connection port assembly (not shown) attaches to the mask assembly 852 at an opening 862 in the mask base 860.

The seal adjustment mechanism 854 comprises a gear dial assembly formed from a dial 864, a screw 866, and two geared paddles 868. Dial 864 is rotated to turn the threads on the screw 866. The rotating screw 866 engages the geared ends of the paddles 868 and causes the paddles 868 to rotate about respective pivots 870. Arms 872 attached to the paddles 868 comprise compression portions 874 at their distal ends. The compression portions 874 rotate into and compress the mask seal 858 as the dial 864 is rotated. By rotating the dial 864, the user may control the amount of compressive force provided by the seal adjustment mechanism 854 in order to achieve maximum comfort and to eliminate air leakage.

FIGS. 10A-10D illustrate another configuration of an interface 880 configured to provide a lateral compressive force to reduce air leakage. The interface 880 comprises a mask assembly 882, a seal adjustment mechanism 884, a connection port assembly (not shown), and headgear (not shown). The mask assembly 882 comprises a mask seal 888 and a mask base 890. The mask seal 888 is removably attached to the mask base 890. The connection port assembly (not shown) attaches to the mask assembly 882 at an opening 892 in the mask base 890.

The seal adjustment mechanism 884 comprises a taper dial assembly formed from a dial 894 and two arms 896. The dial 894 comprises a threaded outer surface 898 and a tapered internal channel 900. The dial 894 is positioned within a thread 902 formed within or attached to the mask base 890. As the dial 894 is rotated within the thread 902, the dial 894 moves inward or outward with respect to the thread 902 and mask base 890. When the dial 894 moves inward, proximal end portions 904 of the arms 896 interface with the tapered internal channel 900, which causes the arms 896 to move towards each other. As the arms 896 move towards each other, the arms' distal end portions 906 compress the outer surface of the mask seal 888. Similarly, rotating the dial 894 in the opposite direction causes the dial 894 to move outward with respect to the mask base 890. As the dial 894 move outward, proximal end portions 904 of the arms 896 move away from each other, thereby reducing the compression of the outer surface of the mask seal 888. By rotating the dial 894, the user may control the amount of compressive force provided by the seal adjustment mechanism 884 in order to achieve maximum comfort and to eliminate air leakage.

FIGS. 11A-11G illustrate another configuration of an interface 910 configured to provide a lateral compressive force to reduce air leakage. The interface 910 comprises a mask assembly 912, a seal adjustment mechanism 914, a connection port assembly (not shown), and headgear (not shown). The mask assembly 912 comprises a mask seal 918 and a mask base 920. The mask seal 918 is removably attached to the mask base 920. The connection port assembly (not shown) attaches to the mask assembly 912 at an opening 922 in the mask base 920.

The seal adjustment mechanism 914 comprises a horizontal scissors assembly formed from first and second scissor arms 924. The first and second scissor arms 924 connect to each other at a pivot 926 and extend from the rear toward the front of the mask assembly 912. The diameter of the pivot 926 is aligned with a vertical axis V that bisects the mask assembly 912. As first ends 928 of the scissor arms 924 are pinched and moved towards each other, second ends 930 of the scissor arms 924 are advanced towards each other, as well. The second ends 930 comprise enlarged regions configured to engage and compress the mask seal 918 towards the vertical axis V. By pinching the first ends 928 of the scissor arms 924, the user may control the amount of compressive force provided by the seal adjustment mechanism 914 in order to achieve maximum comfort and to eliminate air leakage.

FIGS. 12A-12G illustrate another configuration of an interface 940 configured to provide a lateral compressive force to reduce air leakage. The interface 940 comprises a mask assembly 942, a seal adjustment mechanism 944, a connection port assembly (not shown), and headgear 946 (partially shown). The mask assembly 942 comprises a mask seal 948 and a mask base 950. The mask seal 948 is removably attached to the mask base 950.

The seal adjustment mechanism 944 comprises a vertical scissor assembly formed from first and second scissor arms 952. The first and second scissor arms 952 connect to each other at a pivot 954 and extend from a position above the top of the mask assembly 942 toward the bottom of the mask assembly 942. The pivot 954 includes a geared interface in the configurations of FIGS. 12C-12E such that the rotation of one scissor arm 952 about the pivot 954 rotates the other scissor arm 952 about the pivot 954, as well. In the configuration of FIGS. 12F-12H, the pivot 954 does not include a geared interface such that the scissor arms 952 are independently movable with respect to the pivot 954.

Straps of the headgear assembly 946 attach to slots formed in at the upper ends of the scissor arms 952. As the straps are drawn into tension, the upper ends of the scissor arms 952 are pulled away from each other. Rotation of the upper ends of the scissor arms 952 away from each other causes the lower ends of the scissor arms 952 to rotate towards each other. As the lower ends of the scissor arms 952 rotate towards each other, they pinch and compress the mask seal (as shown in FIG. 12B). The lower ends of the scissor arms 952 are adhered to the outside surface of the mask seal 948. In other configurations, the mask base 950 extends in the upward direction, and the pivot 954 is attached to the mask base 950. By tightening the straps of the headgear assembly 946, the user may control the amount of compressive force provided by the seal adjustment mechanism 944 in order to achieve maximum comfort and to eliminate air leakage.

FIGS. 13A-13E illustrate another configuration of an interface 960 configured to provide a lateral compressive force to reduce air leakage. The interface 960 comprises a mask assembly 962, a seal adjustment mechanism 964, a connection port assembly (not shown), and headgear 966 (partially shown). The mask assembly 962 comprises a mask seal 968 and a mask base 970. The mask seal 968 is removably attached to the mask base 970. The connection port assembly (not shown) attaches to the mask assembly 962 at an opening 972 in the mask base 970.

The seal adjustment mechanism 964 comprises one or more lugs 974 attached to or integrally formed with the mask seal 968. Straps of the headgear assembly 966 pass through openings in the lugs 974 and attach to the mask base 970 at attachment points 976. In some configurations, the attachment points 976 are also lugs, as illustrated in FIGS. 13A-13E. In other configurations, the attachment points 976 comprise clips, snaps, hook and loop fabric, etc.

Figure 13E:
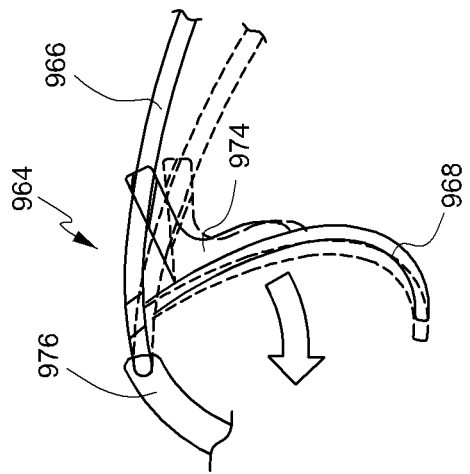
Figure 13D:
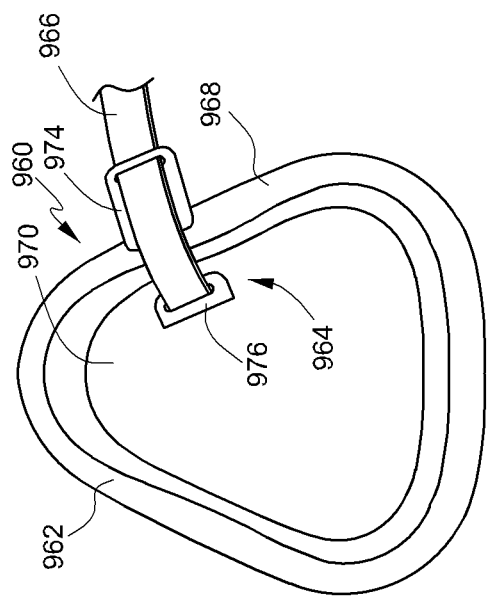

As the headgear 966 straps are tensioned around the user's head, the lugs 974 are compressed into the mask seal 968, as shown in FIGS. 13C and 13E. The mask seal 968 rotates about its connection to the mask base 970 and compresses against the user's skin, typically along the side of the user's nose, in the direction of the side of the nasal bone. In this manner, tensioning the straps in a first direction (posteriorly, towards the rear of the user's head) results in a transverse compressive force (laterally, inwardly, towards the center of the user's nose). By tightening the straps of the headgear assembly 966, the user may control the amount of compressive force provided by the seal adjustment mechanism 964 in order to achieve maximum comfort and to eliminate air leakage.

FIGS. 14A-14E illustrate another configuration of an interface 980 configured to provide a lateral compressive force to reduce air leakage. The interface 980 comprises a mask assembly 982, a seal adjustment mechanism 984, a connection port assembly (not shown), and headgear assembly (not shown). The mask assembly 982 comprises a mask seal 988 and a mask base 990. The mask seal 988 is removably attached to the mask base 990. The connection port assembly (not shown) attaches to the mask assembly 982 at an opening 992 in the mask base 990.

The seal adjustment mechanism 984 comprises a ratchet mechanism and button assembly configured to apply pressure on opposite sides of the mask seal 988. The seal adjustment mechanism 984 comprises a button 994 that slides within a channel of the mask assembly 982. As the user presses against the outside surface of the button 994, the inside surface of the button 994 presses into the side of the mask seal 988, thereby compressing the seal 988 laterally, for example, against the user's nasal bone. A ratchet mechanism 996 (as shown in FIG. 14D) secures the button 994 in position, as the button's teeth 998 engage an end of a lever arm 1000. The lever arm 1000 attaches to the mask base 990 at a pivot 1002, and rotates about the pivot 1002 to release the button's teeth 998 when pressed. A spring 1004 positioned within the button 994 biases the button 994 in an outward direction. The outward bias provided by the spring 1004 allows the button 994 to pop out and release compressive forces applied to the mask seal 988 when the lever arm 1000 is pressed.

Another configuration of a ratchet mechanism 1006 is illustrated in FIG. 14E. The ratchet mechanism 1006 also includes a button 1008 and a linkage assembly 1010. Pressing the button 1008 compresses the mask seal 988 laterally, for example, against the user's nasal bone. Teeth in the button 1008 engage the distal end of the linkage assembly 1010 and hold the button 1008 in position. Pressing the proximal end of the linkage assembly 1010 releases the teeth of the button 1008 from the linkage assembly's distal end. When released the button 1008 moves back to its resting position, which releases the pressure applied by the button 1008 against the mask seal 988. In some configurations, the ratchet mechanism 1006 does not include a spring. Instead, the natural tendency of the mask seal 988 to revert to its noncompressed state enables the button 1008 to move outwardly to its open position when the proximal end of the linkage assembly 1010 is pressed. By pressing on the buttons, the user controls the amount of compressive force provided by the seal adjustment mechanism 984 in order to achieve maximum comfort and to eliminate air leakage.

FIGS. 15A-15E illustrate another configuration of an interface 1020 configured to provide a lateral compressive force to reduce air leakage. The interface 1020 comprises a mask assembly 1022, a seal adjustment mechanism 1024, a connection port assembly (not shown), and a headgear assembly (not shown). The mask assembly 1022 comprises a mask seal 1028 and a mask base 1030. The mask seal 1028 is removably attached to the mask base 1030.

The seal adjustment mechanism 1024 comprises a dial 1032, linkage 1034, and paddles 1036. The dial 1032 is secured to mask base 1030 via a pivot 1035. Proximal ends of the linkage are attached to the dial 1032 at openings within the dial 1032. The openings 1032 are larger than the diameters of the linkage proximal ends, such that linkage freely rotates within the openings as the dial is rotated about the pivot 1035.

The distal ends of the linkage 1034 fit within receptacles located at the proximal ends of the paddles 1036. The paddles 1036 are secured to the mask base 1030 at pivots 1038. The distal ends of the paddles 1036 are comprise enlarged contact portions configured to compress the mask seal 1028.

As the dial 1032 is rotated, the linkage length changes from a short configuration (as shown in FIGS. 15C and 15D) to a long configuration (as shown in FIGS. 15B and 15 E). In the short configuration, the linkage arms pull the proximal ends of the paddles 1036 towards each other and the dial 1032. As the proximal ends of the paddles 1036 are pulled towards each other and the dial 1032, the paddles 1036 rotate about respective pivots 1038, such as pins 1038, and the distal ends of the paddles 1036 move apart and away from each other. Pressure applied to the mask seal 1038 is released as the paddles 1036 move apart.

To compress the mask seal 1038, the dial 1032 is rotated to bring the linkage length into the long configuration. In the long configuration, the linkage arms push the proximal ends of the paddles 1036 outward and away from each other. The paddles 1036 rotate about their respective pivots 1038 to bring their distal ends closer towards each other. The paddle 1036 distal ends compress the mask seal 1038 in a lateral direction, for example, inward, toward the user's nasal bone. By rotating the dial 1032, the user controls the amount of compressive force provided by the seal adjustment mechanism 1024 in order to achieve maximum comfort and to eliminate air leakage.

FIGS. 16A-16C illustrate one embodiment of a mask assembly 1600 configured to provide a lateral compressive force against a user's nose in order to reduce air leakage. The mask assembly 1600 includes a housing (sometimes referred to herein as a mask base) 1602 and a seal 1604. The mask seal 1604 is removably attached to the mask base 1602. The mask assembly 1600 also includes a seal adjustment mechanism 1606. The mask assembly 1600 is compatible with any of the interfaces described herein, and may be provided with a connection port assembly (not shown) and/or a headgear assembly (not shown).

The seal adjustment mechanism 1606 comprises a slider 1608, which in the illustrated embodiment, is formed as an end portion 1610 of the mask seal 1604. The slider 1608 may be integrally formed with the mask seal 1604, or may be attached to the mask seal 1604. The slider 1608 and/or end portion 1610 may be made from a harder material than the mask seal 1604. For example, in one embodiment, the slider 1608 is formed from a harder grade of silicone than the remaining portion of the mask seal 1604.

The slider 1608 extends through a channel 1612 in the mask base 1602. Moving the slider 1608 within the channel 1612 adjusts the seal geometry around the user's side nose bridge. For example, in one embodiment, the inclination angle 1614 between the seal side nose bridge portion 1616 and the end plane 1618 of the seal 1604 increases or decreases depending upon the distance and direction that the slider 1608 is moved. In one embodiment, adjusting the slider 1608 from a first position, as shown in FIG. 16A to a second position, as shown in FIG. 16B, causes the inclination angle 1614 to adjust from about 35° (as shown in FIG. 16A) to about 50° (as shown in FIG. 16B). In other embodiments, the inclination angle 1614 is adjustable between about 20° and about 70°, between about 27° and about 60°, or between about 40° and about 45°. As the inclination angle 1614 is increased, the seal side nose bridge portion 1616 applies less pressure against the side of the user's nose. As the inclination angle 1614 in decreased, the seal side nose bridge portion 1616 applies greater pressure against the side of the user's nose. By adjusting the slider 1608, the user controls the amount of compressive force provided by the seal adjustment mechanism 1606 in order to achieve maximum comfort and to eliminate air leakage.

The slider 1608 can include a control 1620 to facilitate manipulation by a user. The slider 1608 can also include a tang 1622 to help maintain the slider 1608 in the desired position with respect to the base 1602 once adjusted. The tang 1622 can be configured to contact an inside surface of the base 1602. In one embodiment, frictional forces between the tang 1622 and the base 1602 maintain the slider 1608 in the desired position. In other embodiments, the tang 1622 includes a ratcheting mechanism that interfaces with a corresponding structure on the mask base 1602.

FIGS. 17A-17E illustrate one embodiment of another mask assembly 1700 configured to provide a lateral compressive force against a user's nose in order to reduce air leakage. The mask assembly 1700 includes a mask base 1702 and a mask seal 1704. The mask seal 1704 is removably attached to the mask base 1702. The mask assembly 1700 also includes a seal adjustment mechanism 1706. The mask assembly 1700 is compatible with any of the interfaces described herein, and may be provided with a connection port assembly (not shown) and/or a headgear assembly (not shown).

The seal adjustment mechanism 1706 comprises a dial 1708, which in the illustrated embodiment, is positioned within an opening 1710 of the mask base 1702. The dial 1708 is configured to rotate within the opening 1710. The dial 1708 includes one or more channels 1712, through which an end portion 1714 of the seal 1704 extends. In the illustrated embodiment, the dial 1708 includes two channels 1712. An end portion 1714 extends through each of the channels 1712. In some embodiments, the end portions 1714 are integrally formed with the seal 1704. In other embodiments, the end portions 1714 are attached to the seal 1704. For example, in some embodiments, the end portions 1714 comprise one or more cables, wires, or other flexible member.

As the dial 1708 is rotated within the opening 1710, the end portions 1714 wind (or unwind, depending upon the direction of rotation) around the dial's outside surface 1716. As the end portions 1714 wind around the dial's outside surface 1716, the seal 1704 is pulled upward, in tension, towards the dial 1708, which causes an inclination angle 1718 to increase. As the end portions 1714 are unwound from the dial's outside surface 1716, the seal 1704 is relaxed, which causes the inclination angle 1718 to decrease.

In one embodiment, rotating the dial 1708 from a first position, as shown in FIG. 17C to a second position, as shown in FIG. 17D, causes the inclination angle 1714 to adjust from about 35° to about 50°. In other embodiments, the inclination angle 1714 is adjustable between about 20° and about 70°, between about 27° and about 60°, or between about 40° and about 45°. As the inclination angle 1714 is increased, the seal side nose bridge portion 1720 applies less pressure against the side of the user's nose. As the inclination angle 1714 in decreased, the seal side nose bridge portion 1720 applies greater pressure against the side of the user's nose. By adjusting the dial 1708, the user controls the amount of compressive force provided by the seal adjustment mechanism 1706 in order to achieve maximum comfort and to eliminate air leakage.

FIGS. 18A-18D illustrate another embodiment of a mask assembly 1800 configured to provide a lateral compressive force against a user's nose in order to reduce air leakage. The mask assembly 1800 includes a mask base 1802 and a seal 1804. The mask seal 1804 is removably attached to the mask base 1802. The mask assembly 1800 also includes a seal adjustment mechanism 1806. The mask assembly 1800 is compatible with any of the interfaces described herein, and may be provided with a connection port assembly (not shown) and/or a headgear assembly (not shown).

The seal adjustment mechanism 1806 comprises a tab 1808, which in the illustrated embodiment, is formed as an end portion 1810 of the seal 1804. The tab 1808 may be integrally formed with the mask seal 1804, or may be attached to the mask seal 1804. The tab 1808 extends through an opening 1812 in the mask base 1802. The tab 1808 may include ratcheting features or teeth that engage the edge of the mask base opening 1812. The teeth of the tab 1808 hold the end portion 1810 at the desired position.

Figure 18A:
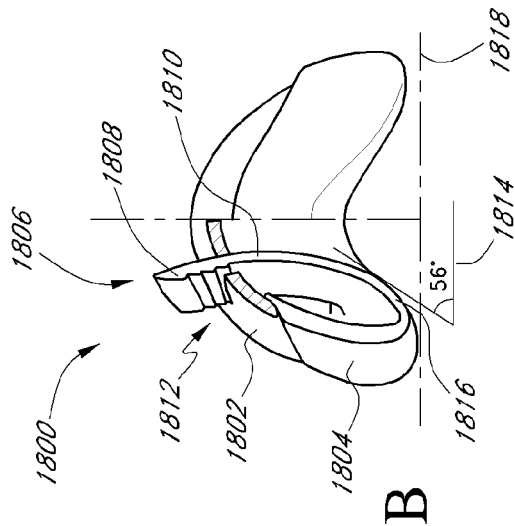
FIGS. 18A-18D are view of an interface comprising a tabbed seal adjustment mechanism.
Figure 18B:
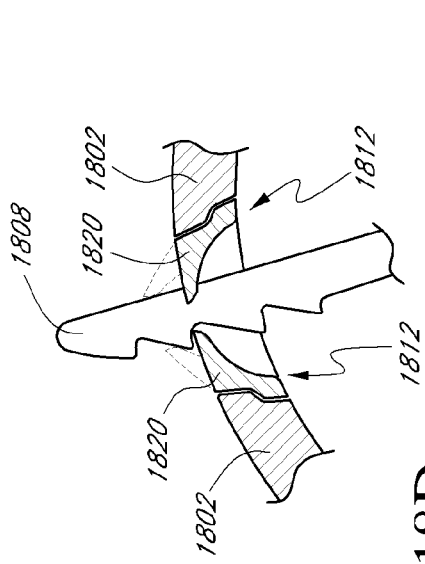

Pulling or pushing the tab 1808 with respect to the base 1802 adjusts the seal geometry around the user's side nose bridge. For example, the inclination angle 1814 between the seal side nose bridge portion 1816 and the seal end plane 1818 increases or decreases depending upon the direction that the tab 1808 is moved. For example, pulling the tab 1808 from a first position (as shown in FIG. 18A) to a second position (as shown in FIG. 18B) adjusts the inclination angle 1814 from about 40° to about 56°. In other embodiments, the inclination angle 1814 is adjustable between about 25° and about 70°, between about 35° and about 60°, or between about 40° and about 50°. As the inclination angle 1814 is increased, the seal side nose bridge portion 1816 applies less pressure against the side of the user's nose. As the inclination angle 1814 in decreased, the seal side nose bridge portion 1816 applies greater pressure against the side of the user's nose. By adjusting the tab 1808, the user controls the amount of compressive force provided by the seal adjustment mechanism 1806 in order to achieve maximum comfort and to eliminate air leakage.

Figure 18C:
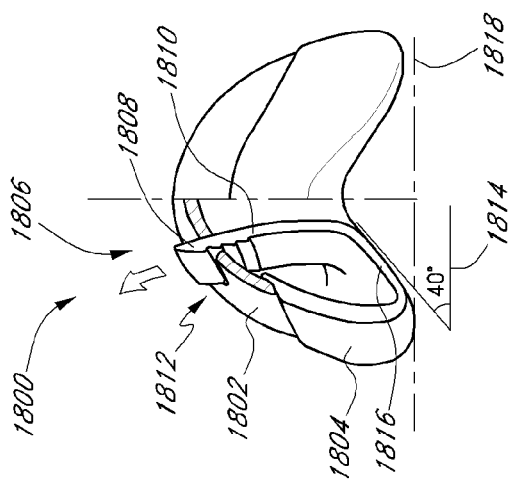
Figure 18D:
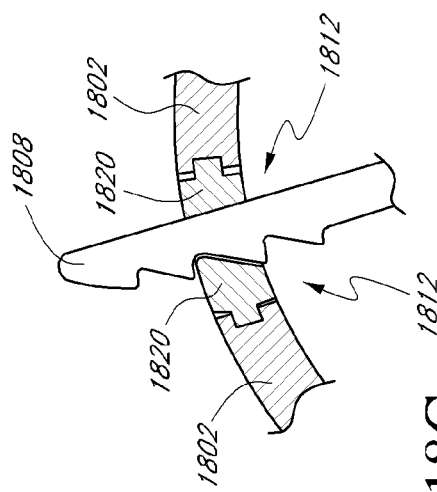

In some embodiments, a gasket 1820 is provided within the mask base opening 1812. The gasket 1820 can provide a seal between the tab 1808 and the mask base 1802. In one embodiment, the gasket 1820 is formed of a flexible silicone material. The gasket 1820 is configured to flex from a first position when the tab 1808 is not pulled (as shown in FIG. 18C) to a second position when the tab 1808 is pulled (as shown in FIG. 18D).

Figure 19A:
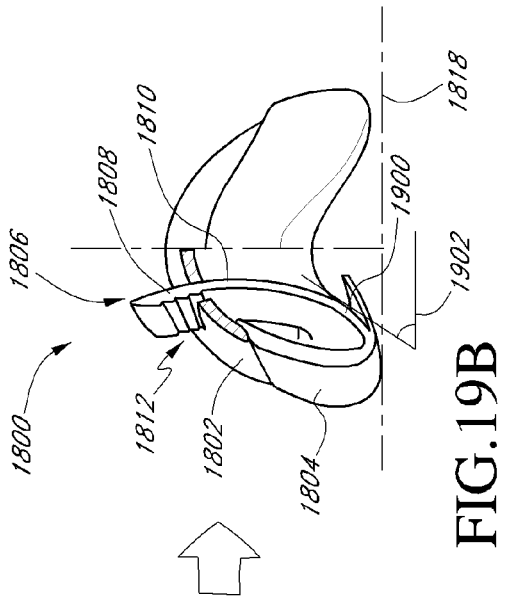
FIGS. 19A-19D are views of another interface comprising a tabbed seal adjustment mechanism.
Figure 19C:
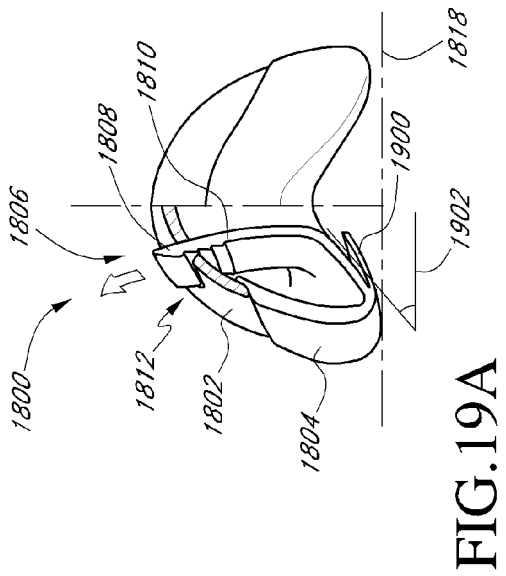
Figure 19B:
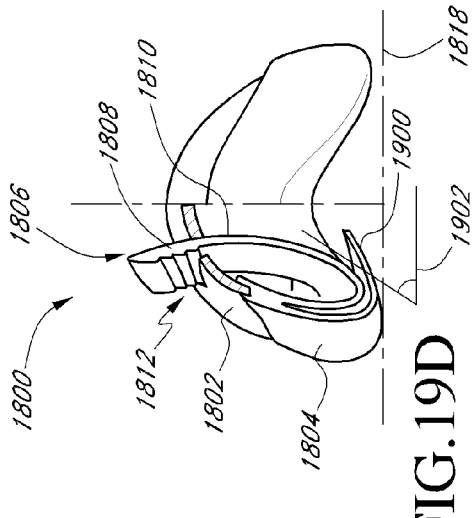
Figure 19D:
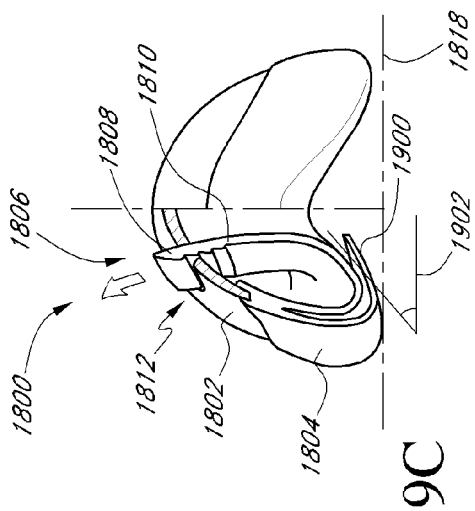

In some embodiments, the mask assembly 1800 comprises a seal 1804 that includes at least one additional seal wall 1900. The additional seal wall 1900 is formed on an inside portion of the seal 1804. In some embodiments, the additional seal wall 1900 extends from the seal 1804 at the location where the tab 1808 is formed. However, the additional seal wall 1900 may be provided with any of the mask seals described herein. In some embodiments, the seal wall 1900 extends from the seal 1804 near or at the points where the seal 1804 intersects the seal end plane 1818, such as shown in FIGS. 19A and 19B. In other embodiments, the seal wall 1900 extends from the seal 1800 near the points where the seal 1804 is coupled to the mask base 1802, as shown in FIGS. 19C and 19D.

Pulling or pushing the tab 1808 with respect to the base 1802 adjusts the seal geometry around the user's side nose bridge. For example, the inclination angle 1902 between the seal wall 1900 and the seal end plane 1818 increases or decreases depending upon the direction that the tab 1808 is moved. For example, pulling the tab 1808 from a first position (as shown in FIGS. 19A and 19C) to a second position (as shown in FIGS. 19B and 19D) adjusts the inclination angle 1902 from about 40° to about 56°. In other embodiments, the inclination angle 1902 is adjustable between about 25° and about 70°, between about 35° and about 60°, or between about 40° and about 50°. As the inclination angle 1902 is increased, the seal wall 1900 applies less pressure against the side of the user's nose. As the inclination angle 1902 in decreased, the seal wall 1900 applies greater pressure against the side of the user's nose. By adjusting the tab 1808, the user controls the amount of compressive force provided by the seal adjustment mechanism 1806 in order to achieve maximum comfort and to eliminate air leakage.

FIGS. 20A and 20B illustrate one embodiment of a mask assembly 2000 configured to provide a lateral compressive force against a user's nose in order to reduce air leakage. The mask assembly 2000 includes a mask base 2002 and a seal 2004. The mask seal 2004 is removably attached to the mask base 2002. The mask assembly 2000 also includes a seal adjustment mechanism 2006. The mask assembly 2000 is compatible with any of the interfaces described herein, and may be provided with a connection port assembly (not shown) and/or a headgear assembly (not shown).

The seal adjustment mechanism 2006 is provided as a thinner section of the seal 2004 wall. In the illustrated embodiment, the thinner wall section is formed between two notches 2008 in the wall of the seal 2004. The apexes of the notches 2008 are aligned with each other on opposite sides of the seal 2004. In some embodiments, the seal adjustment mechanism 2006 includes 1, 3, 5 or less than 10 notches 2008. The notches 2008 may be provided on the outside and/or inside surface of the seal 2004. In some embodiments, the inside and outside notches are aligned with each other (as shown in FIGS. 20A and 20B), and in other embodiments, they are not.

The outside notch 2008 is configured to open from about 45°, as shown in FIG. 20A, to about 90°, as shown in FIG. 20B. The seal 2004 bends at the adjustment mechanism 2006 as the mask assembly 2000 is applied to a user's face. When applied, the user's nose presses against the seal side nose bridge portion 2010, which causes the seal side nose bridge portion 2010 to bend with respect to the seal 2004 at the adjustment mechanism 2006.

As the seal side nose bridge portion 2010 bends, the inclination angle 2012 between the seal side nose bridge portion 2010 and the seal end plane 2014 changes. By adjusting the position of the mask assembly 2000 on the user's face, the user controls the amount of compressive force provided by the seal 2004 in order to achieve maximum comfort and eliminate air leakage.

Figure 21:
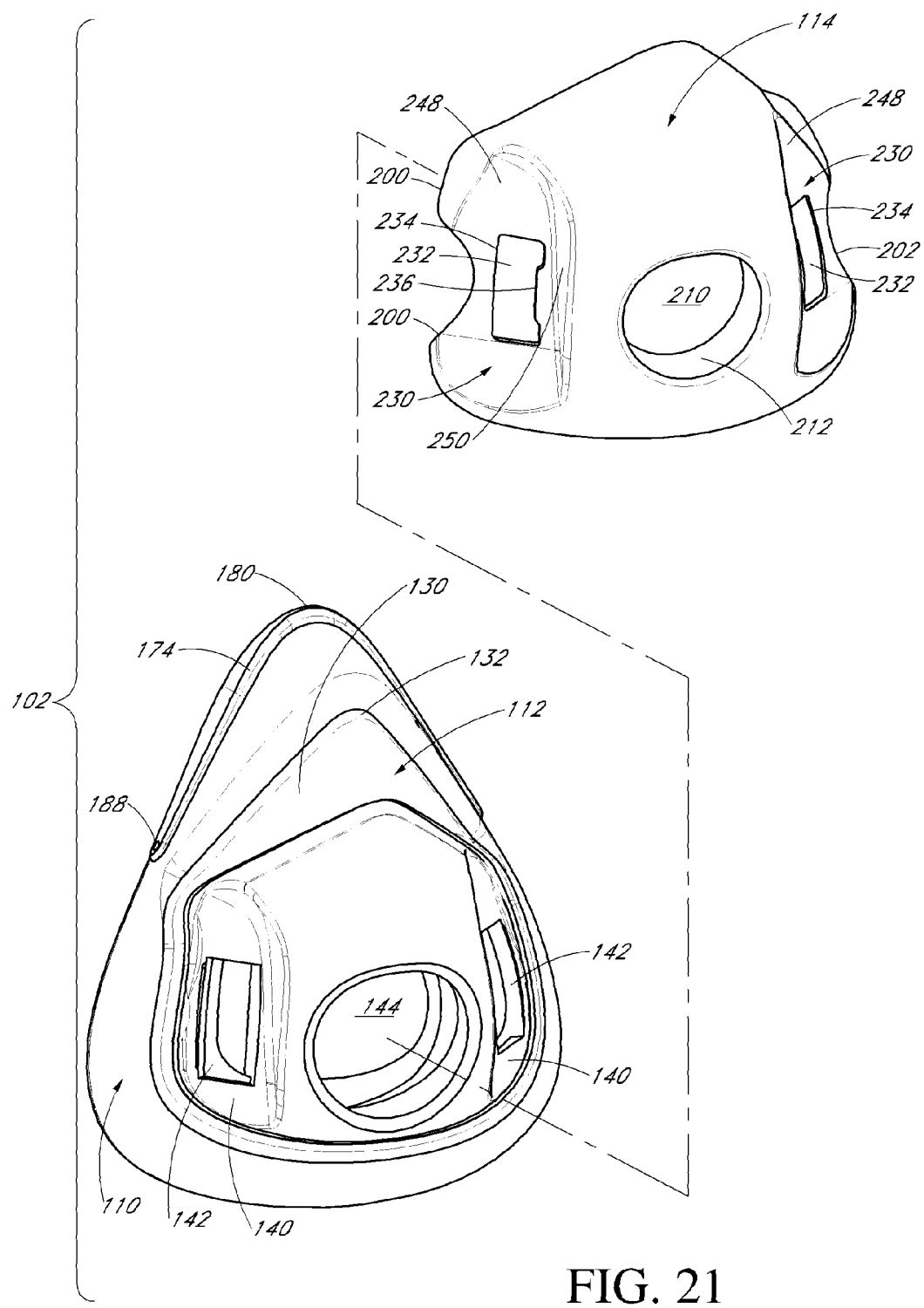
FIG. 21 is a perspective view of a mask seal and mask seal clip compatible with the interface of FIG. 1.

FIG. 21 illustrates one configuration of a mask assembly 102 compatible with any of the interface configurations described herein. The mask assembly 102 generally comprises a mask seal 110, which can include a mask seal clip 112, and a mask base 114. As will be described, the mask seal clip 112 preferably connects the mask seal 110 to the mask base 114. While the illustrated mask seal 110 and mask seal clip 112 are formed separately and secured together, in some configurations, the mask seal 110 and the mask seal clip 112 can be integrated into a single component. In some configurations, the mask seal 110 is overmolded onto the mask seal clip 112. Indeed, in any of the mask assembly configurations described above and below, the mask seal may be removably attached to the mask base, or may be integrally formed with (e.g., co-molded, permanently bonded, etc.) the mask base.

Figure 22:
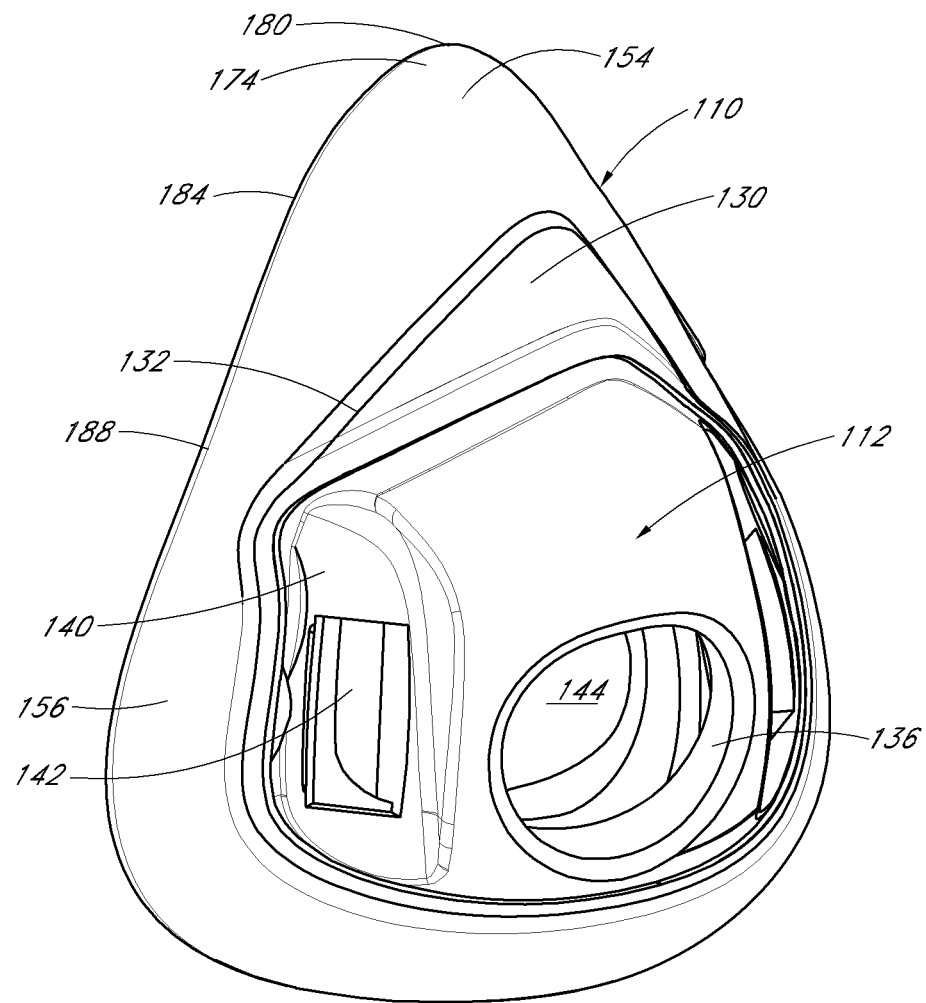
FIG. 22 is a perspective view of a mask seal and mask seal clip of the interface of FIG. 1.

With reference to FIG. 22, the mask seal clip 112 is relatively more rigid, stiffer or more inflexible than the mask seal 110. In some configurations, the mask seal clip 112 is formed of a polycarbonate material. In some configurations, at least a portion of the mask seal clip 112 is formed of a polycarbonate or other rigid or semi-rigid material. In some configurations, the mask seal clip 112 is formed at least partially of silicone or another suitable material. In such configurations, at least the silicone portion of the mask seal clip 112 may be formed to be relatively thicker compared to the more flexible portions of the mask seal 110. The mask seal clip 112 provides structural support to the mask seal 110 in the illustrated configuration.

Figure 23:
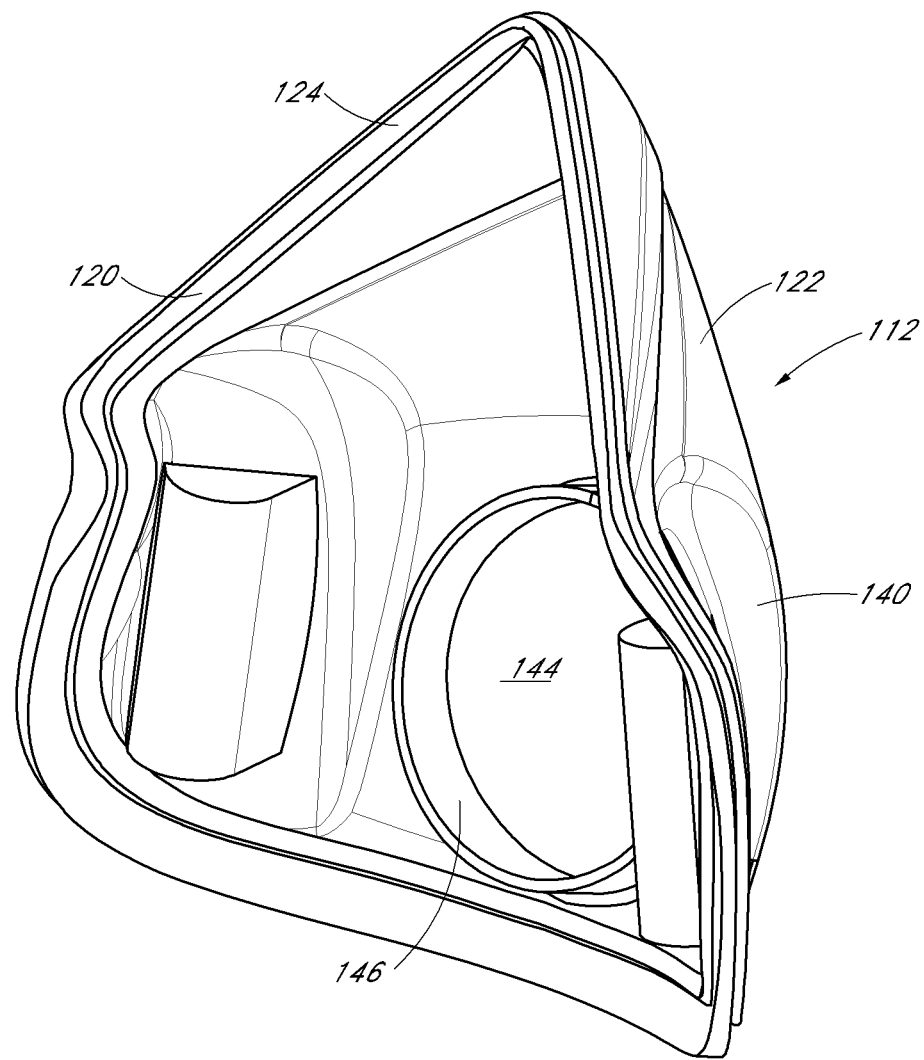
FIG. 23 is a rear perspective view of the mask seal clip of FIG. 22.
Figure 24:
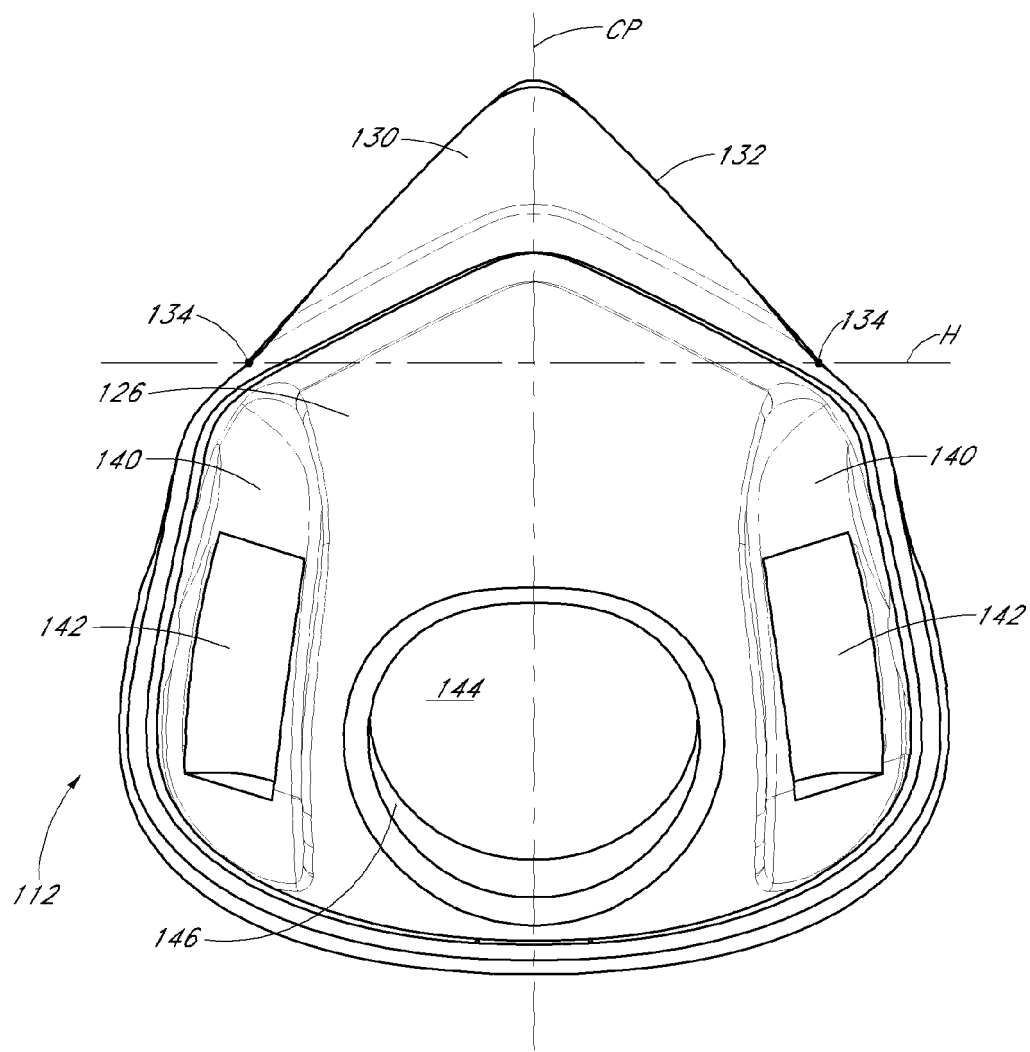
FIG. 24 is a rear elevation view of the mask seal clip of FIG. 22.
Figure 25:
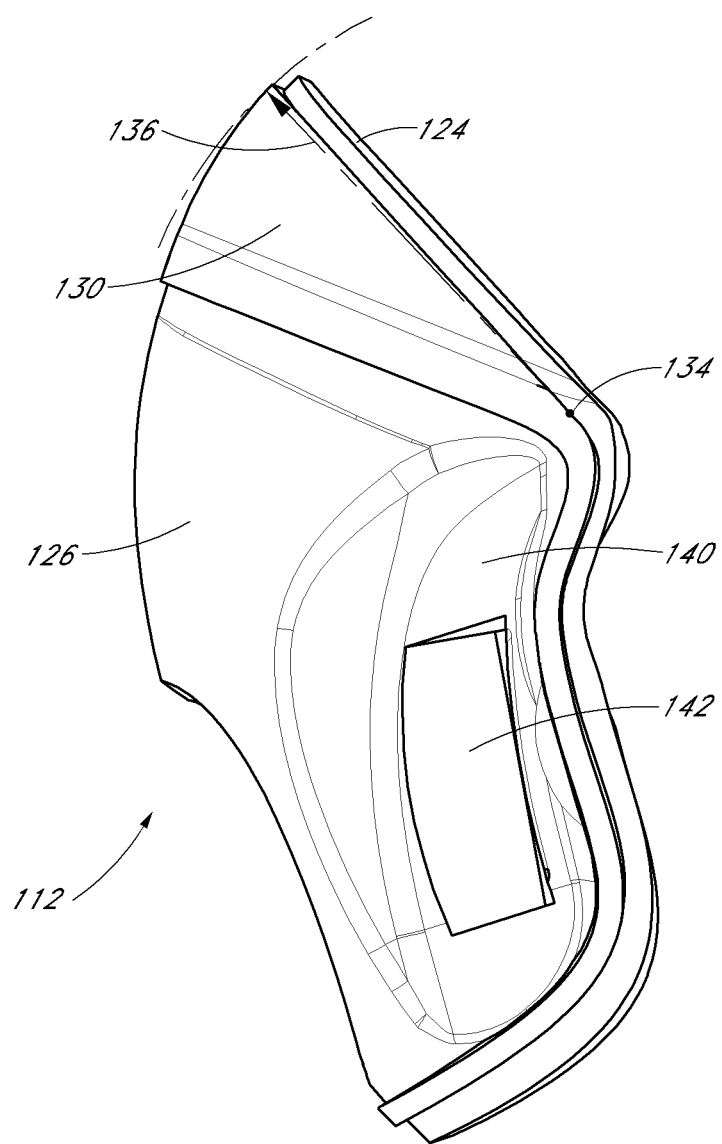
FIG. 25 is a side elevation view of the mask seal clip of FIG. 22.

With reference to FIGS. 23 and 24, the illustrated mask seal clip 112 comprises a substantially cup-shaped configuration. A proximal end 120 defines an open end of the illustrated mask seal clip 112 while a distal end 122 defines a generally closed end of the illustrated mask seal clip 112. In the illustrated configuration, the proximal end 120 is generally circumscribed by a lip 124. The lip 124 is generally pentagonal when viewed from the back. As shown in FIG. 25, a wall 126 generally sweeps forward in an arcuate manner. The arcuate shape to the wall 126 provides a three dimensional configuration to the illustrated mask seal clip 112.

With continued reference to FIG. 25, an upper portion 130 of the illustrated mask seal clip 112 is generally arcuate in configuration. In addition, the generally arcuate configuration of the illustrated mask seal clip 112 is configured to accommodate larger noses while not extending upward over the nose to as great an extent as the mask seal 110, as shown in FIGS. 1 and 2.

Referring again to FIG. 22, the upper portion 130 of the illustrated mask seal clip 112 preferably comprises two arcuate dimensions. First, an arc length 132 can be defined along an upper extremity of the upper portion 130 of the illustrated mask seal clip 112. The arc length 132 can be defined between inflection points 134 found along a perimeter of the illustrated mask seal clip 112.

As shown in FIG. 25, the upper portion 130 of the illustrated mask seal clip 112 also comprises a side profile radius 136. As shown, the upper portion 130 can have a slightly increasing side profile radius 136 such that the radius increases slightly as a distance from the upper end increases. In some configurations, the upper portion 130 can comprise a substantially constant side profile radius 136 or a decreasing side profile radius. Advantageously, the slightly increasing side profile radius 136 provides an increased volume in the mask 100 proximate the user's nose.

With reference to FIG. 22 and FIG. 24, the mask seal clip 112 preferably comprises at least two recesses 140. In the illustrated configuration, the mask seal clip 112 comprises two recesses 140 that are disposed on two lateral sides of a generally vertical center plane CP (see FIG. 24). The generally vertical center plane CP preferably corresponds to a mid-sagittal plane of the user and splits the illustrated mask seal clip 112 into substantially mirror image halves. The two recesses 140 define two generally enclosed pockets in the illustrated mask seal clip 112. The illustrated recesses 140 comprise further recesses 142 that are used to provide adequate clearance for reasons that will be discussed below while limiting an amount of encroachment into a nasal region of a chamber defined by the mask assembly 102.

The illustrated mask seal also comprises a generally central passage 144 that is defined by a wall 146. In the illustrated configuration, the wall 146 generally encloses the passage 144. Preferably, the wall 146 is generally cylindrical in configuration and extends through the wall 126. Other configurations are possible.

With reference now to FIGS. 1 and 2, the mask assembly 102 includes the mask base 114, which is more rigid than the mask seal 110. The mask base 114 can be formed of any suitable material. In some configurations, the mask base 114 is formed of a polycarbonate material such that it is capable of flexing for connection with the mask seal 110 and/or the mask seal clip 112.

With reference now to FIG. 21, the mask assembly 102 is shown with the mask base 114 secured to the mask seal 110. More particularly, in the illustrated configuration, the mask base 114 is secured to the mask seal clip 112 that is attached to the mask seal 110 in any suitable manner. In some configurations, the mask base 114 and the mask seal 110 or mask seal clip 112 are removably connected. In some configurations, the mask base 114 snaps together with one or both of the mask seal 110 and the mask seal clip 112. Preferably, the mask seal 110 and the mask seal clip 112 can be removed from the mask base 114 and a snap connection secures the mask seal clip 112 to the mask base 114.

The illustrated mask base 114 overlies at least a portion of the mask seal clip 112. In some configurations, the mask base 114 almost entirely covers the mask seal clip 112. In some configurations, the mask base 114 extends over more than half of the mask seal clip 112. When the mask base 114 overlies a substantial portion of the mask seal clip 112 or the mask seal 110, a double layer effect is created (e.g., the mask seal clip 112 and the mask base 114). The double layer effect provides increased insulation when a significant portion of the mask base 114 overlaps a significant portion of the mask seal clip 112 or the mask seal 110. The increased insulation provides a warmer inner portion (e.g., mask seal 110 and/or mask seal clip 112), which results in less rain out of humidity during use. Preferably, at least a portion of the mask seal clip 112 is exposed from under the mask base 114 such that the mask base 114 can be more easily separated from the mask seal clip 112. To aid in the separation of the mask base 114 from the underlying mask seal 110 and/or mask seal clip 112, the illustrated mask base 114 comprises a peripheral surface 200 on the proximal end. The mask base 114 is concave on the inside to accommodate the underlying components. In other words, the mask base 114 is bowl shaped in a distal direction relative to the proximal peripheral surface 200.

The peripheral surface 200 comprises one or more recessed portions 202. Preferably, the recessed portions 202 comprise at least two recessed portions 202 that are positioned on opposite sides of the mask base 114 from each other. The recessed portions 202 are configured to receive a thumb and a finger such that the mask base 114 can be more easily removed from the front of the underlying mask seal clip 112. While the recessed portions 202 can define means for grasping the assembly underlying the mask base 114 for removal of the mask base, other configurations can be used, such as outwardly extending tabs, protruding portions and the like, for example but without limitation. In addition, while the illustrated recessed portions 202 are disposed on opposing lateral sides of the mask base 114, the recessed portions 202 can be positioned on the top and bottom or on other regions as desired.

As shown in FIG. 21, the mask base 114 preferably comprises an opening 210 that is defined by a wall 212. The wall 212 that defines the opening 210 through the mask base 114 preferably fits within the wall 146 that defines the passage 144 through the mask seal clip 112. The wall 212 can be axially coextensive with the wall 146. In addition, the dimensions and shapes of the walls 146, 212 can be such that the walls interact with each other to reduce relative slippage between the walls 146, 212 and to reduce the likelihood of the mask seal base 114 inadvertently separating from the mask seal clip 112. In some configurations, the walls 146, 212 fit together and reduce the likelihood of leakage through the interface between the walls. Preferably, a taper lock secures the walls 146, 212 together.

The wall 212 comprises a contoured inner surface 214. The contoured surface 214 can be radiused to receive a ball end 220 of a swiveling elbow 222, such as that shown in FIG. 26. As better shown in FIG. 27, the ball end 220 has a contoured surface 224 that can be snap fit into the contoured surface 214 formed in the mask base 114. The connection between the two contoured surfaces 214, 224 allows the surfaces to slide relatively freely with each other such that the position of the swiveling elbow 222 can be easily changed. In some configurations, the elbow 222 could be configured for rotation or swiveling without having a ball-joint configuration.

With reference again to FIG. 21, the mask base 114 also comprises at least two pockets 230. The illustrated mask base 114 comprises two pockets 230. The pockets 230 recede into the mask base 114 and protrude rearward from the mask base 114. The pockets 230 are received within the recesses 140 of the mask seal clip 112. Overlying the further recesses 142 formed in the mask seal clip 112 are openings 232 that are defined by a surrounding wall 234.

The illustrated pockets 230 are formed such that one pocket 230 is formed on each lateral side of the mask base 114. The pockets 230 can be positioned to be symmetrical relative to the central plane CP, which plane substantially bisects the mask base 114. In some configurations, the pockets 230 have an enlarged vertical dimension 240 relative to a transverse dimension 242. Similarly, the openings 232 have an enlarged vertical dimension 244 relative to a transverse dimension 246.

In the illustrated mask base 114, the laterally inward portion of each pocket 230 comprises a support wall 250. The support wall 250 is positioned toward the center plane CP relative to normal a base surface 248 of the pocket 230. Each of the pockets 230 is configured to receive a clip 252 (see FIG. 28). Once the clip 252 is installed within the pocket 230, the support wall 250 helps to limit rotation of the clip 252 relative to the pocket 230. Moreover, the large vertical dimension helps users to locate the pocket 230 with the clip 252 during installation.

Figure 28:
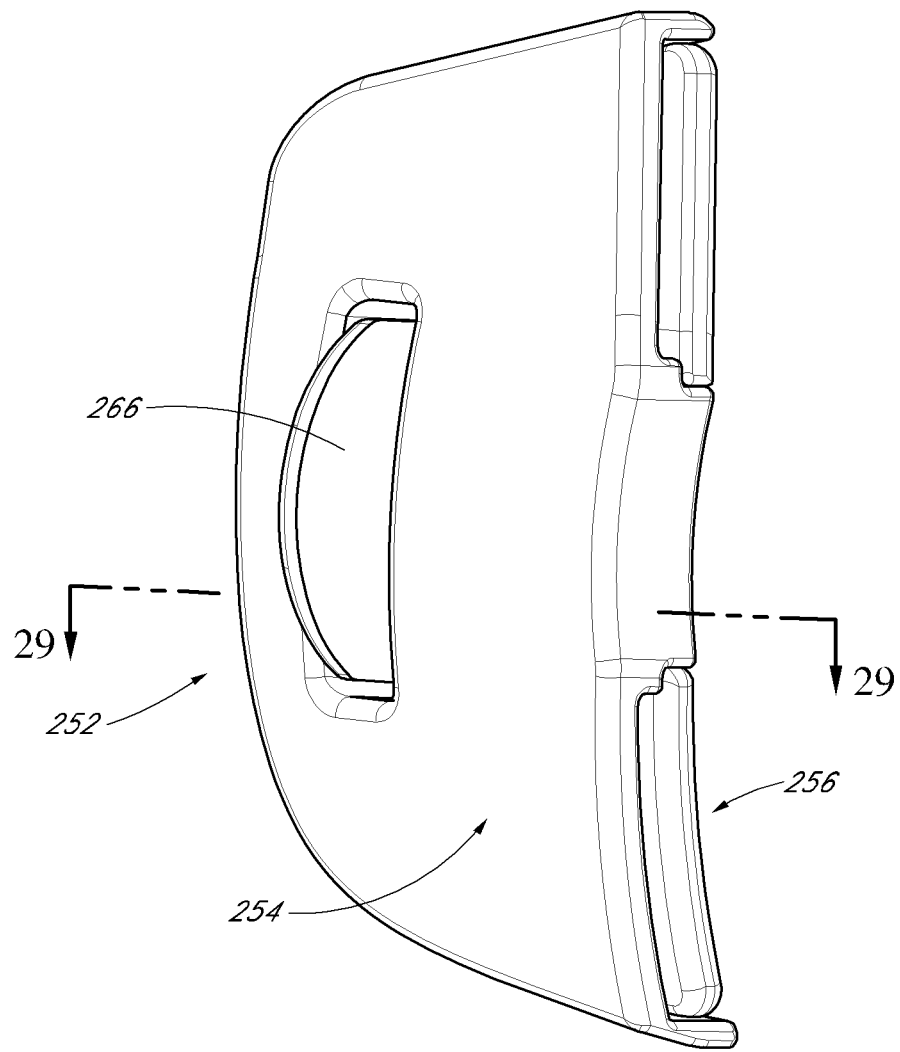
FIG. 28 is a perspective view of the clip assembly of FIG. 1.

With reference to FIG. 28, the clip 252 can have a two part construction: an outer cover 254 and an inner catch 256. Straps 260 can be secured to each clip 252 in any suitable manner. One suitable configuration is illustrated in FIG. 2. In some configurations, the straps 260 can be sandwiched between the outer cover 254 and the inner catch 256. In some configurations, loops or openings or holes could be provided on the clips 252 through which the straps 260 are threaded. Preferably, one clip 252 can be connected to both an upper strap and a lower strap of the headgear assembly 106. Such a configuration facilitates easy connection of the headgear assembly 106 to the full face mask assembly 102 and easy disconnection of the headgear assembly 106 from the full face mask assembly 102.

Figure 29:
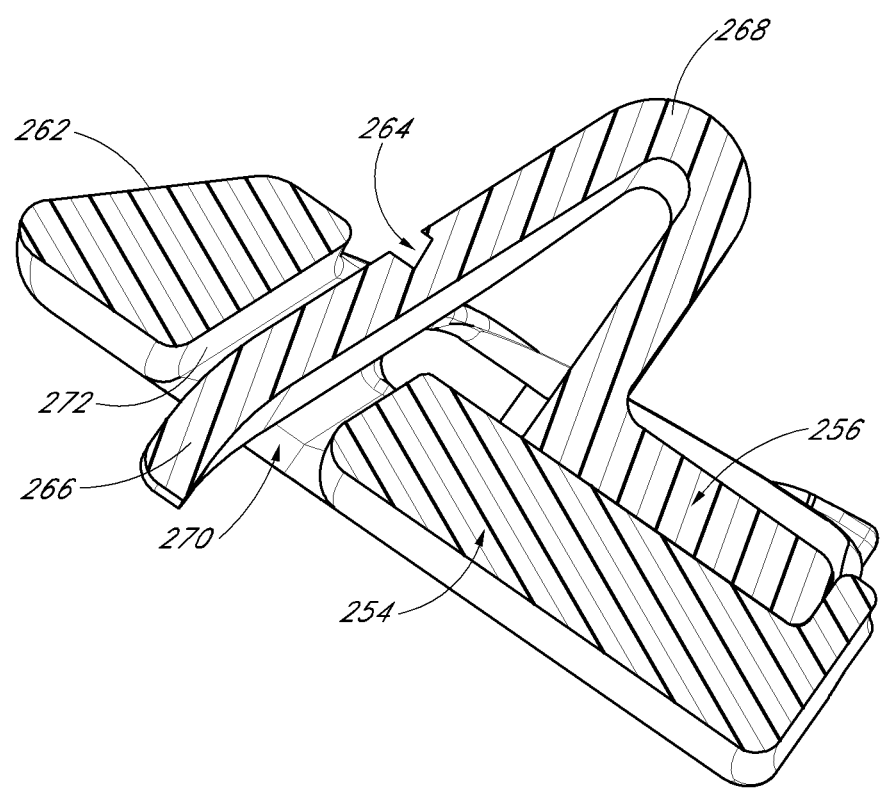
FIG. 29 is a cross sectional view of the clip assembly of FIG. 28 taken along line 29-29.

As shown in FIG. 29, the clip 252 comprises a sloping surface 262. The sloping surface 262 can be positioned on the outer cover 254. The sloping surface 262 cooperates with the support wall 250 to help orient the clip 252 relative to the pocket 203 of the mask base 114.

The clip 252 includes an interlock feature 264. The interlock feature 264 is configured for insertion into the opening 232 defined in the pocket 230 of the mask base 114. The interlock feature 264 can engage in a snap-fit manner with a tab 236 defined along the wall 234 that defines the opening 232 in the mask base 114, as shown in FIG. 21. Other manners of interlocking the clip 252 with the pocket 230 also can be used.

Referring to FIG. 29, the interlock feature 264 of the illustrated clip 252 comprises a U-shaped component 268 that terminates in a release lever 266. The U-shaped end 268 protrudes a sufficient distance to allow the connection with the tab 236 but does not protrude so far as to allow the bottom of the further recess 142 in the mask seal clip 112 to stop proper insertion of the interlock feature 264 into the opening 232. The U-shaped end 268 initially makes contact with a wall of the opening 232 during connection of the clip 252 to the mask base 114. In the illustrated configuration, the U-shaped end 268 contacts the wall 234 of the opening 232 during insertion and the wall 234 guides the clip 252 into position within the pocket 230. The opening 232, or one or more surfaces that define the opening 232, generally align the clip 252 relative to the mask base 114 during connection of the clip 252 to the mask base 114.

The end of the release lever 266 protrudes through an opening 270 defined by a wall 272. Preferably, the end of the release lever 266 protrudes through the opening 270 a sufficient distance to allow easy manipulation of the release lever 266. Moving the release lever 266 in manner that closes the U-shape of the interlock feature 264 allows the interlock feature 264 to be removed from engagement with the tab 236 in the wall 234 that defines the opening 232 in the mask base 112.

FIGS. 30-37 illustrate additional configurations of clip assemblies 252 that are configured to secure a mask assembly 102 to a user's head. The clip 252 of FIGS. 30 and 31, for example has a raised edge 400 (sometimes referred to as a finger tab 400) that enables the user to easily detach the headgear 106 from the mask assembly 102. The raised edges 400 are oriented such that the user may merely pull them rearwardly to pop the clips 252 off of the mask base 114. Removing one or more clips 252 from the mask base 114 allows the mask assembly 102 to be easily removed from the user's head. The raised edge 400 provides a grasping point during attachment and removal of the headgear 106 with respect to the mask assembly 102. For example, the user's thumb and index finger may be placed on opposite sides of the raised edge 400 during removal of the clip 252 from the mask assembly 102. In addition, the user may grip the clip 252 and maintain the grip throughout the mask fitting process. This eliminates the need to grasp blindly for straps 260 during assembly. It also allows the user to attach the clip 252, remove it, and re-attach it while maintaining a grip on the raised edge 400.

Figure 30:
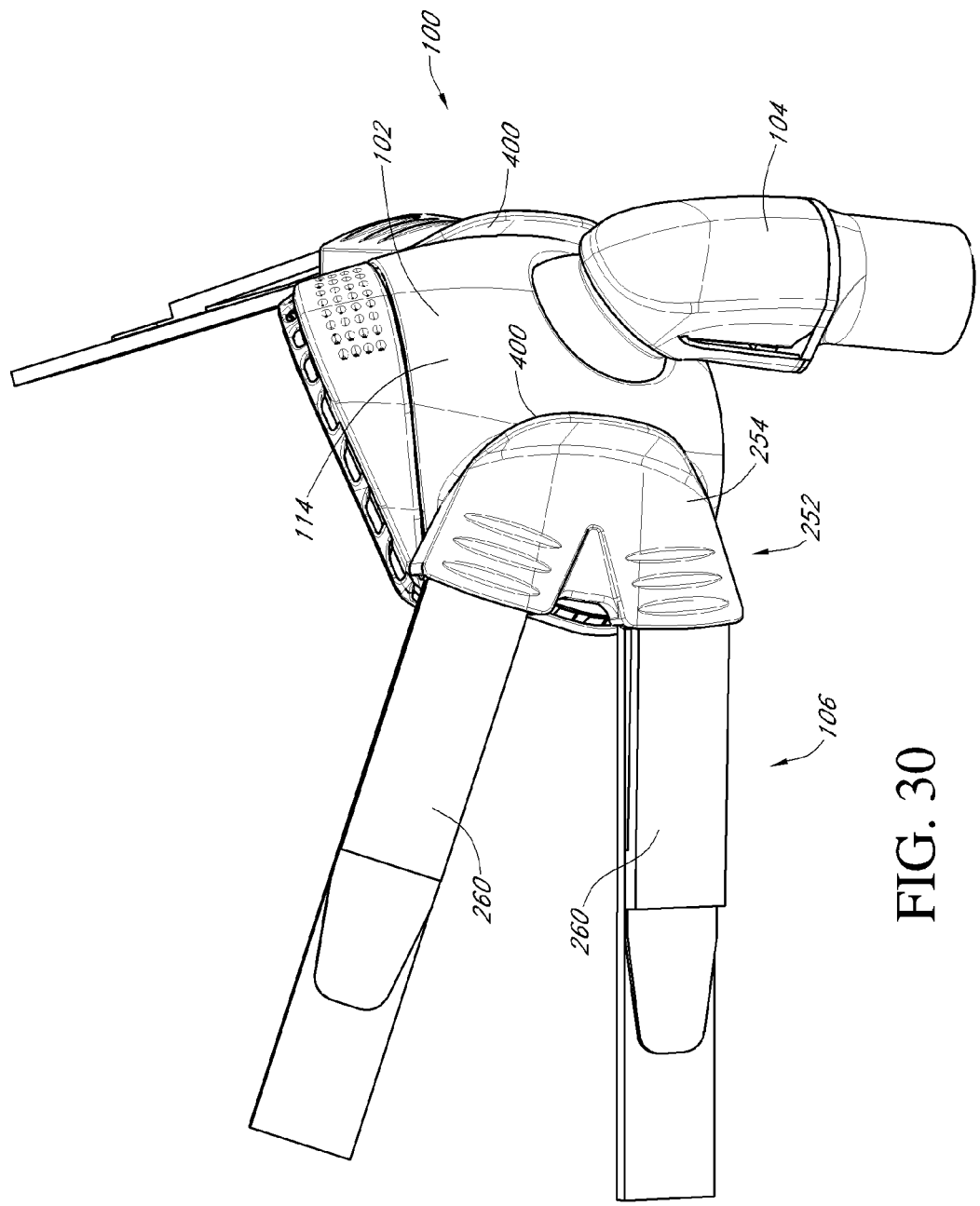
FIG. 30 is a perspective view of a mask assembly comprising a mask, clips, and straps.
Figure 31:
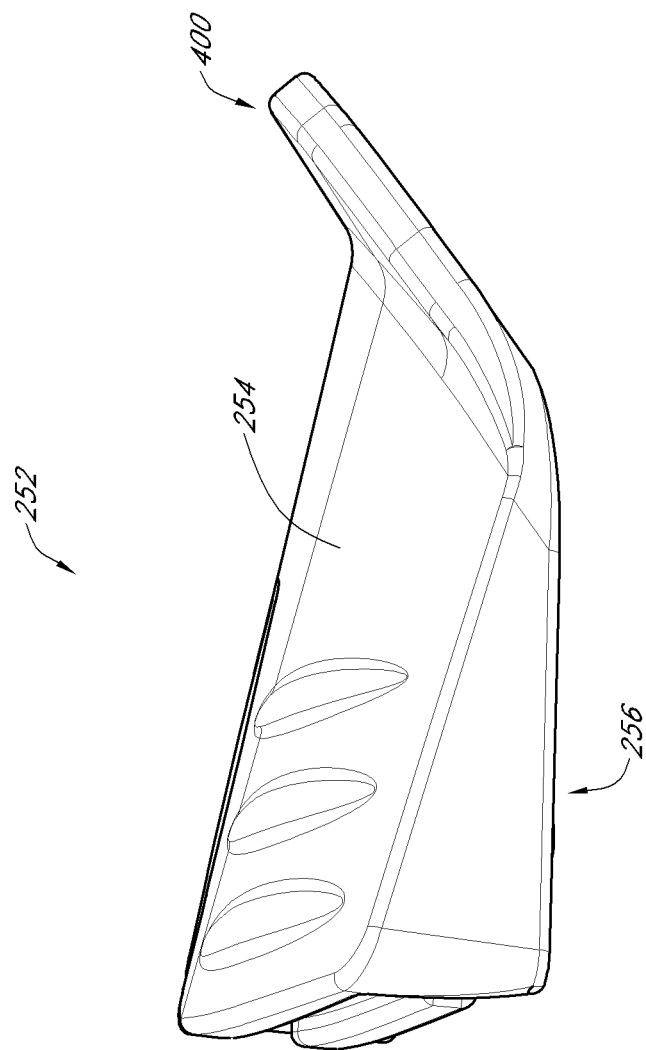
FIG. 31 is a side view of one of the two clips of FIG. 30.
Figure 33:
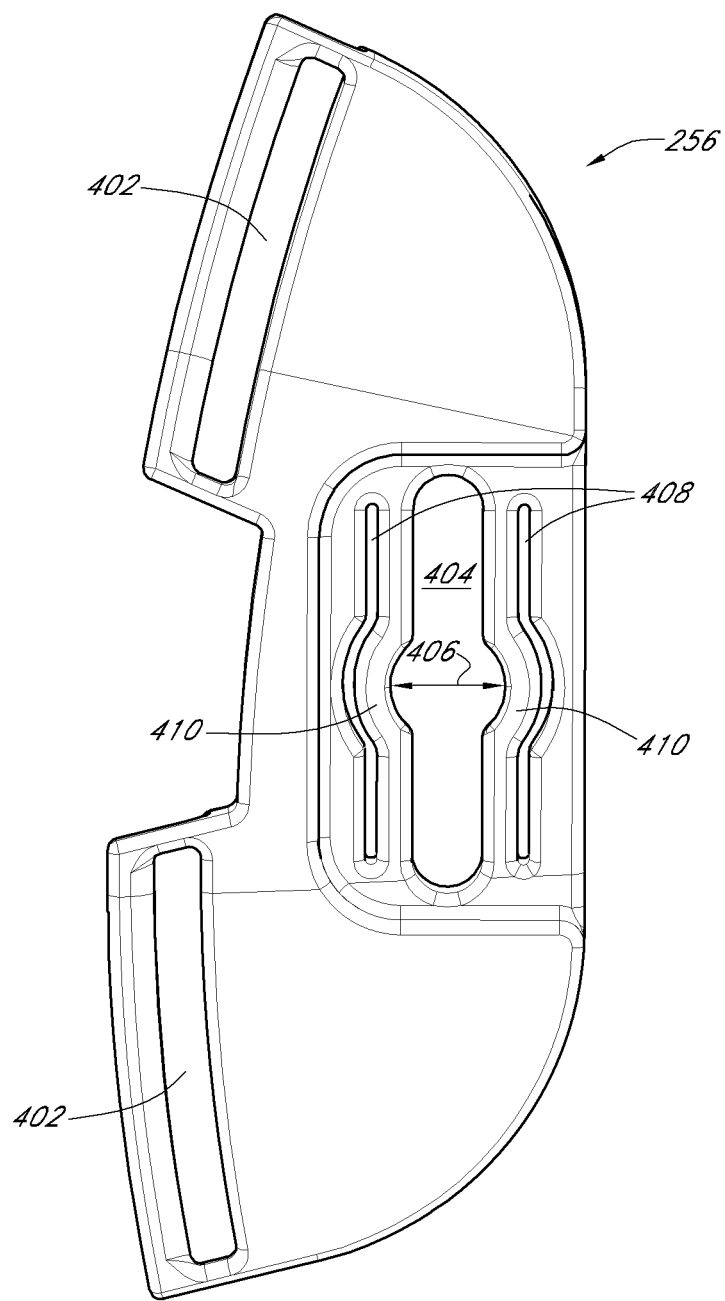
FIG. 33 is a top view of the inner catch of the clip of FIG. 31.

FIG. 32 shows an exploded view of the clip 252 of FIGS. 30 and 31. The clip 252 includes an outer cover 254 and an inner catch 256. The inner catch 256 includes one or more slots 402 to receive the distal end of the headgear straps 260. The inner catch 256 can also include several pressure bumps, such as those shown in connection with the configuration of FIGS. 36 and 37. The pressure bumps provide additional pressure against the outer cover 254 and inner catch 256, so that they are secured to one another. In one configuration, the headgear straps 260 are removable from the assembled clip 252.

Figure 36:
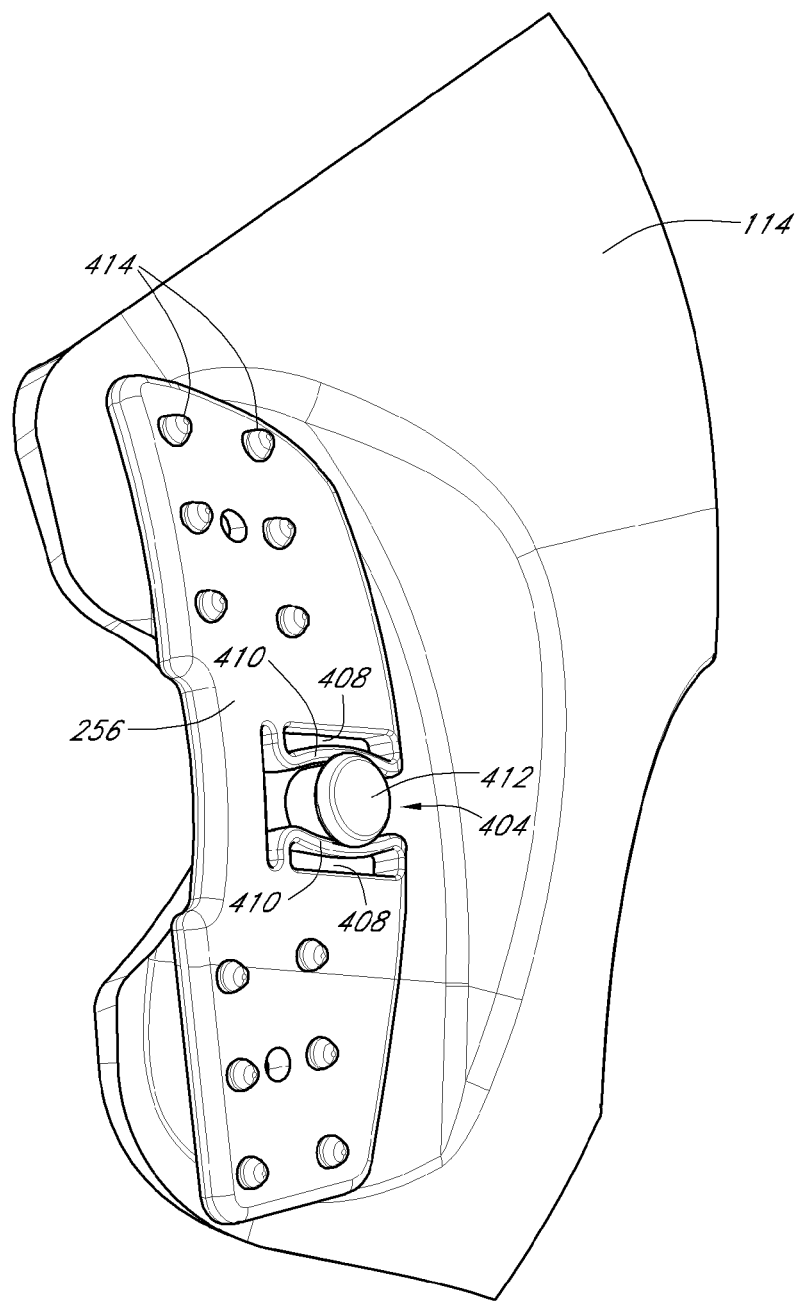
FIGS. 36-45 are additional configurations of clips and associated masks and mounting posts.

The inner catch 256 includes an elongated slot 404, as shown in FIG. 36. The slot 404 includes a circular opening 406 having a diameter larger than the width of the slot 404. The slot 404 and circular opening 406 can include chamfered recesses to help align the clip 252 to the mask assembly 102. The circular opening 406 facilitates attachment and removal of the clip 252 to the mask assembly 102, as will be discussed in greater detail below. Two channels 408 extend parallel to the sides of the slot 404, thereby defining slot walls 410 (sometimes referred to as clip levers) on either side of the slot 404. The channels 408 are sized to permit adequate flexing of the slot walls 410 during attachment and removal of the clip 252 from the mask assembly 102. In addition, the slot walls 410 extend along the longest dimension of the inner catch 256, towards top and bottom, which allows longer slot walls 410 to be employed. Longer slot walls 410 reduces the level of stress on the slot walls when fitting the clip over the mounting post.

Figure 34:
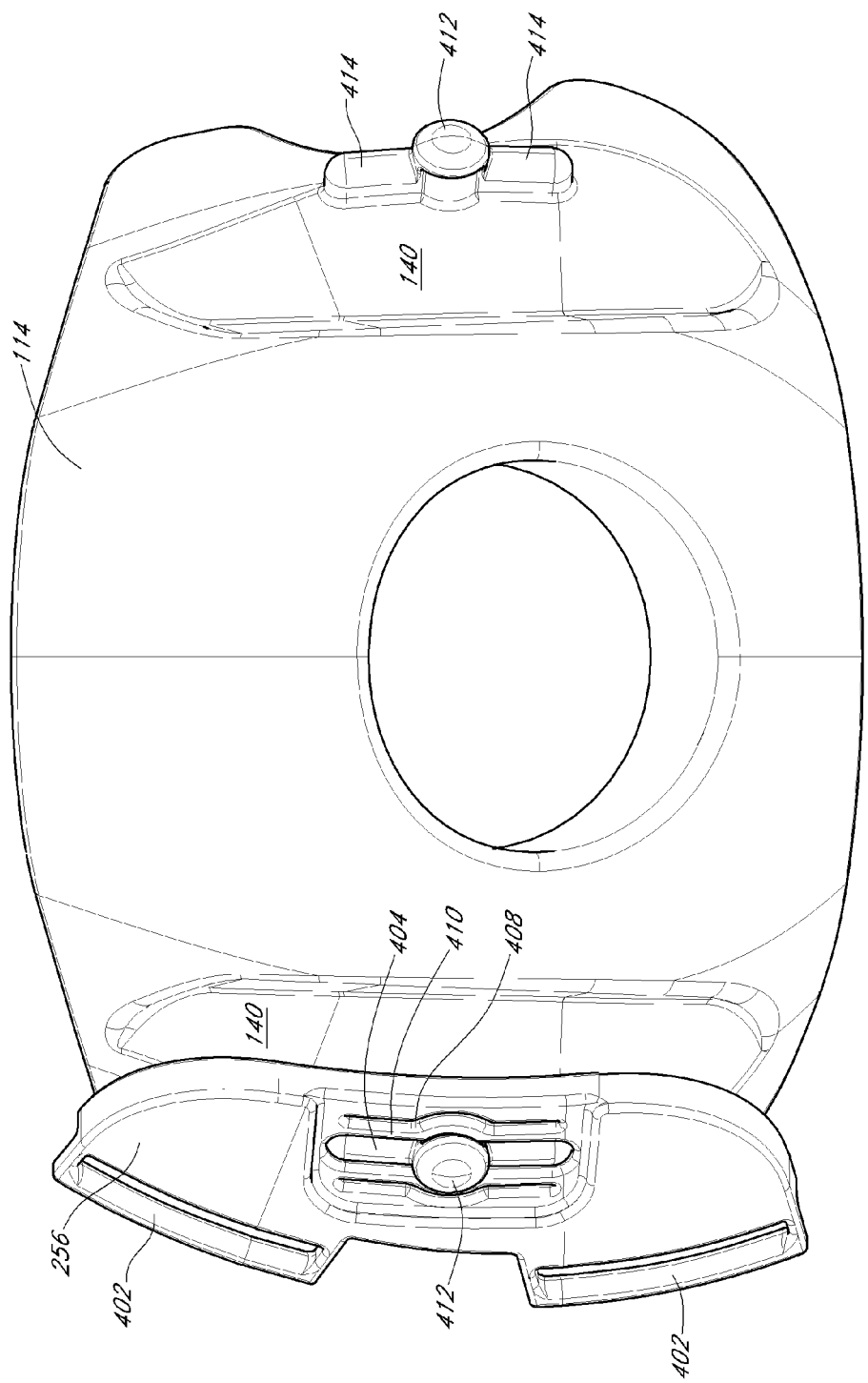
FIG. 34 is a front view of a mask base having two mounting posts, and one inner catch of a clip mounted to the left mounting post.
Figure 35:
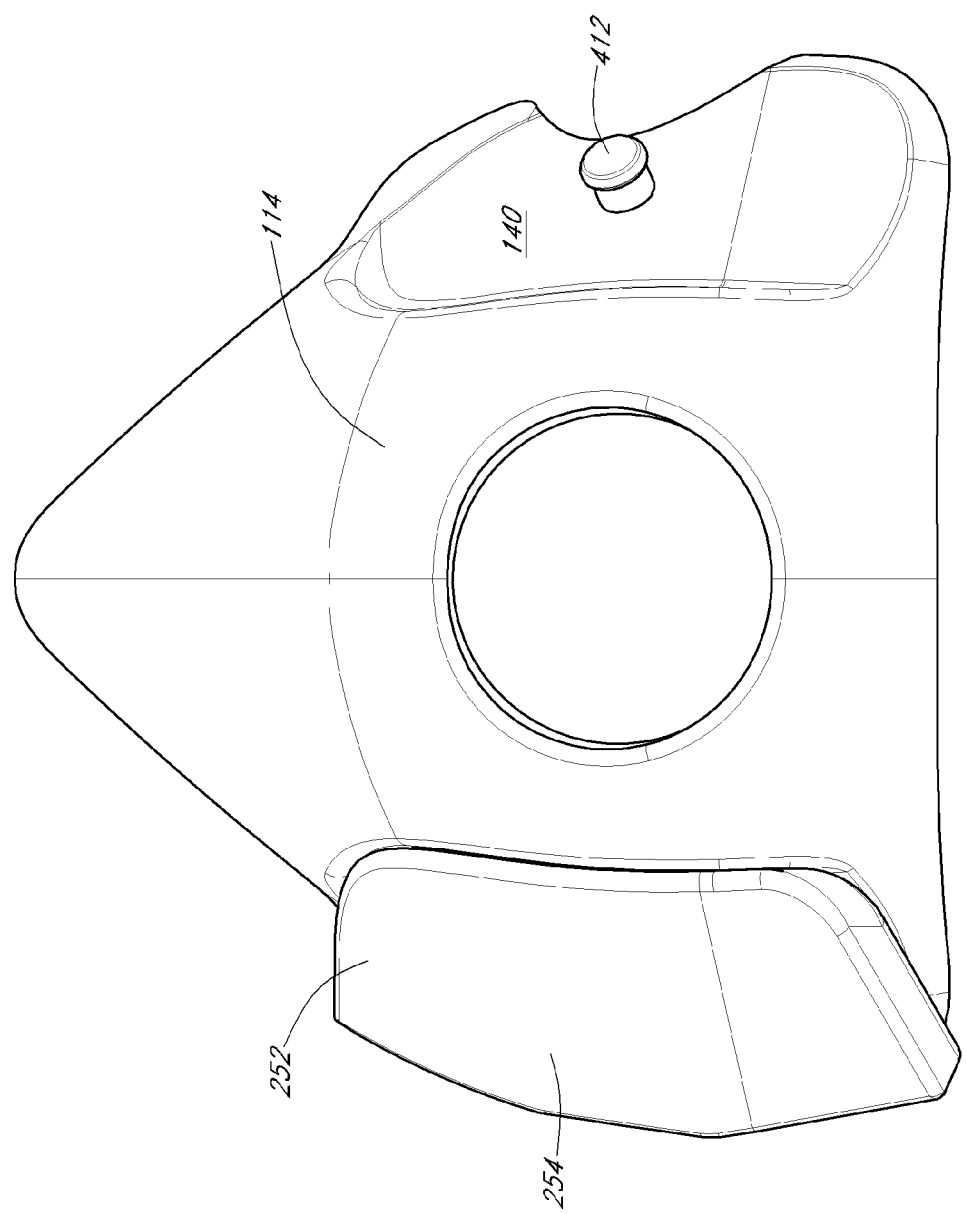
FIG. 35 is a front view of another configuration of a mask base having two mounting posts, and another configuration of a clip mounted to the mask base's left mounting post.

One configuration of a mask base 114 suitable for use with the clip 252 of FIGS. 30-33 is illustrated in FIG. 34. The mask base 114 includes two recesses 140 symmetrically positioned on opposite sides of the mask base 114. A mounting post 412 extends from the body of the mask base 114 within each recess 140. The mounting post 412 may be integrally formed with the mask base 114, or separately formed and secured to the mask base 114. The mounting post 412 can have a mushroom-shaped configuration to secure the clip 256 to the mask base 114 once the user snaps the clip 256 in place. The rounded top of the bulbous mushrooms-shaped post 412 helps locate and orient the central hole 406. As the clip 252 is pressed onto the post 412, the slot walls 410 deflect outwardly, away from the post 412. Once the head of the post 412 clears the edge of the slot wall 410, the slot walls 410 snap back to their original position, thereby providing tactile, and sometimes audible feedback, that the clip 252 is properly attached to the mask assembly 102.

The mounting post 412 can also comprise an elongated, elliptical, elevated portion 414 (sometimes referred to as a lug or wing) that is sized to mate with the elongated slot 404 of the inner catch 256. The elongated, elevated portion 414 comprises a chamfered edge to help properly align the head gear 106 with respect to the mask assembly 102. The portion 414 also prevents the clip 252 from rotating with respect to the mask assembly 102. This helps assure constant tension on the headgear straps 260 while the user sleeps.

Figure 37:
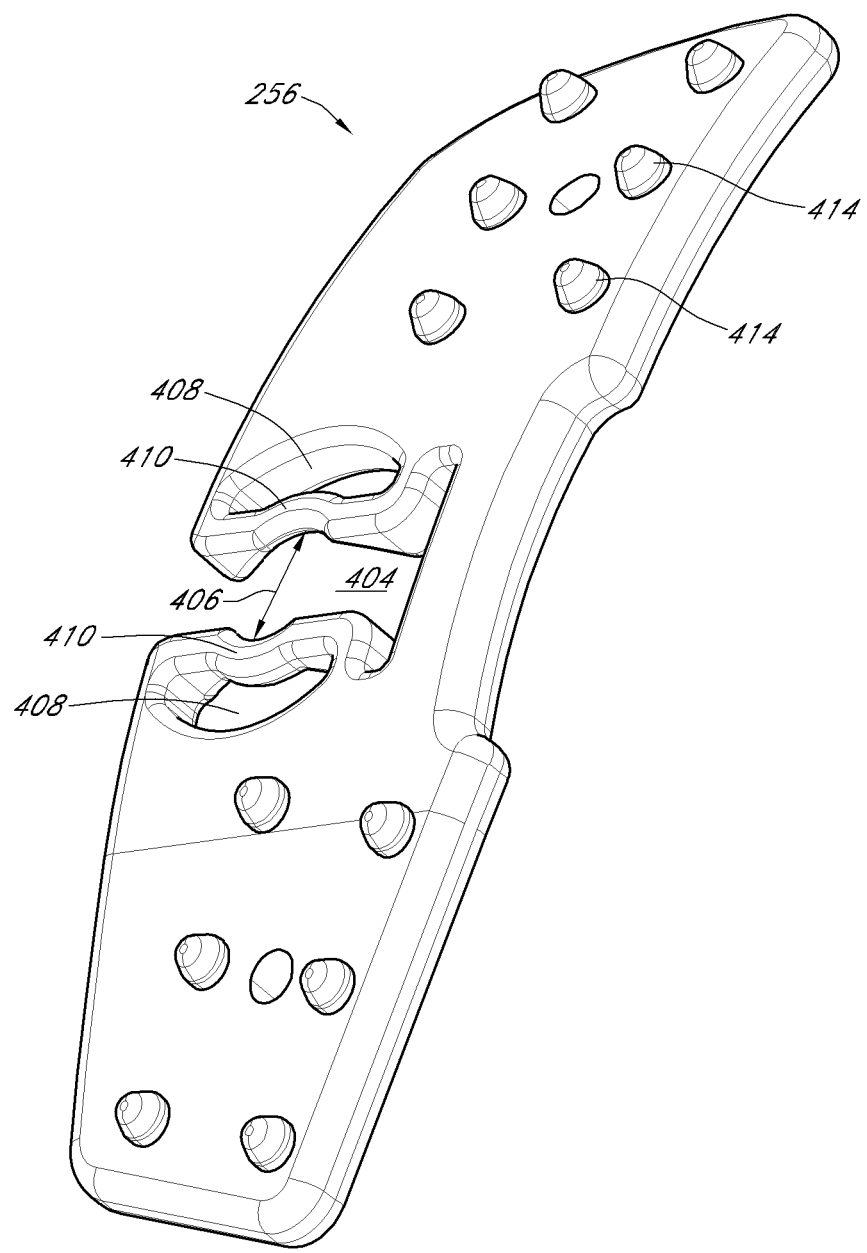
Figure 38:
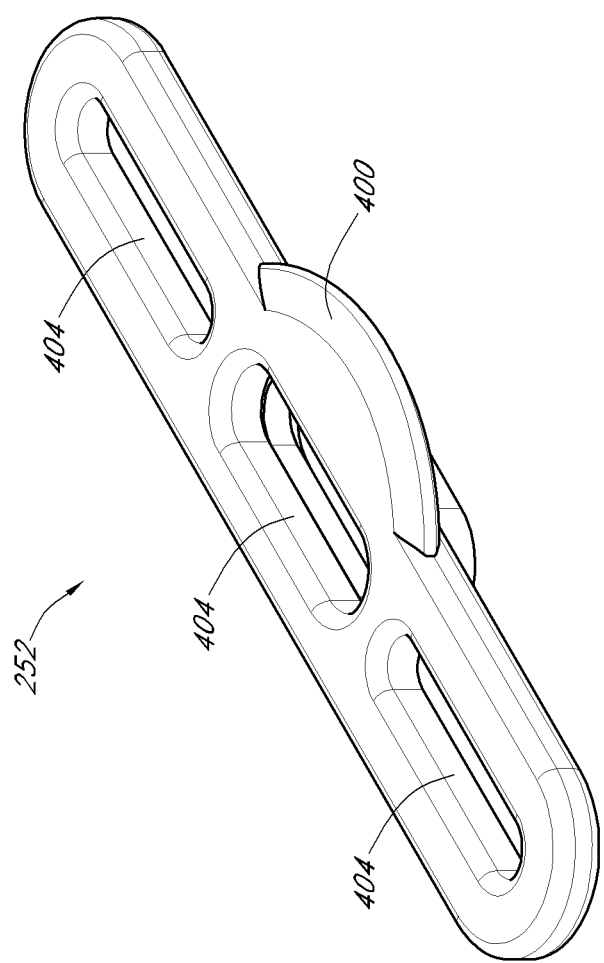
Figure 39:
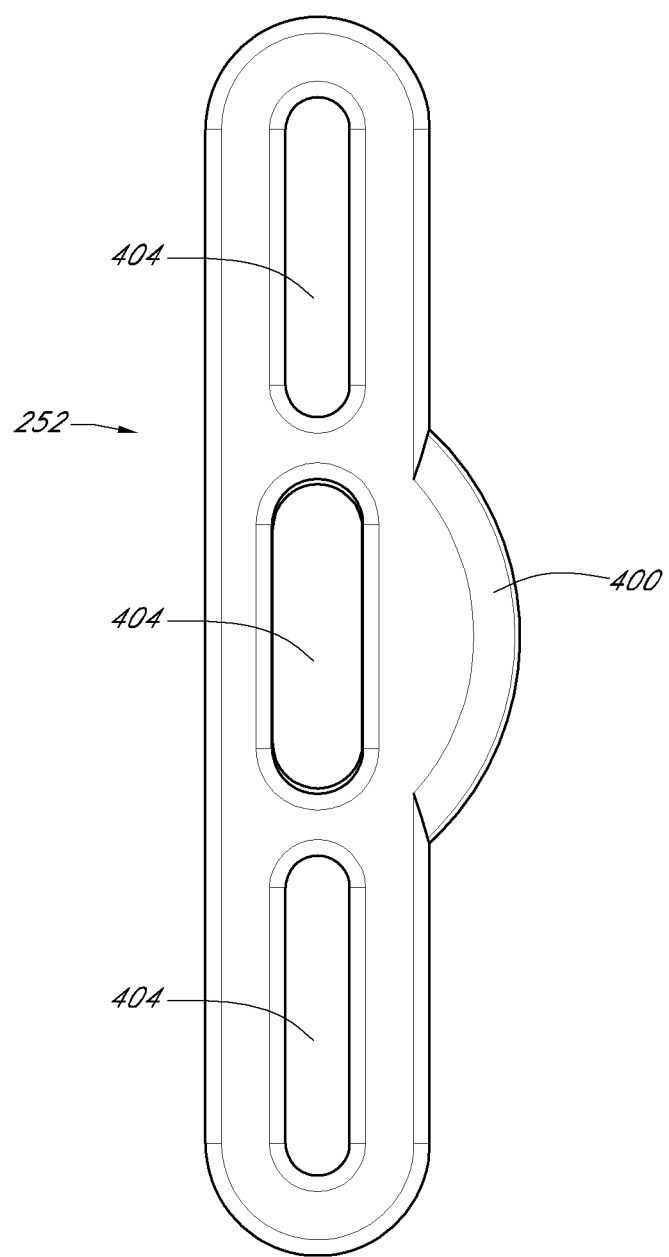
Figure 40:
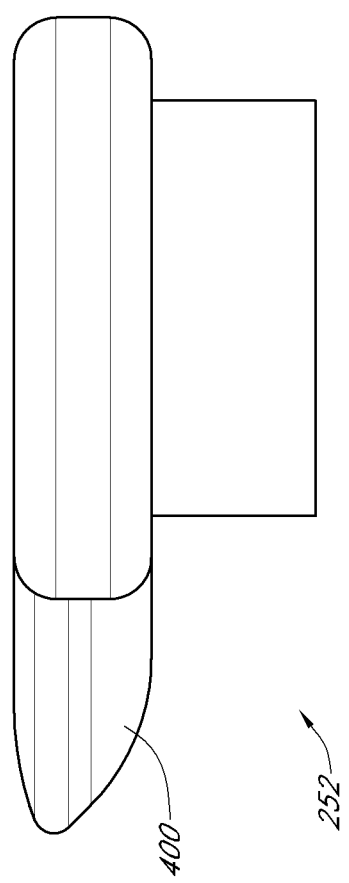
Figure 42:
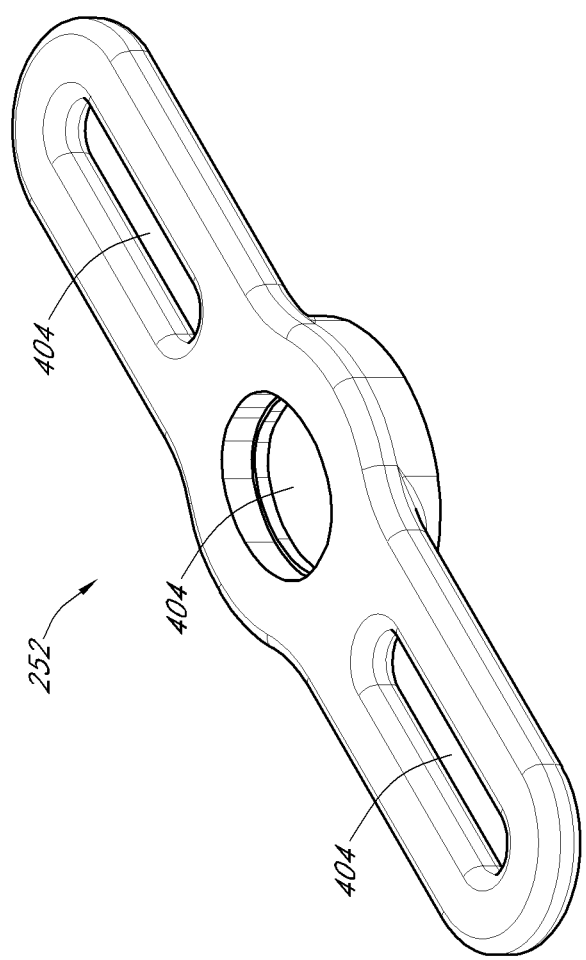
Figure 43:
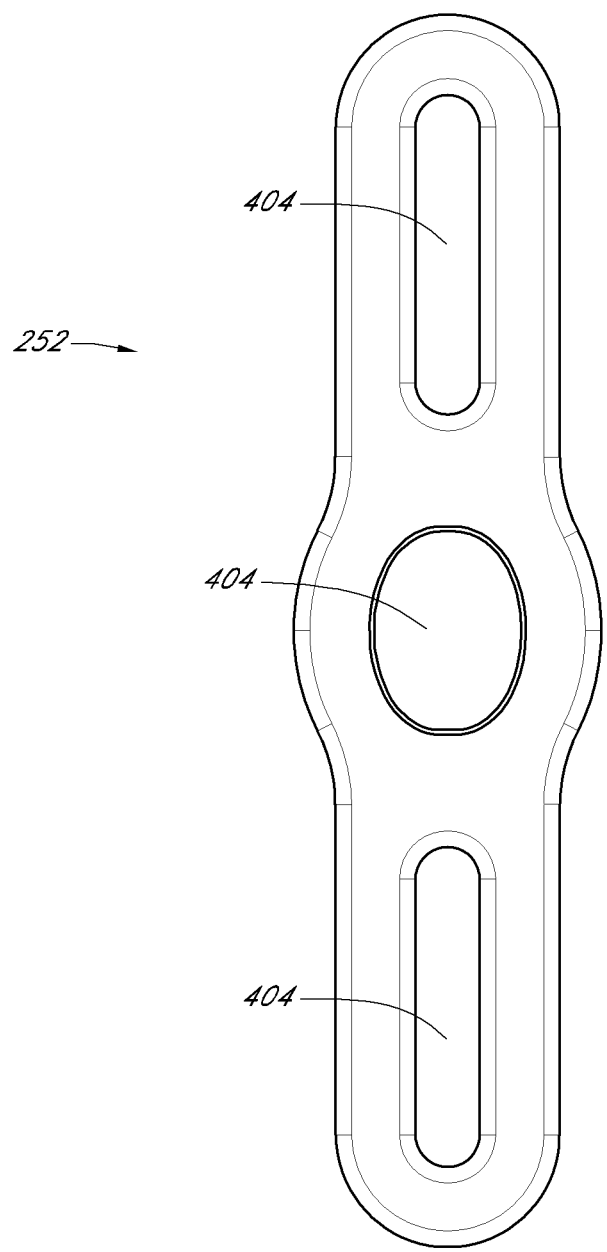
Figure 44:
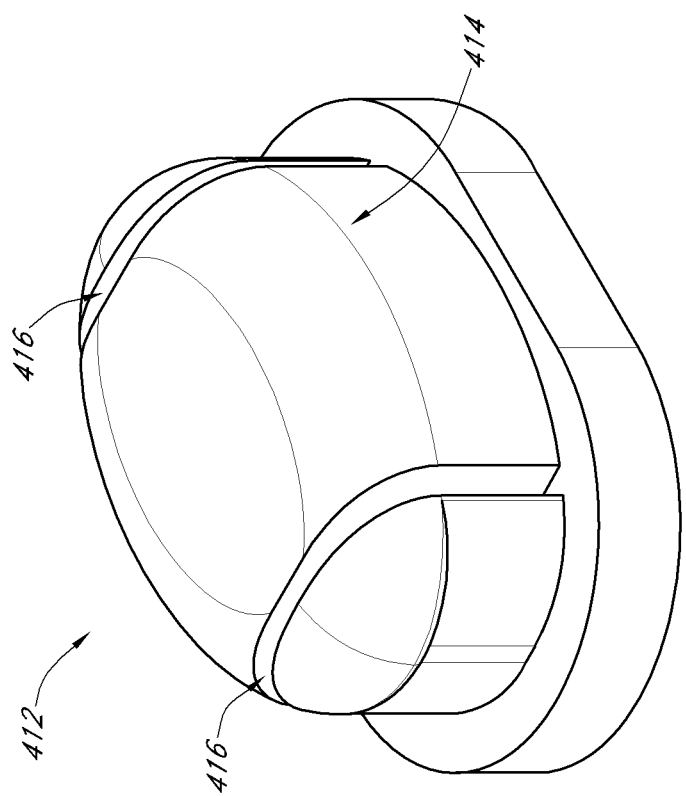
Figure 45:
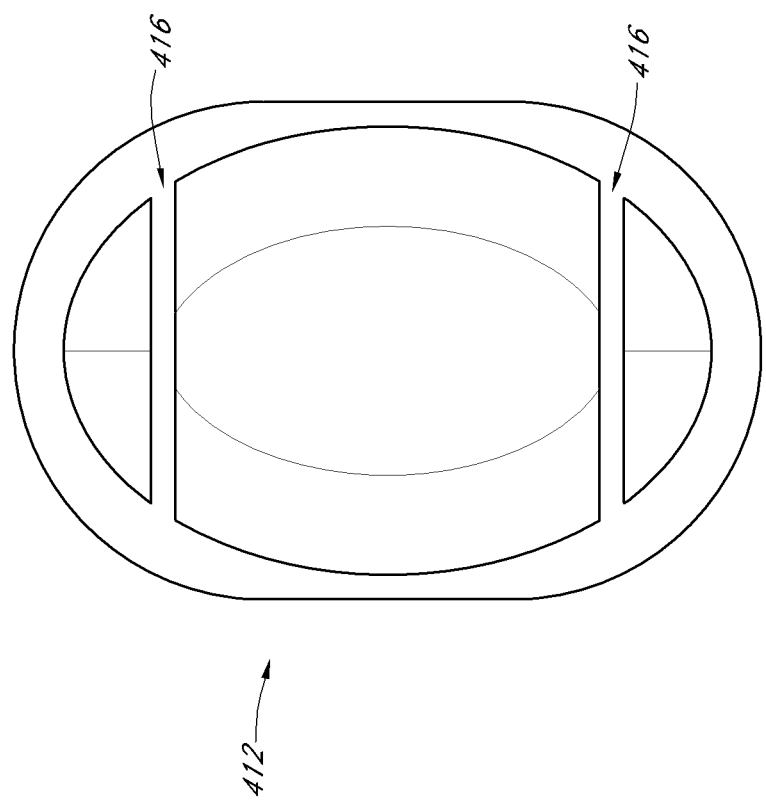
Figure 46E:
Figure 46D:
Figure 46C:
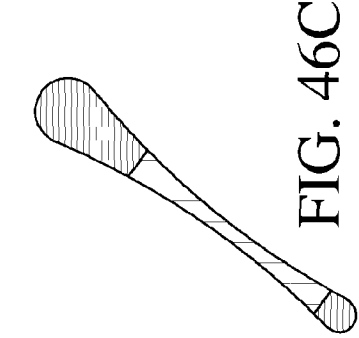
Figure 46F:
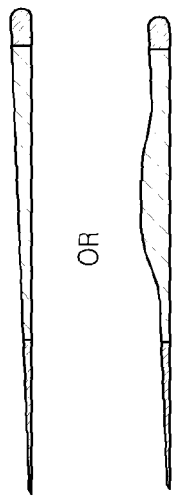
Figure 46A:
Figure 46B:

FIG. 42 illustrates a partial assembly of yet another configuration to secure a clip 252 to a mask base 114 of a mask assembly. The clip 252 sits within a recess 140 of the mask base 114. A cylindrical, button-head post 412 extends from the surface of the mask base 114 within the recess 140. The post 412 allows slight rotation of the clip 252 when attached thereto due to its cylindrical configuration. However, as shown in FIG. 36 and FIG. 37, the slot 404, channels 408 and slot walls 410 extend along the shorter planar direction of the inner catch 256, towards its front and back ends.

The inner catch 256 also includes several pressure bumps 414. As discussed above, the pressure bumps provide additional pressure against the outer cover 254 and inner catch 256, so that they are secured to one another.

Figure 41:
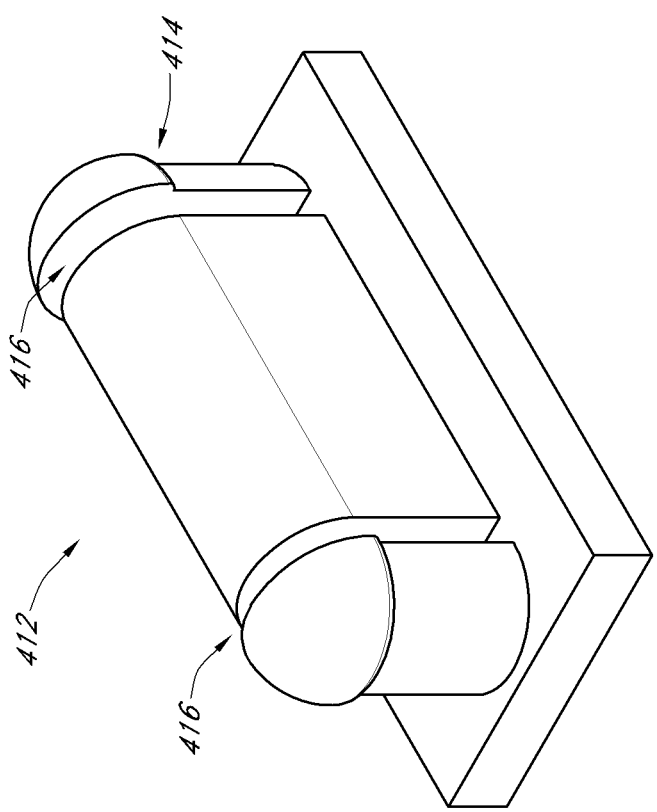

Additional configurations of a clip 252 are illustrated in FIGS. 38-45. The clip 252 of FIG. 38 includes three elongated, elliptical slots 404 and a finger tab 400. The finger tab 400 is used to create a lever to release the clip 252 from a mask assembly 102. The central slot 404 is sized to receive a mounting post 412 that extends from the outside surface of the mask body. One such suitable mounting post 412 is illustrated in FIG. 41. The mounting post 412 includes a ridge 414 and two slots 416. As the clip 252 is pressed onto the mounting post 412, the outer portions of the post 412 flex towards each other due to the spacing provided by the slots 416. Once the ridge 414 clears the upper surface of the clip 252, the mounting post 412 snaps back to its original position, and the ridge 414 locks the clip 252 in place, A similar configuration is shown in FIGS. 42-45. The clip 252 of FIG. 43 does not include a finger tab and its central opening 404 has a rounder, more elliptical shape than the elongated slots of FIGS. 38-41.

All of the foregoing configurations simplify the procedure for securing the mask assembly 102 to the user's head. For example, the clips 252 allow the headgear 106 to open up so that it is not a closed loop. By opening up, the headgear 106 may be swung around the head rather than forcing the user to pull his head through it.

With reference to FIG. 2, in addition to the straps 260, the headgear assembly 106 also comprises a back strap 280 and a top strap 282. Other head gear assemblies also can be used. The back strap 280 extends around the back of the head of the user U at a location generally above a nape of the neck but generally below the occipital protuberance. At a location rearward of the ear of the user, the back strap 280 forks into an upper arm 284 and a lower arm 286. The upper arm 284 arcs upward to a location above the ear of the user and then arcs downward to a location generally forward of the ear of the user. The lower arm 286 arcs downward to a location generally below the ear of the user and extends slightly forward of the ear.

The straps 260 can be connected to the back strap 280 in any suitable manner. In the illustrated configuration, the straps 260 connect to the upper arm 284 and the lower arm 286 respectively. Preferably, the upper arm 284 and the lower arm 286 are more rigid than the straps 260 such that the arms 284, 286 generally maintain shape as the headgear assembly 106 is being donned. In some configurations, each of the upper arm 284 and the lower arm 286 supports its own weight. In some configurations, each of the upper arm 284 and the lower arm 286 is structured to be tangle-free during donning. For example, the arms 284, 286 have sufficient torsion stiffness to reduce the likelihood of twisting when being put on.

Preferably, the straps 260 connect to at least one of the upper arm 284 and the lower arm 286 at a location forward of the ear. Such a configuration helps the user to locate the straps 260 without much difficulty. In addition, because the straps 260 in the illustrated configuration are embedded into the clips 252, the ends of the upper arms 284 and the lower arms 286 can comprise slots 290, 292 such that the straps 260 can be threaded through the slots 290, 292. In addition, the straps 260 can comprise an adjustment mechanism 294, such as a Velcro or buckle configuration. The adjustment mechanism 294 allows a force between the mask seal 110 and the face of the user U to be adjusted. Any suitable adjustment mechanism 294 can be used.

As shown in FIG. 2, the top strap 282 preferably is flexible and has an adjustable length. The top strap 282 connects to the upper arms 284 through a slot 296 and reduces the likelihood of the upper arms 284 sliding down the head of the user and contacting the ears of the user. Preferably, the top strap 282 connects to the upper arms 284 at a location generally above the ears of the user.

Advantageously, as shown in FIGS. 1 and 2, the straps 260 exert a force in the direction of the arrow F while they connect to the mask base 114 by movement in the direction C, which direction is generally normal to the direction of the force F. In other words, the straps 360 are tensioned by pulling forward and the clips 252 are connected to the mask base 114 by movement in a direction normal to the forward pull. Such a configuration eases securement of the interface 100 on the face of the user.

In another configuration, the headgear assembly 106 includes a semi-rigid headgear 380 (as shown in FIG. 41) to secure the mask assembly 102 to the user's head. The semi-rigid headgear 380 is formed as a composite structure comprising a semi-rigid strap 382 that is joined to a soft edging 384. For example, the soft edging 384 can be bonded to the semi-rigid strap 382 by plastic overmolding or by use of an adhesive. As shown in FIG. 46, the soft edging 384 can be butt-joined to the semi-rigid strap 382, without the soft edging 384 overlapping the semi-rigid strap 382, to maintain the continuous profile of the semi-rigid headgear 380. The semi-rigid strap 382 defines and maintains the semi-rigid headgear shape as tension is applied from the straps 260 to pull the mask assembly 102 towards the user's head. In other words, the semi-rigid strap 382 is sufficiently rigid along its planar axis to prevent its upper and lower arms 284, 286 from overly deforming under tension. The semi-rigid strap 382 can be made from a variety of rigid or semi-rigid materials, including plastic or metal. In some configurations, the semi-rigid strap 382 is made from PVC.

Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form, the headgear can be fitted in the correct orientation with very little if any instruction. In a self-supporting arrangement, the tendency of the straps to not tangle also reduces the time taken to fit the overall assembly.

As used herein, the term "semi-rigid" is used to denote that the headgear assembly is sufficiently stiff such that the headgear assembly 380 can assume a three-dimensional shape with dimensions approximating the head of the patient for which the headgear is designed to fit while also being sufficiently flexible to generally conform to the anatomy of the patient. For example, some of the other components (e.g., arms or straps) of the headgear assembly 380 may also be partially or wholly "semi-rigid" such that the components are capable of holding a three-dimensional form that is substantially self-supporting. A "semi-rigid" headgear assembly is not intended to mean that each and every component of the headgear assembly is necessarily semi-rigid. For example, the substantially three-dimensional form that the self-supporting headgear assembly 380 may assume may relate primarily to the rear and top portions of the headgear assembly 380. In addition, the semi-rigid headgear assembly 380 may include semi-rigid regions that extend forward of the ears and above the ears when placed on the head of the patient.

The left and right upper and lower arms 284, 286 may be formed of a semi-rigid material, as well. Where used herein, the semi-rigid materials may include molded plastic or sheet materials that include but are not limited to homogeneous plastic materials and bonded non-woven fiber materials.

In some configurations, one or more of arms or straps are formed of a substantially inelastic material. The arms or straps can be formed of a semi-rigid, self-supporting material such that the semi-rigid headgear assembly 380 can assume a substantially three-dimensional shape and generally does not tangle. In some configurations, the material can comprise a laminate structure of both conformable and semi-rigid portions, for example but without limitation. The semi-rigid strap 382 may be of a self-supporting, resilient, substantially inelastic material, such as Santoprene, polyolefin, polypropylene, polyethylene, foamed polyolefin, nylon or non-woven polymer material for example but without limitation. In some configurations, the semi-rigid strap 382 is formed from the polyethylene or polypropylene families. The material can be a low density polyethylene such as Dowlex 2517, which is a linear low density polyethylene that has a yield tensile strength of 9.65 MPa, a break tensile strength of 8.96 MPa, and a flexural modulus—2% secant of 234 MPa. The semi-rigid strap 382 preferably is formed of a material such that the semi-rigid headgear 380 is substantially shape-sustaining under its own weight regardless of its orientation. In some configurations, the semi-rigid strap 382 does not stretch more than approximately 6 mm under a 30 N tensile load. In some configurations, the semi-rigid strap 382 does not stretch more than approximately 3 mm under a 30 N tensile load.

In some configurations, the semi-rigid strap 382 is formed from non woven polyolefin (NWP), which is bonded (e.g., overmolded or laminated) with a polyolefin. In such configurations, the overmolded polyolefin material provides the principle shape sustaining properties. In addition, the softer NWP material is adapted to contact the skin and provide a desired comfort level. Furthermore, the NWP material may assist in providing the desired load bearing properties, such as the desired tensile load bearing properties.

The semi-rigid headgear 380 is generally formed of a semi-rigid material. Where used herein, the semi-rigid materials may include molded plastic or sheet materials that include but are not limited to homogeneous plastic materials and bonded non-woven fiber materials. The upper and lower arms 284, 286 also include such semi-rigid materials, as the arms 284, 286 are formed integrally with and are portions of the semi-rigid headgear 380. Preferably, the right and left lower arms 286 are formed as an integrated component that, in use, will extend around the back of the head and above the neck of the patient.

A soft edging 384 covers or attaches to at least a portion of the periphery of the semi-rigid strap 382. In one configuration, the soft edging 384 does not cover the front or rear faces of the semi-rigid strap 382. For example, the thicknesses of the soft edging 384 and semi-rigid strap 382 can be the same at the location where they are joined together.

The soft edging 384 provides a soft, comfortable interface between the periphery of the semi-rigid strap 382 and the user's skin. The soft edging 384 can be made from a variety of soft materials, including but not limited to a plastic, an elastomer, silicone or thermoplastic polyurethane (TPU) plastic. The soft edging 384 can have a Shore hardness in the range of 10-80 Shore A.

As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially inelastic.

The soft edging 384 can have a uniform thickness, or in some configurations, an uneven thickness. For example, in some configurations the soft edging 384 is the same thickness as the semi-rigid strap 382. In other configurations, the soft edging 384 is thinner than the semi-rigid strap 382, forms a bulbous end to the semi-rigid strap 382, or is simply thicker than the semi-rigid strap 382. A variety of cross-sectional views of the semi-rigid headgear 380 are shown in FIG. 46. Each cross-sectional view (A-A' through F-F') shows one possible configuration of semi-rigid strap 382 and soft edging 384 thicknesses, which may be combined as desired. For example, any one particular soft edging 384 thickness and shape could apply to a portion or the entire semi-rigid strap 382, or may be combined with any other particular covering thickness and shape shown in FIG. 46.

Many other thickness configurations may be provided, as well. In addition, material thickness may be symmetrically or asymmetrically applied to the semi-rigid strap 382. For example, cross-sectional views C-C' and F-F' are shown as asymmetric; however, in other configurations the thickness of either end the soft edging 384 is symmetrically applied to the semi-rigid strap 382. In some configurations the semi-rigid strap 382 is selectively thickened to provide extra rigidity and support. For example, the second of the two configurations illustrated as cross-sectional view F-F' has such a thickening. Finally, in some configurations, venting through-holes 396 are provided throughout the semi-rigid headgear 380 (such as on the semi-rigid strap 382, as shown in FIG. 46, or on soft edging 384) to provide ventilation and sweat management.

When laid flat, as shown in FIG. 46, the semi-rigid headgear 380 defines three C-shaped, arcuate regions 386, 388, 390. Two ear-surrounding regions 386, 388 are defined by upper and lower arms 284, 286, and a rear region 390 is defined by lower arms 286 and the back strap portion 280. The semi-rigid headgear 380 is flexible enough to bend to adapt to the shape of the user's head, such that the ear-surrounding regions 386, 388 at least partially surround or encircle the user's ears, and the rear region 390 at least partially surrounds or encircles the back of the user's head, above the neck.

The curvature of each arm 280, 284, 286 can be selected to provide a comfortable fit and to facilitate application and removal of the semi-rigid headgear 380 from the user's head. For example, in the illustrated configuration, the upper arms 284 have a concave curvature and the lower arms 286 have a convex curvature with respect to the opening in the upper ear surrounding arcuate regions 386, 388. The back strap portion 280 and the lower arms 286 all have a concave curvature with respect to opening in the neck surrounding arcuate region 390. These curvatures facilitate application and removal of the semi-rigid headgear 380 from the user's head by, for example, providing openings to the arcuate regions sized and oriented to easily fit over a user's neck and ears.

The configuration of FIG. 46 utilizes integrated crown straps comprising first and second crown arms 392, 394 to secure the semi-rigid headgear 380 to the user's head. Once the semi-rigid headgear 380 is positioned to partially surround the user's head, the first and second crown arms 392, 394 are brought into contact with one another to secure the semi-rigid headgear 380 in place. Any of a variety of mechanisms can be provided with the first and second crown arms 392, 394 to enable them to attach to one another. For example, in some configurations, a hook-and-loop fabric (e.g., Velcro), or one or more snaps or clips can be used to attach the first and second crown arms 392, 394 to one another.

The crown straps extend laterally over the top of the skull in line with the ears. When the crown straps extend in this manner and the arcuate regions 386, 388 are positioned to partially encircle the user's ears, the back strap 280 of the semi-rigid headgear 380 should locate on or below the inion. The user's inion is the most prominent projection of the occipital bone at the posterioinferior portion of the skull. In other words, the inion is the highest point of the external occipital protuberance. The semi-rigid headgear 380 can be positioned on the user's head according to any desired configuration.

For example, the back strap portion 280 is adapted to engage with the rear of head of the user. Preferably, the back strap portion 280 is adapted to engage with the head at a location on or below the external occipital protuberance. The back strap portion 280 spans the distance around the back of the head and extends to each side of the head. In some configurations, the back strap portion 280 comprises a longitudinal center that is adapted to be located about 25 degrees below a horizontal plane that extends through the ear canal of the patient.

On either side of the head, the semi-rigid headgear 380 extends upward and downward into left and right side regions that form arcuate regions 386, 388. The side regions are adapted to extend behind the ears of the patient. Preferably, the side regions also are adapted to extend behind the mastoid processes of the patient. Each of the left and right side regions of the semi-rigid headgear 380 extends into or comprises an arched portion 386, 388. The arched portions 386, 388 bend forward. The arched portions 386, 388 are adapted to extend around the respective ears of the patient. Preferably, each of the arched portions 386, 388 terminates at a respective termination portion. The termination portions preferably are adapted to be located forward of the ears of the patient. In some configurations, the side regions and the arched portions 386, 388 of the semi-rigid headgear 380 do not include a soft inner padding portion but may comprise a self-supporting, resilient material that is in direct contact with the head/hair of the patient.

The top portion of the semi-rigid headgear 380 connects the arched portions 386, 388 together. The top portion can be positioned forward of the ears in some configurations. Preferably, the top portion is positioned generally vertical from the ears. More preferably, a longitudinal center of the top portion is adapted to be spaced more than 13 mm, preferably between 13-100 mm, rearward of a vertical plane that intersects the ear canals. In some configurations, the top portion comprises a first segment 392 and a second segment 394 with the first segment 392 and the second segment 394 combining to form the top portion. The first segment 394 extends upward from an apex of the left arched portion 386 while the second segment 392 extends upward from an apex of the right arched portion 388. Preferably, the top portion is formed of a self-supporting and semi-rigid material. In some configurations, the top portion does not include any backing, including a soft padded backing layer.

Figure 47:
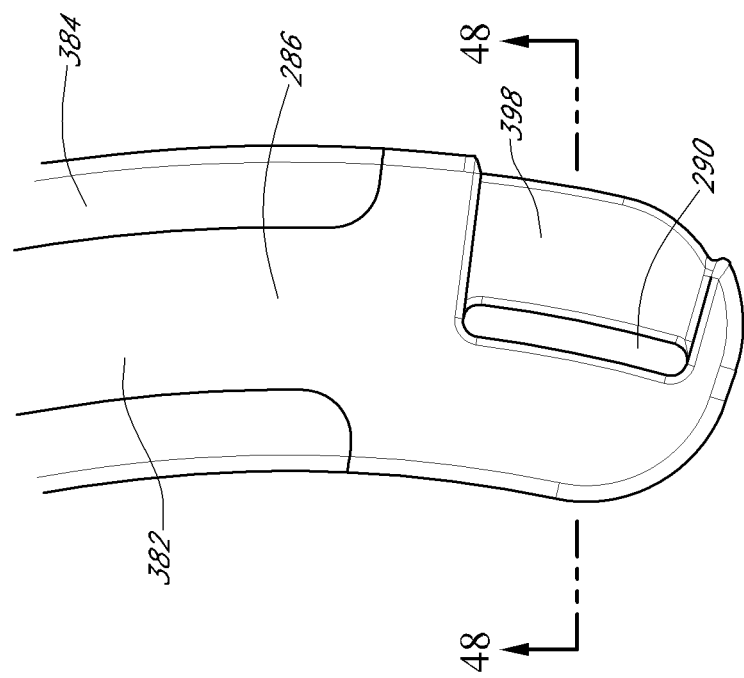
FIG. 47 is an enlarged view of the end region of a lower arm of FIG. 46.
Figure 48:
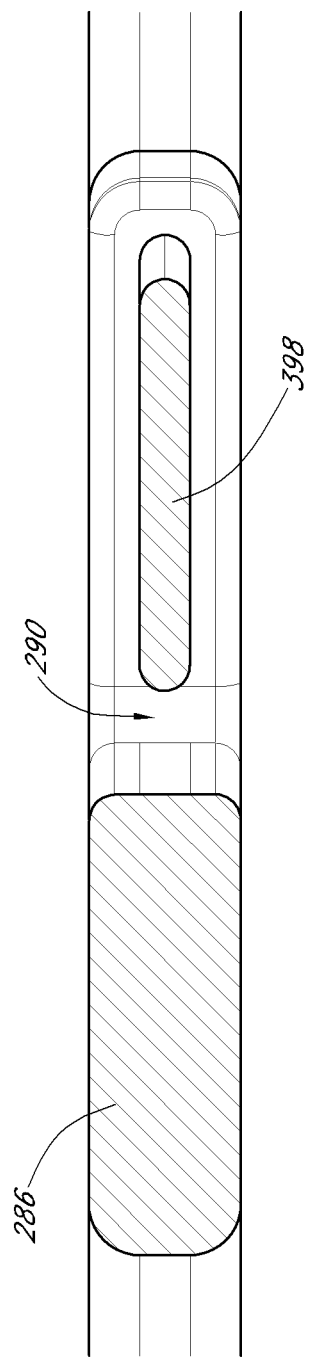
FIG. 48 is an enlarged cross-sectional view of the end region of FIG. 47.

Each of the upper and lower arms 284, 286 comprises a slot 292, 290 near each arm end. Each slot is configured to receive straps 260 from the mask assembly 102, as shown in FIG. 2. In addition, the portion 398 of the semi-rigid headgear 380 covered by straps 260 is thinner than the corresponding arm 284, 286 in order to accommodate the thickness of the strap 260. For example, as shown in FIGS. 47 and 48, the semi-rigid headgear portion 398 is thinner than the arm 286. The portion 398 is dimensioned such that when the strap 260 is inserted into the slot 290 and tensioned, its thickness will not extend beyond the arm 286. By maintaining the strap 260 and portion 398 thickness less than the arm 286 thickness, the strap 260 does not irritate the user when worn.

Figure 49:
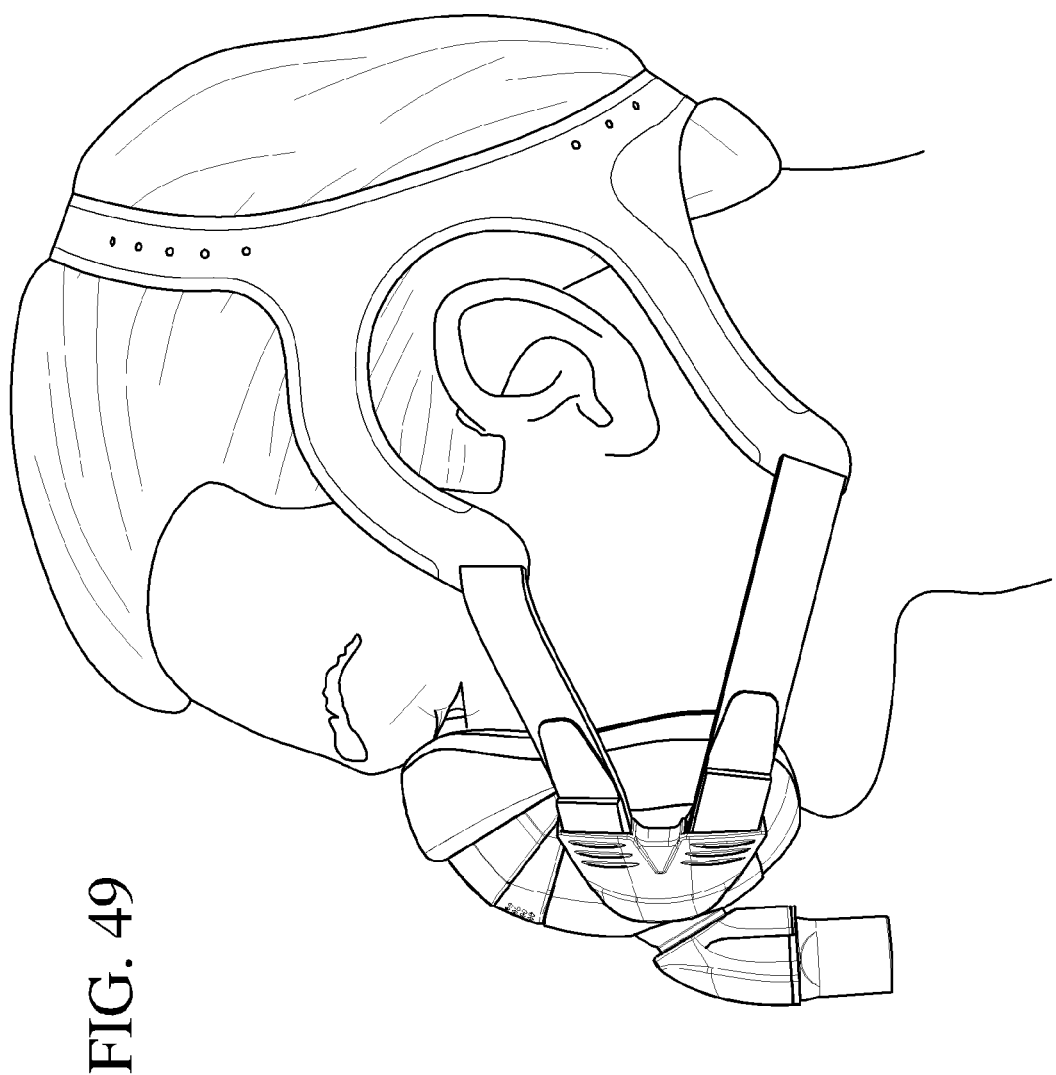
FIG. 49 is a side view photograph of the backbone of FIG. 46 attached to a user's head.
Figure 50:
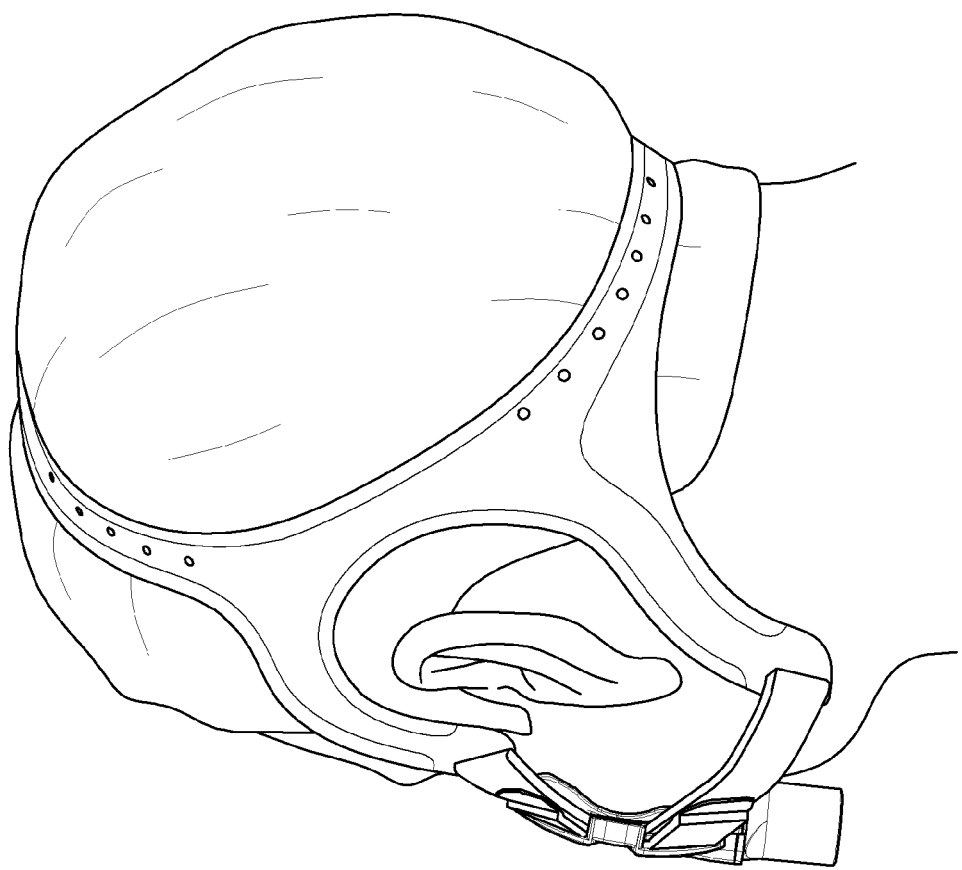
FIG. 50 is a rear perspective view photograph of the backbone of FIG. 46 attached to a user's head.

In addition, the upper arms 284 are configured to extend downward from a location above the user's ear such that the adjustable top straps 260 extend no closer than about 10 mm to the user's eye when worn. The lower arm 286 is configured to be located off of the user's neck when the head is tilted up and down, and the termination point of the lower arm 286 is located generally below the user's ears so that the lower strap as attached to the lower arm 286 angles upwards from the termination point 290 to the mask assembly 120. In such a configuration, as illustrated in FIGS. 49 and 50, the lower straps and the upper straps form a triangle, and the space between the lower straps and the upper straps on the mask is smaller than the space between the lower straps and the upper straps on the headgear, thereby stabilizing the mask assembly 120 against upward and downward movements.

Figure 26:
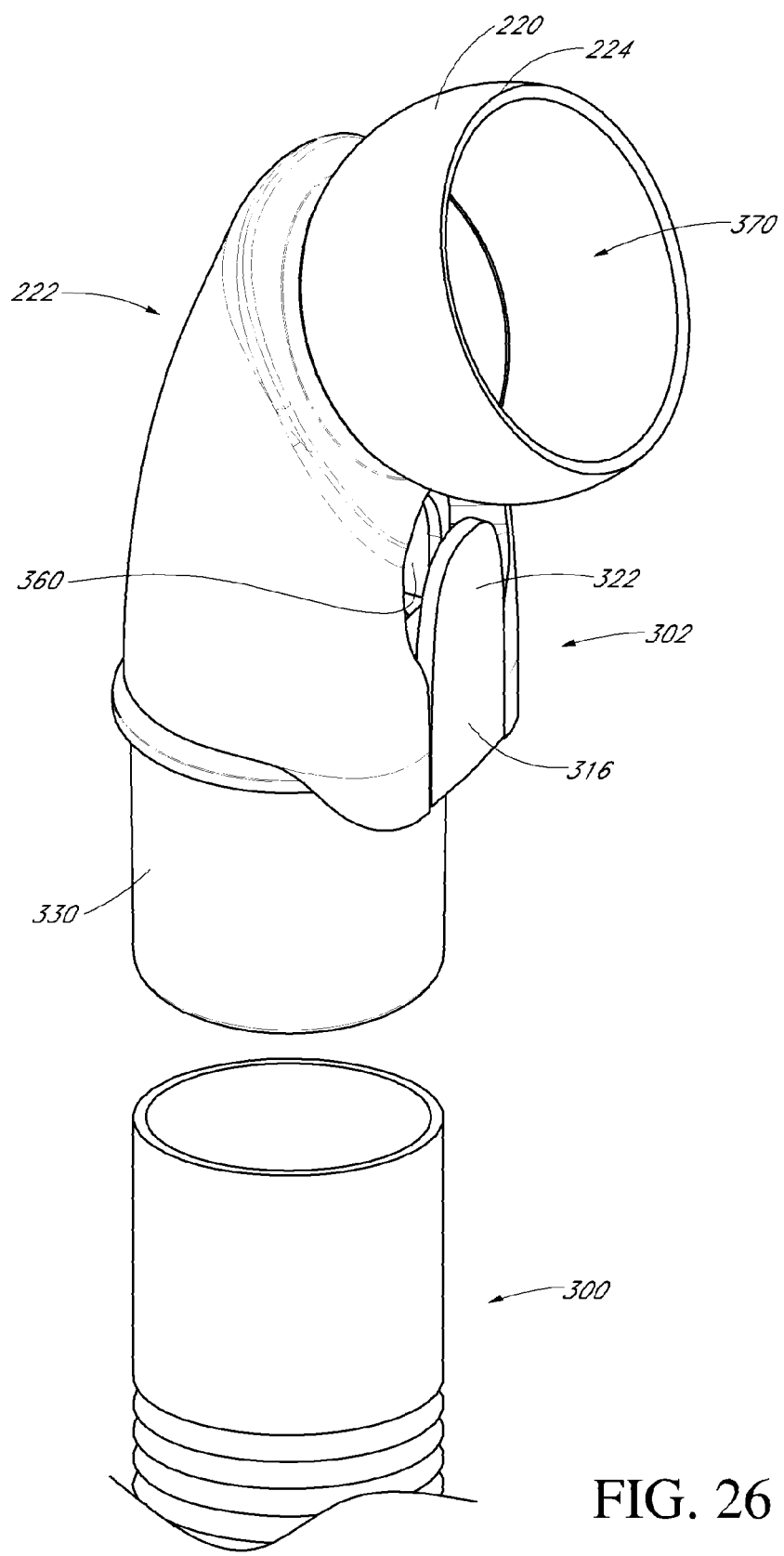
FIG. 26 is a perspective view of the connection port assembly of FIG. 1.
Figure 27:
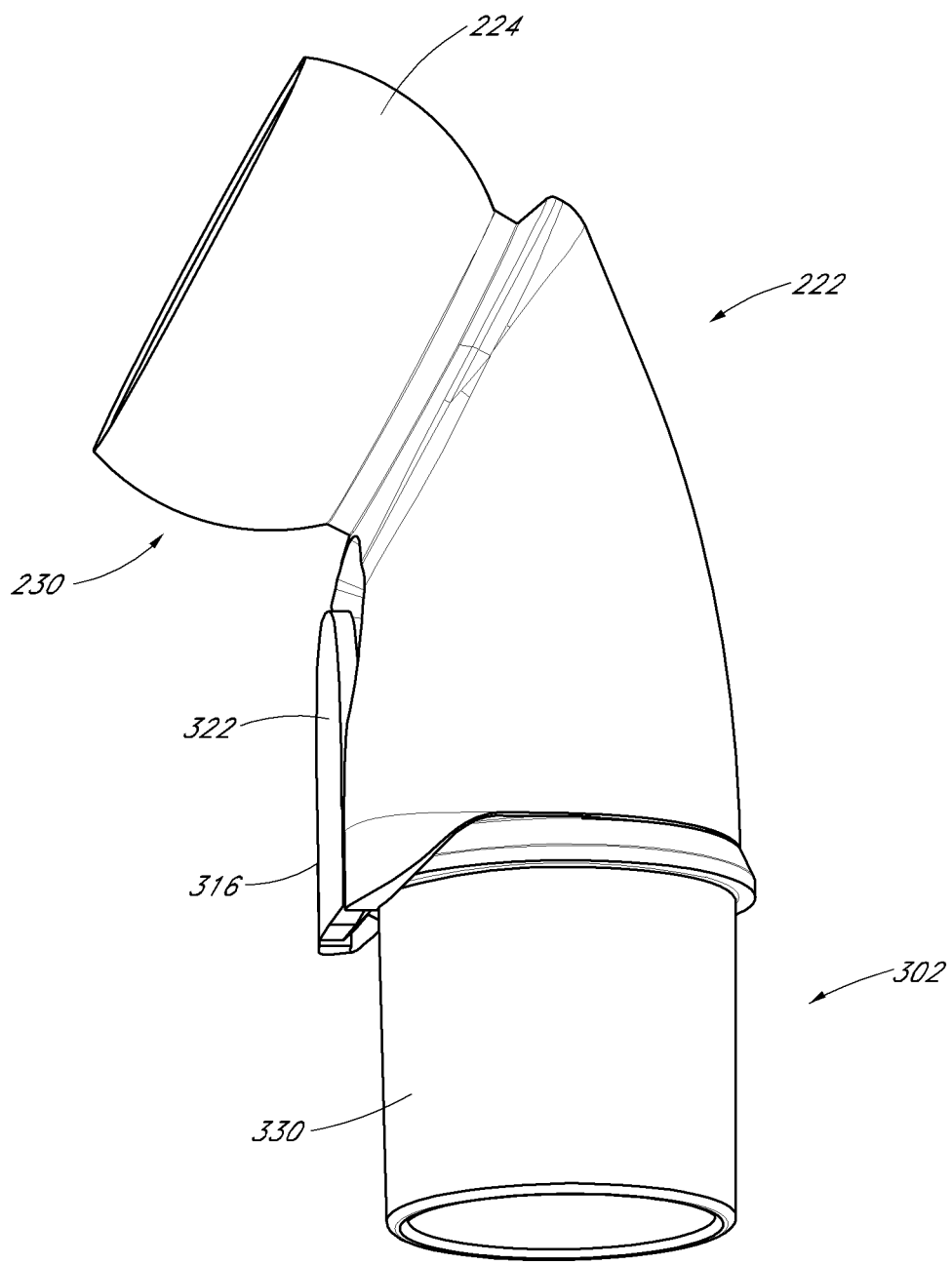
FIG. 27 is a side elevation view of the connection port assembly of FIG. 26.

With reference to FIG. 26, the elbow 222 connects to a conduit 300 through a disconnectable swivel assembly 302. As shown in the section view of FIG. 52, the elbow 222 comprises a stem 304 that comprises an inner wall 306 at the base. The inner wall 306 comprises a recess 308.

Figure 53:
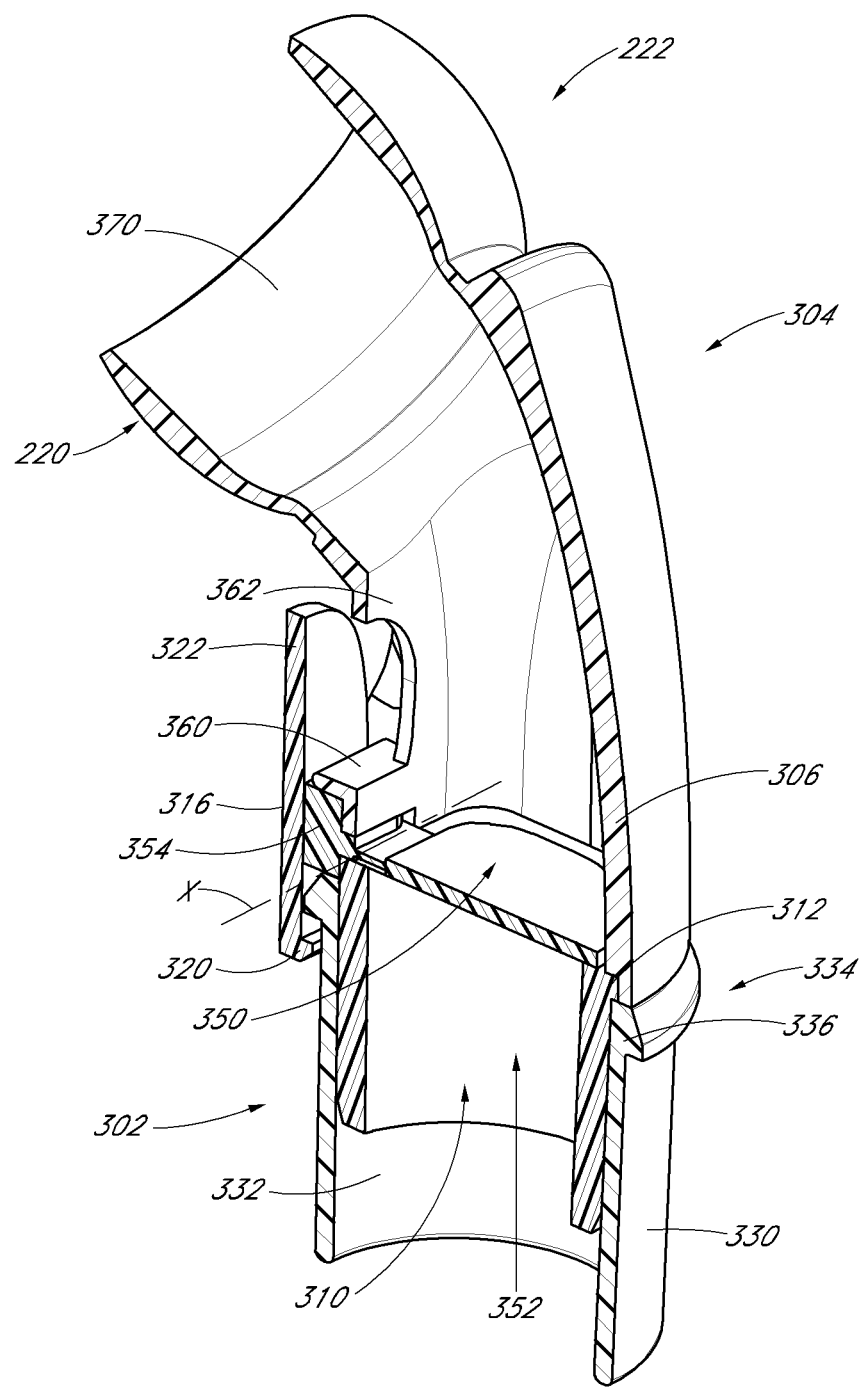
FIG. 53 is a sectioned perspective view of the connection port assembly of FIG. 22.
Figure 54:
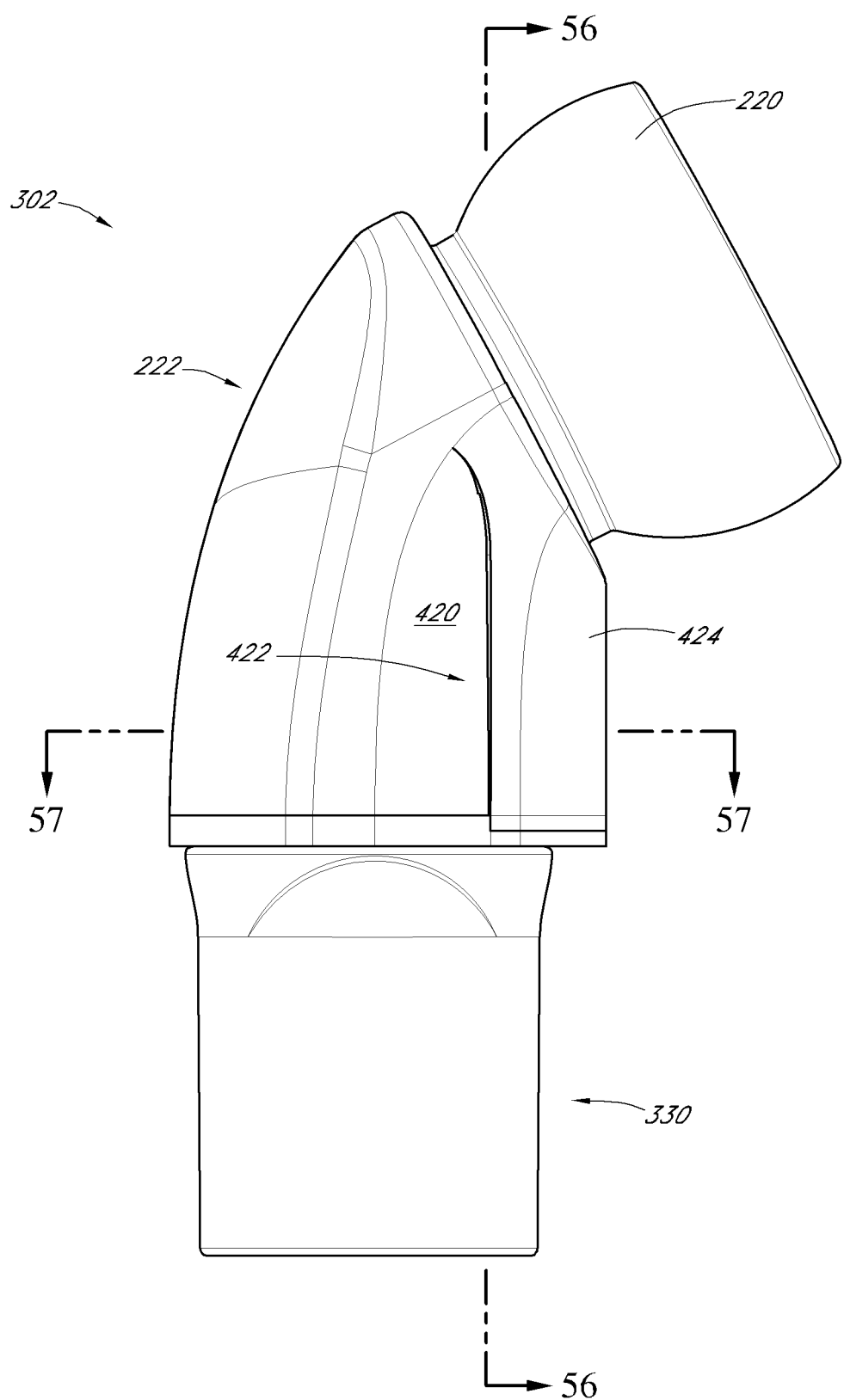
FIG. 54 is a side view of another configuration of a swivel assembly.

A sleeve 310 comprises a flange 312 that is received within the recess 308. The sleeve 310 can be secured into position within the elbow 222 using any suitable technique. The sleeve 310 comprises a generally cylindrical outer wall 314. The flange 312 comprises a section that extends outward to connect to a lever 316. Preferably, the flange 312 and the lever 316 are integrally formed. With reference to FIG. 53, the lever 316 includes a lower inwardly extending catch 320 and is capable of pivoting about the section that connects the lever 316 to the flange 312. Thus, pressing inward on an upper portion 322 of the lever 316 results in the catch 320 moving away from the generally cylindrical outer wall 314 of the sleeve 310.

A swivel 330 comprises a generally cylindrical inner wall 332. The inner wall 332 slides over the outer wall 314 of the sleeve 310 such that a sliding fit results between the swivel 330 and the sleeve 310. An upper portion 334 comprises a shoulder 336. The catch 320 of the lever 316 can secure the swivel 330 in axial position on the sleeve 310 by engaging with the shoulder 336. When the upper portion 322 of the lever 316 is depressed, the catch 320 moves away from the shoulder 336, which allows the swivel 330 to be removed from the sleeve 310.

Figure 52:
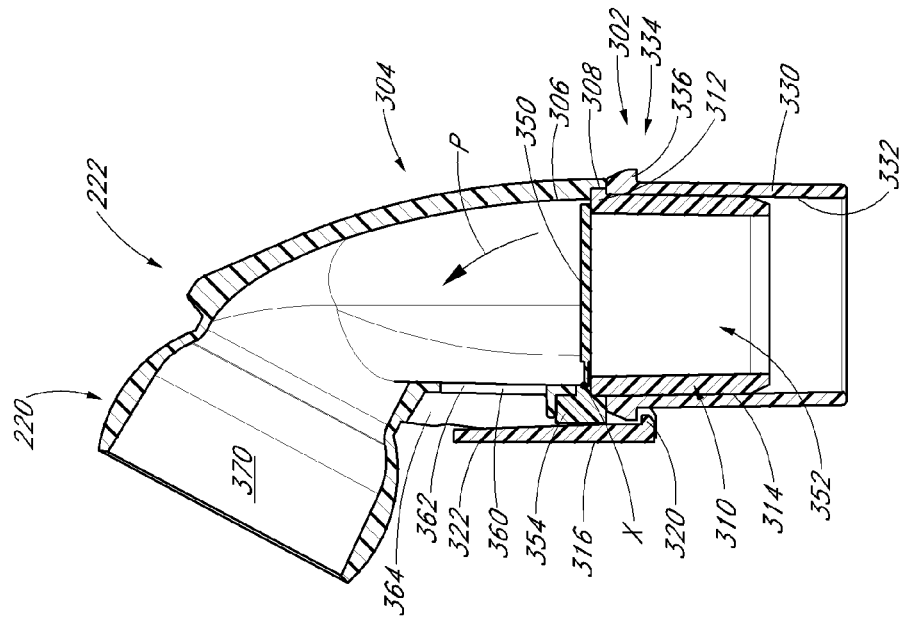
FIG. 52 is a sectioned side elevation view of the connection port assembly of FIG. 27.
Figure 51:
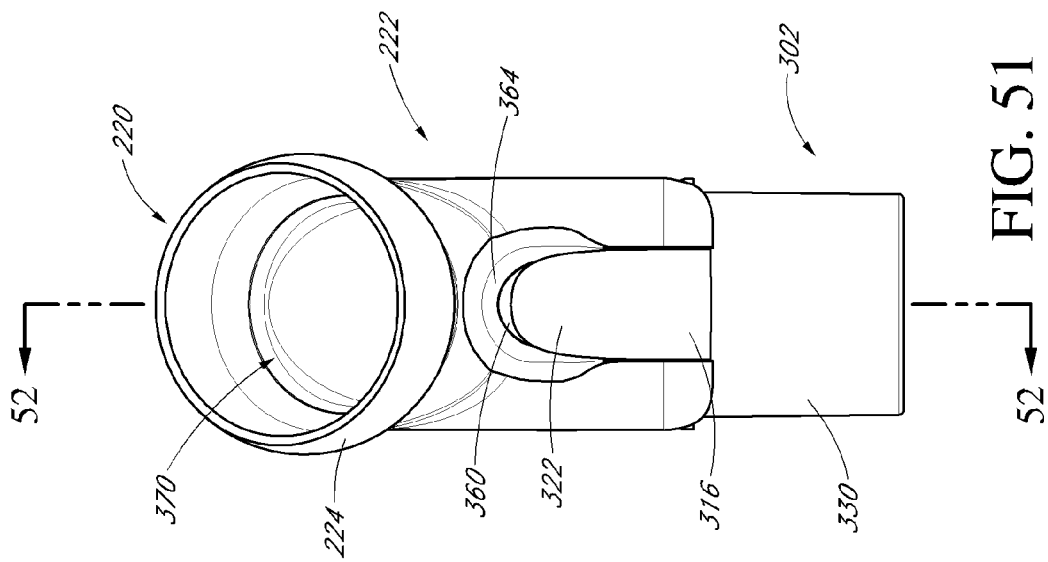
FIG. 51 is a rear elevation view of the connection port assembly of FIG. 27.

A flap 350 can be mounted between the stem 304 and the sleeve 310. In the illustrated configuration, the flap 350 extends into a flow channel 352 from a base 354 that is sandwiched between the stem 304 and the sleeve 310. The flap 350 can pivot upward (as shown in FIG. 52, see arrow P) about an axis X (see FIG. 53) away from the sleeve 310 such that flow from a positive pressure generator can continue generally unobstructed to the user through the interface 100. The flap 350 pivots downward into contact with the sleeve 310 to seal the flow channel 352 in the event that the positive pressure source stops providing a pressurized flow of air. In some configurations, the flap 350 will not fully contact the sleeve 310. In some configurations, the flap 350 will not seal the channel 352 when in the down position.

With reference to FIG. 53, a port 360 is defined through the elbow 222 at a location above the flap 350. The port 360 preferably is positioned along a portion of the elbow 222 that is in the vicinity of the axis X. In some configurations, the port 360 is positioned to be substantially shielded by the flap 350 from an inspiratory flow of air. In other words, as the air pivots the flap 350 away from the sleeve 310, the flap 350 is moved into a position that at least partially or completely covers the port 360.

In some configurations, the port 360 extends through a wall of the elbow 222 that comprises a generally planar inner wall 362. The generally planar inner wall 362 helps the flap 350 to generally seal the port 360 when the flap is moved upward away from the flange 312 of the sleeve 310.

In some configurations, the lever 316 overlies a majority of the port 360 such that the port 360 is generally obscured from view. As shown in FIG. 52, however, a gap 364 preferably surrounds at least a portion of the lever 316 such that a relatively free flow of air can pass through the port 360 when the flap 350 does not overly the port 360. In addition, in some configurations, the port 360 and the lever 316 are positioned on a same side of the elbow 222 as an opening 370 defined within the ball end 220, which opening is positioned within the mask assembly 102 when the connection port assembly 104 is assembled to the mask assembly 102. Advantageously, such a positioning places the port 360 in a position on the elbow 222 that faces the user. Such a location further obscures the port 360 from view during use, which results in a more aesthetically pleasing configuration. Moreover, because flow through the port 360 will be very infrequent, having the port 360 disposed toward the user will not cause any significant discomfort for the user.

While not shown, the elbow 222 also can comprise one or more bias flow vent holes. The bias flow vent holes preferably are positioned in a forwardly directed orientation such that any bias flow does not directly impinge upon the user.

Figure 55:
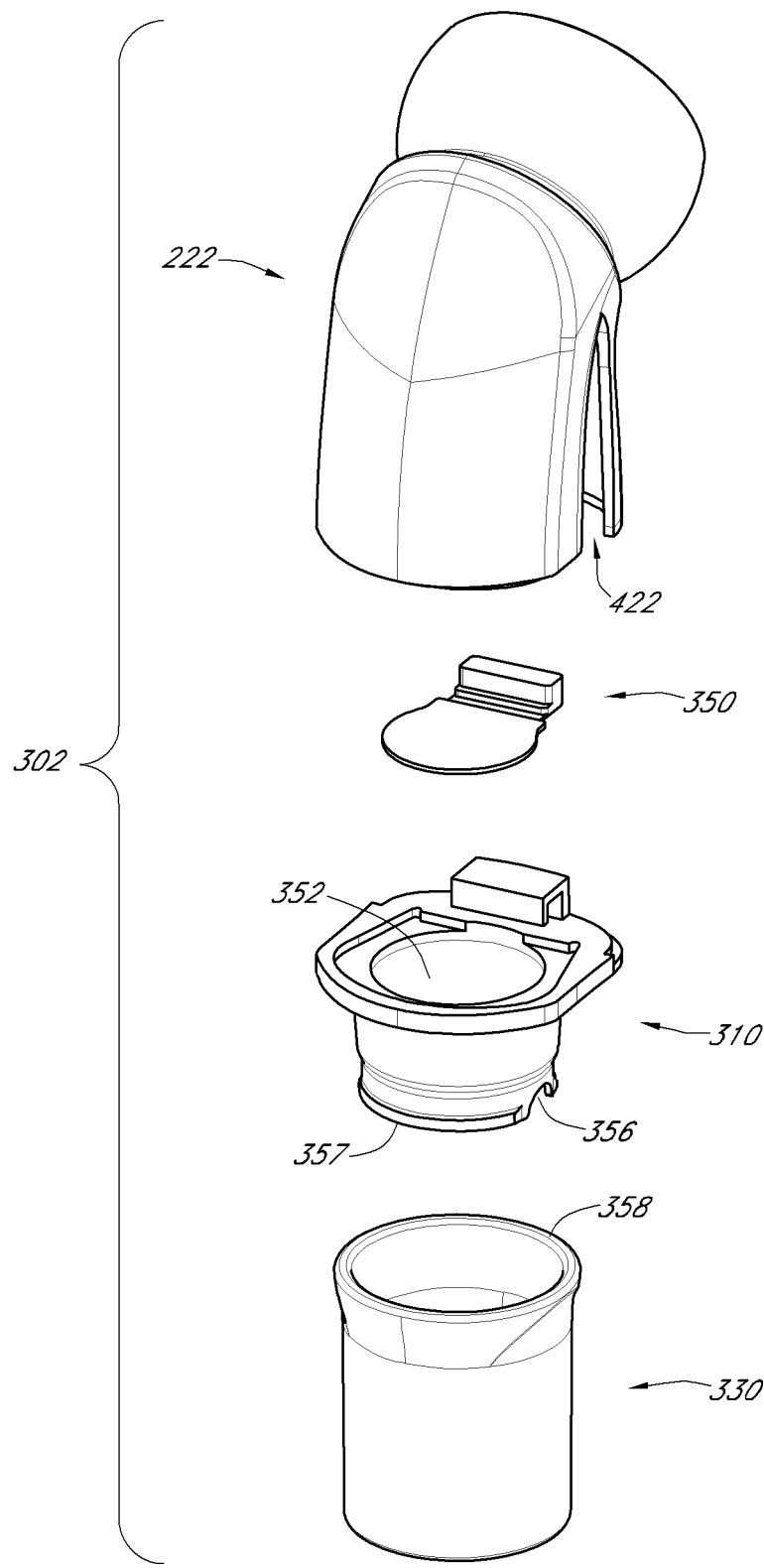
FIG. 55 is an exploded view of the swivel assembly of FIG. 54.
Figure 56:
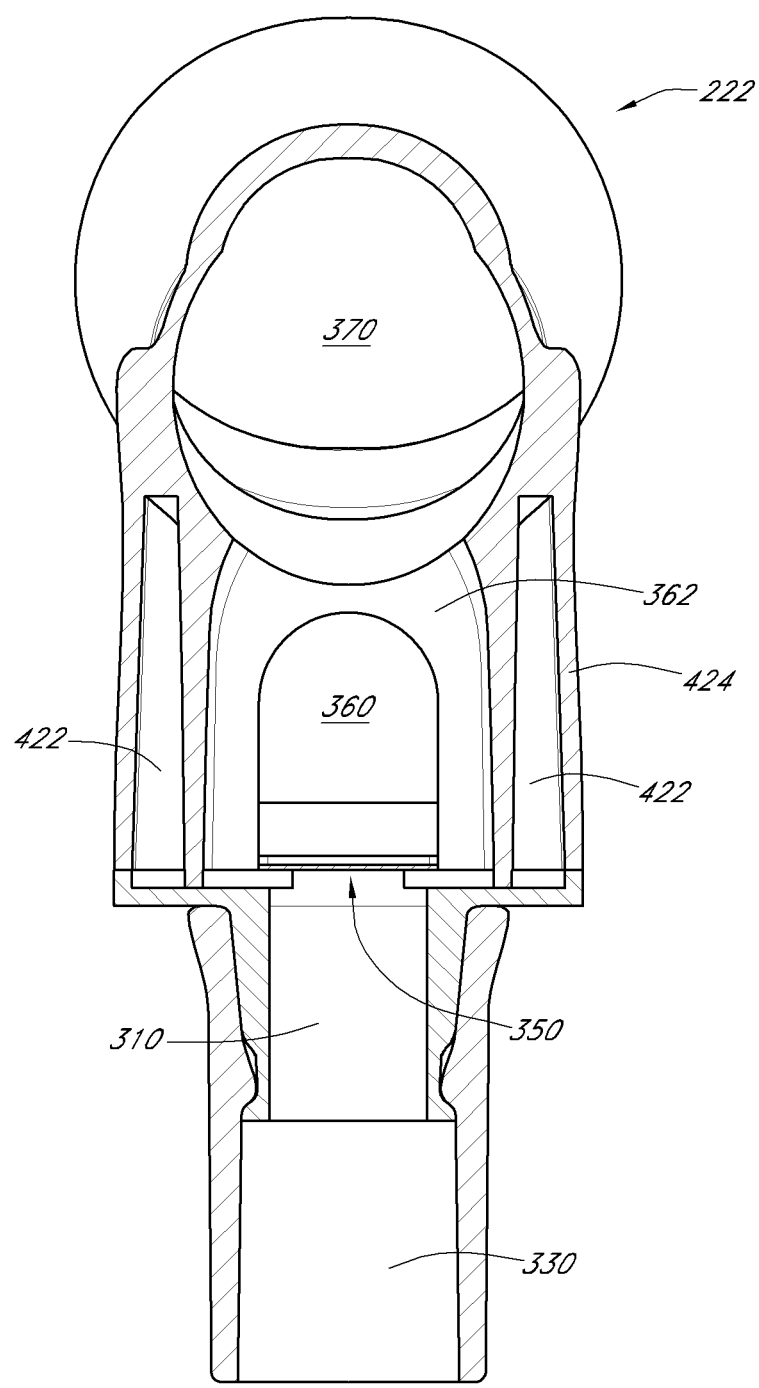
FIG. 56 is a cross-sectional view taken along line 56-56 of FIG. 53.
Figure 57:
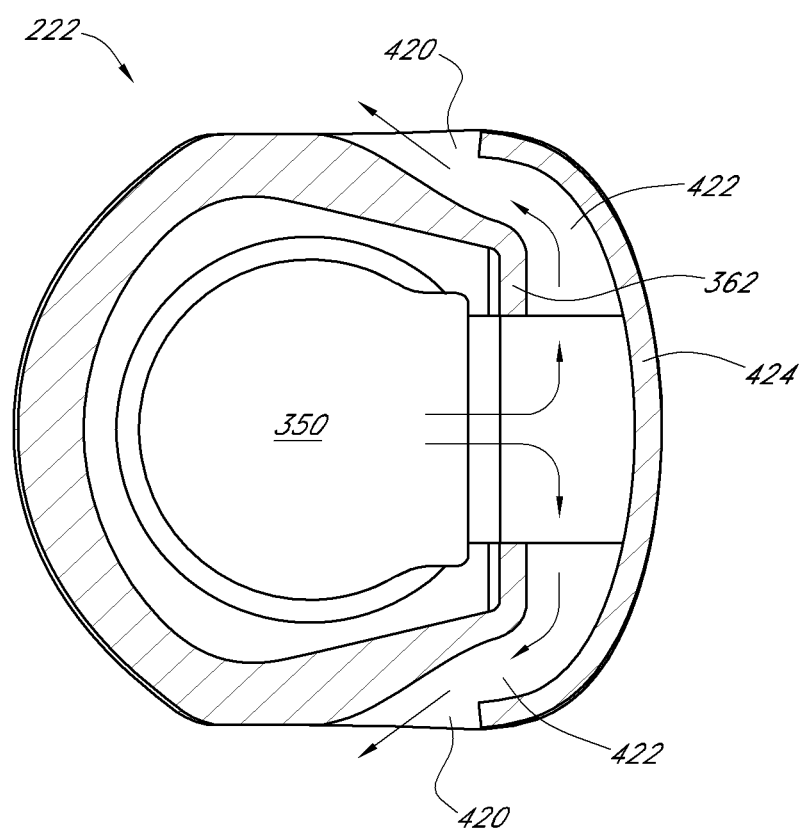
FIG. 57 is a cross-sectional view taken along line 57-57 of FIG. 53.

Another configuration of an elbow assembly 302 is illustrated in FIGS. 54-57. The elbow assembly 302 comprises an elbow 222, a sleeve, 310, and/or a swivel 330, as shown in FIG. 55. In some configurations, the elbow assembly 302 only includes the elbow 222 and sleeve and omits the swivel 330. The swivel may be permanently or removably attached to the sleeve 310 and elbow 222; in some configuration, the swivel 330 is integrally formed with the end of the delivery conduit. A flap 350 is positioned over the sleeve 310 such that it at least partially obstructs the sleeve's flow channel 352. The elbow assembly 302 functions similarly to the elbow assembly 302 of FIGS. 26, 27, and 51-53; however, the elbow assembly 302 of FIGS. 54-57 provides the additional benefit of directing gases away from the patient when the flap 350 drops to its closed position (as shown in FIGS. 56 and 57).

With reference to FIG. 55, the sleeve 310 preferably comprises two or more cut out regions or recesses 356. The recesses 356 can have any suitable shape and, in the illustrated configuration, the recesses 356 comprise a semicircular configuration that extends upward into the sleeve 310. The sleeve 310 also comprises at least one bump 357, and preferably two or more bumps 357. Preferably, each of the bumps 357 extends around an arc of about 70 degrees. More preferably, each of the bumps 357 is generally centered between two recesses 356 and each of the bumps 357 extends about 70 degrees around an outer surface of the sleeve 310.

The swivel 330 preferably is generally cylindrical in configuration. As shown in FIG. 55, the swivel 330 has an inwardly extending ridge 358. The ridge 358 preferably encircles the entire inner surface. In some configurations, the ridge 358 can be interrupted. Preferably, however, the ridge 358 does not have any interruptions large enough to accommodate the entire bump 357 such that the ridge 358 and the bump 357 can cooperate to keep the swivel 330 mounted over the sleeve 310. When assembling the swivel 330 to the sleeve 310, the recesses 216 allow the bumps 220 to deflect inward such that the bumps 357 can slide over the ridge 358 and then snap back outward to secure the bumps 357 under the ridge 358.

The elbow 222 comprises openings 420 at its sides that are in fluid communication with an air venting channel 422. The air venting channel 422 is formed by the spacing between the elbow's inner and outer walls 362, 424, as shown in FIGS. 56 and 57.

When the flap 350 drops to its closed position, as shown in FIGS. 56 and 57, air exhaled from the user enters opening 370 of the elbow 222. The exhalation flows through the port 360 in the elbow's inner wall 362, and through the venting channel 422 until it exits the elbow 222 via the opening 420.

The configuration of FIGS. 54-57 provides a reduced overall length and improves product aesthetic by eliminating an unsightly hole positioned at the front of the elbow 222. In addition, the configuration of FIGS. 54-57 and improves patient comfort by preventing air from being directed towards the user. Instead, openings 420 direct air flow out of the sides of the elbow 222 and away from the patient.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A mask assembly for use with a respiratory interface configured to provide respiratory gas to a user in use including improved nose tabs configured to provide additional lateral compressive forces against a user's nose for nose bridge support and to reduce air leakage, the mask assembly comprising:
   a mask base comprising a mask base wall made of a first material, the mask base wall having a distal portion defining a respiratory gases inlet, the mask base wall extending from the distal portion, around the respiratory gases inlet and configured to extend proximally toward a user in use, to a proximal peripheral edge of the mask base wall, the mask base wall having an inner mask base wall surface;
   a seal member made of a second material that is more flexible than the first material, the seal member having a distal peripheral edge, a sidewall portion, a face contacting wall portion, and a free edge of the face contacting wall portion, the distal peripheral edge being connected to the proximal peripheral edge of the mask base wall, the sidewall portion extending from the distal peripheral edge of the seal member and configured to extend proximally toward a user in use, to the face contacting wall portion of the seal member, the free edge of the face contacting wall portion disposed radially inwardly from the sidewall portion, the sidewall portion having a sidewall outer surface facing radially outwardly and the face contacting wall portion having a face contacting wall outer surface configured to face toward a user in use, wherein the sidewall portion and the face contacting wall portion have a sidewall inner surface and a face contacting wall inner surface, respectively, and wherein the sidewall inner surface, the face contacting wall inner surface, and the inner mask base wall surface define an inwardly facing surface of the mask assembly;
   a first tab integrally formed with the seal member, the first tab having a proximal end and a distal end, the proximal end of the first tab extending from the face contacting wall portion to the distal end of the first tab which is coupled with the inwardly facing surface of the mask assembly at a first location that is disposed distally from the face contacting wall portion, the first tab including first and second side edges extending from the proximal end to the distal end, the first tab forming a first loop with the inwardly facing surface of the mask assembly and configured to press at least part of the face contacting wall outer surface laterally against a first side of a user's nose in use; and
   a second tab integrally formed with the seal member, the second tab having a proximal end and a distal end, the proximal end of the second tab extending from the face contacting wall portion to the distal end of the second tab which is coupled with the inwardly facing surface of the mask assembly at a second location that is disposed distally from the face contacting wall portion, the second tab including first and second side edges extending from the proximal end to the distal end, the second tab forming a second loop with the inwardly facing surface of the mask assembly and configured to press at least part of the face contacting wall outer surface laterally against a second side of the user's nose in use.

2. The mask assembly according to claim 1, wherein the distal ends of the first and second tabs are adjustably connected to portions of the mask assembly, respectively.

3. The mask assembly according to claim 1, wherein the proximal ends of the first and second tabs extend from the free edge of the face contacting wall portion and the first and second tabs tapering toward the distal ends, respectively.

4. A mask assembly for use with a respiratory interface configured to provide respiratory gas to a user, the mask assembly comprising:
   a mask base comprising a mask base wall, the mask base wall having a distal portion defining a respiratory gases inlet, the mask base wall extending from the distal portion to a peripheral edge of the mask base wall, the mask base wall having an inner base wall surface;
   a seal member having a distal peripheral edge, a sidewall portion, and a face contacting wall portion, the distal peripheral edge being connected to the peripheral edge of the mask base wall, the sidewall portion extending from the distal peripheral edge of the seal member and configured to extend proximally toward a user in use, to the face contacting wall portion of the seal member, wherein the sidewall portion and the face contacting wall portion comprise a sidewall inner surface and a face contacting wall inner surface, respectively, and wherein the face contacting wall inner surface, the sidewall inner surface, and the inner base wall surface define an inwardly facing surface of the mask assembly; and a first tab having a proximal end and a distal end, the proximal end of the first tab extending from a free edge of the face contacting wall portion to the distal end of the first tab which is coupled with the inwardly facing surface of the mask assembly at a second location that is disposed distally from the proximal end such that the first tab forms a first loop with the inwardly facing surface of the mask assembly, wherein the first tab includes first and second side edges extending from the proximal end to the distal end.

5. The mask assembly according to claim 4, wherein the mask base wall is made of a first material, the seal member being made of a second material that is more flexible than the first material.

6. The mask assembly according to claim 4, wherein the free edge of the face contacting wall portion is disposed radially inwardly from the sidewall portion.

7. The mask assembly according to claim 4, wherein the first tab is integrally formed with the seal member and tapers toward the distal end of the first tab.

8. The mask assembly according to claim 4, wherein the first tab is configured to press at least part of an outer surface of the face contacting wall portion laterally against a first lateral side of a user's nose in use.

9. The mask assembly according to claim 8, additionally comprising a second tab having a proximal end and a distal end, the proximal end of the second tab extending from the free edge of the face contacting wall portion to the inwardly facing surface of the mask assembly at a third location that is disposed distally from the free edge of the face contacting wall portion, the second tab configured to press at least part of an outer surface of the face contacting wall portion laterally against a second side of a user's nose in use, opposite the first lateral side of the user's nose.

10. The mask assembly according to claim 4, additionally comprising a second tab having a proximal end and a distal end, the proximal end of the second tab extending from the face contacting wall portion to a third location disposed distally from the proximal end of the second tab.

11. A mask assembly for use with a respiratory interface configured to provide respiratory gas to a user, the mask assembly comprising:

a mask base comprising a distal inlet and a proximal peripheral edge;

a seal member having a sidewall portion and a face contacting wall portion, the sidewall portion being connected to the proximal peripheral edge of the mask base; and a first tab extending from a first proximal location of the face contacting wall portion to a first distal location of the mask assembly that is disposed distally from the first proximal location, wherein the first tab forms a first loop with an inner surface of the mask assembly, wherein the first tab is integrally formed with the seal member and includes first and second side edges extending from the first proximal location to the first distal location.

12. The mask assembly according to claim 11, wherein the sidewall portion comprises a sidewall inner surface, the face contacting wall portion comprises a face contacting wall inner surface, and the mask base comprises a mask base inner surface, and wherein the face contacting wall inner surface, the sidewall inner surface, and the mask base inner surface define the inner surface of the mask assembly.

13. The mask assembly according to claim 11, wherein the face contacting wall portion comprises a free edge, wherein a proximal end of the first tab extends from the free edge of the face contacting wall portion, the free edge of the face contacting wall portion being disposed radially inwardly from the sidewall portion.

14. The mask assembly according to claim 11, wherein the sidewall portion comprises a sidewall outer surface facing radially outwardly and the face contacting wall portion comprises a face contacting wall outer surface configured to face toward a user in use.

15. The mask assembly according to claim 11, wherein the first tab tapers toward the first distal location and is configured to press at least part of an outer surface of the face contacting wall portion laterally against a first side of a user's nose in use.

16. The mask assembly according to claim 15, additionally comprising a second tab configured to press at least part of an outer surface of the face contacting wall portion laterally against a second side of a user's nose in use, opposite the first lateral side.

17. The mask assembly according to claim 11, additionally comprising a second tab having a proximal end and a distal end, the proximal end of the second tab extending from a second proximal location on the seal member to a second distal location disposed distally from the second proximal location so as to form a second loop with the inner surface of the mask assembly.

18. The mask assembly according to claim 17, wherein the proximal end of the second tab extends from a free edge of the face contacting wall portion.

* * * * *